United States Patent
Tarcic et al.

(10) Patent No.: US 10,550,439 B2
(45) Date of Patent: Feb. 4, 2020

(54) METHODS FOR DETERMINING DRUG RESPONSE OF PATIENT SPECIFIC MUTATIONS

(71) Applicant: NOVELLUSDX LTD., Jerusalem (IL)

(72) Inventors: Gabi Tarcic, Mevasseret Zion (IL); Yoram Altschuler, Mevasseret Zion (IL)

(73) Assignee: NovellusDX Ltd., Jerusalem (IL)

( * ) Notice: Subject to any disclaimer, the term of this patent is extended or adjusted under 35 U.S.C. 154(b) by 0 days.

(21) Appl. No.: 15/327,499

(22) PCT Filed: Jul. 20, 2015

(86) PCT No.: PCT/IL2015/050746
§ 371 (c)(1),
(2) Date: Jan. 19, 2017

(87) PCT Pub. No.: WO2016/013007
PCT Pub. Date: Jan. 28, 2016

(65) Prior Publication Data
US 2017/0159137 A1    Jun. 8, 2017

Related U.S. Application Data

(60) Provisional application No. 62/026,715, filed on Jul. 21, 2014.

(51) Int. Cl.
*C12Q 1/68* (2018.01)
*C12Q 1/6897* (2018.01)
*C12Q 1/6886* (2018.01)

(52) U.S. Cl.
CPC ......... *C12Q 1/6897* (2013.01); *C12Q 1/6886* (2013.01); *C12Q 2600/106* (2013.01); *C12Q 2600/136* (2013.01); *C12Q 2600/156* (2013.01)

(58) Field of Classification Search
None
See application file for complete search history.

(56) References Cited

U.S. PATENT DOCUMENTS

| | | |
|---|---|---|
| 3,791,932 A | 2/1974 | Schuurs |
| 3,839,153 A | 10/1974 | Schuurs |
| 3,850,578 A | 11/1974 | McConnell |
| 3,850,752 A | 11/1974 | Schuurs |
| 3,853,987 A | 12/1974 | Dreyer |
| 3,867,517 A | 2/1975 | Ling |
| 3,879,262 A | 4/1975 | Schuurs |
| 3,901,654 A | 8/1975 | Gross |
| 3,935,074 A | 1/1976 | Rubenstein |
| 3,984,533 A | 10/1976 | Uzgiris |
| 3,996,345 A | 12/1976 | Ullman |
| 4,034,074 A | 7/1977 | Miles |
| 4,098,876 A | 7/1978 | Piasio |
| 4,666,828 A | 5/1987 | Gusella |
| 4,683,202 A | 7/1987 | Mullis |
| 4,801,531 A | 1/1989 | Frossard |
| 4,879,219 A | 11/1989 | Wands |
| 5,011,771 A | 4/1991 | Bellet |
| 5,192,659 A | 3/1993 | Simons |
| 5,272,057 A | 12/1993 | Smulson |
| 5,281,521 A | 1/1994 | Trojanowski |
| 2006/0148715 A1 | 7/2006 | Tweardy |

FOREIGN PATENT DOCUMENTS

| | | |
|---|---|---|
| WO | 2011130654 | 10/2011 |
| WO | 2014111936 | 7/2014 |

OTHER PUBLICATIONS

Kau et al (Nature Reviews, 2004. vol. 4, pp. 106-117).*
Yoshikawa et al (Journal of Controlled Release, 2004. vol. 96, pp. 227-232).*
Cardarella et al., (2013) Clinical, pathologic, and biologic features associated with BRAF mutations in non-small cell lung cancer. Clinical Cancer Research, 19(16), 4532-4540.
Chiu et al., (2015) Epidermal growth factor receptor tyrosine kinase inhibitor treatment response in advanced lung adenocarcinomas with G719X/L861Q/S768I mutations. Journal of Thoracic Oncology, 10(5), 793-799.
Chong & Jänne, (2013) The quest to overcome resistance to EGFR-targeted therapies in cancer. Nature medicine, 19(11), 1389-1400.
Franke, (2008) PI3K/Akt: getting it right matters. Oncogene, 27(50), 6473-6488.
Kim et al., (2007) Activation of p53-dependent growth suppression in human cells by mutations in PTEN or PIK3CA. Molecular and cellular biology, 27(2), 662-677.
Yang et al., (2010) Activation of FOXO3a is sufficient to reverse mitogen-activated protein/extracellular signal-regulated kinase kinase inhibitor chemoresistance in human cancer. Cancer research, 70(11), 4709-4718.
International Search Report based on International Patent Application No. PCT/IL2015/050746, dated Oct. 21, 2015.
Kau et al., (2003) A chemical genetic screen identifies inhibitors of regulated nuclear export of a Forkhead transcription factor in PTEN-deficient tumor cells. Cancer Cell 4(6): 463-76; 14 pages.
Knauer et al., (2005) Translocation biosensors to study signal-specific nucleo-cytoplasmic transport, protease activity and protein-protein interactions. Traffic 6(7): 594-606; 14 pages.
Zanella et al., (2007) An HTS approach to screen for antagonists of the nuclear export machinery using high content cell-based assays. Assay Drug Dev Technol 5(3): 333-41; 10 pages.

(Continued)

*Primary Examiner* — Celine X Qian
(74) *Attorney, Agent, or Firm* — Cooley LLP

(57) ABSTRACT

Methods for identifying and determining drug response of patient specific oncogenic mutations are provided. The methods provided identify specific (personalized) drug treatment based on the effect of drug on the patient derived markers associated with aberrant signal transduction pathways, in biological samples of a cancer patient.

20 Claims, 16 Drawing Sheets

Specification includes a Sequence Listing.

(56) References Cited

OTHER PUBLICATIONS

Extended European Search Report dated Dec. 18, 2017 issued in corresponding EP Application No. 15824252.9; 10 pages.
Miyake (2006) Soyaku wo Kaeru Toransufekushon (Idenshi Donyu), Arei, Sansoken. Today (2006) 26-27 (English translation of title: "Transfection (gene transfer) array to change drug discovery. Enhance the efficiency of RNA interference to a practical level"). Abstract.
Office Action dated Jul. 16, 2019 issued in corresponding Japanese Patent Application No. 2017-503019 with English translation, 6 pages.

* cited by examiner

Differential subcellular translocation of ERK2 in response to expression of different ERBB2 mutants in the presence of drugs Differential subcellular translocation of ERK2 or STAT3 in response to expression of different EGFR mutants in the presence of drugs Differential subcellular translocation of ERK2 or STAT3 in response to expression of different ERBB2 mutants in the presence of drugs Differential subcellular translocation of P38 or REL-A in response to expression of different PIK3CA mutants in the presence of drugs Differential subcellular translocation of STAT3 in response to expression of different KIT mutants in the presence of drugs Differential subcellular translocation of ERK2 in response to expression of different ERBB2 and BRAF mutants in the presence of drugs or drug combinations Differential subcellular translocation of ERK2 in response to expression of different EGFR and KRAS mutants in the presence of drugs or combinations of drugs

SEQUENCE LISTING

<160> NUMBER OF SEQ ID NOS: 47

<210> SEQ ID NO 1
<211> LENGTH: 20
<212> TYPE: DNA
<213> ORGANISM: Artificial sequence
<220> FEATURE:
<223> OTHER INFORMATION: Primer

<400> SEQUENCE: 1
atgagcgacg tggctattgt                                                   20

<210> SEQ ID NO 2
<211> LENGTH: 18
<212> TYPE: DNA
<213> ORGANISM: Artificial sequence
<220> FEATURE:
<223> OTHER INFORMATION: Primer

<400> SEQUENCE: 2
tcaggccgtg ccgctggc                                                     18

<210> SEQ ID NO 3
<211> LENGTH: 19
<212> TYPE: DNA
<213> ORGANISM: Artificial sequence
<220> FEATURE:
<223> OTHER INFORMATION: Primer

<400> SEQUENCE: 3
atggcggcgc tgagcggtg                                                    19

<210> SEQ ID NO 4
<211> LENGTH: 20
<212> TYPE: DNA
<213> ORGANISM: Artificial sequence
<220> FEATURE:
<223> OTHER INFORMATION: Primer

<400> SEQUENCE: 4
tcagtggaca ggaaacgcac                                                   20

<210> SEQ ID NO 5
<211> LENGTH: 18
<212> TYPE: DNA
<213> ORGANISM: Artificial sequence
<220> FEATURE:
<223> OTHER INFORMATION: Primer

<400> SEQUENCE: 5
atgcgaccct ccgggacg                                                     18

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
tcatgctcca ataaattcac tgct                                              24

<210> SEQ ID NO 7
<211> LENGTH: 23
<212> TYPE: DNA
<213> ORGANISM: Artificial sequence

```
<220> FEATURE:
<223> OTHER INFORMATION: Primer

<400> SEQUENCE: 7
atgacggaat ataagctggt ggt                                           23

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
tcaggagagc acacacttgc                                               20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
atgcccaaga agaagccgac                                               20

<210> SEQ ID NO 10
<211> LENGTH: 19
<212> TYPE: DNA
<213> ORGANISM: Artificial sequence
<220> FEATURE:
<223> OTHER INFORMATION: Primer

<400> SEQUENCE: 10
ttagacgcca gcagcatgg                                                19

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
atgactgagt acaaactggt ggt                                           23

<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12
ttacatcacc acacatggca                                               20

<210> SEQ ID NO 13
<211> LENGTH: 19
<212> TYPE: DNA
<213> ORGANISM: Artificial sequence
<220> FEATURE:
<223> OTHER INFORMATION: Primer

<400> SEQUENCE: 13
atggggactt cccatccgg                                                19
```

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
ttacaggaag ctgtcttcca cc                                          22

<210> SEQ ID NO 15
<211> LENGTH: 20
<212> TYPE: DNA
<213> ORGANISM: Artificial sequence
<220> FEATURE:
<223> OTHER INFORMATION: Primer

<400> SEQUENCE: 15
atgcctccac gaccatcatc                                             20

<210> SEQ ID NO 16
<211> LENGTH: 20
<212> TYPE: DNA
<213> ORGANISM: Artificial sequence
<220> FEATURE:
<223> OTHER INFORMATION: Primer

<400> SEQUENCE: 16
tcagttcaat gcatgctgtt                                             20

<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
atgacagcca tcatcaaaga ga                                          22

<210> SEQ ID NO 18
<211> LENGTH: 25
<212> TYPE: DNA
<213> ORGANISM: Artificial sequence
<220> FEATURE:
<223> OTHER INFORMATION: Primer

<400> SEQUENCE: 18
tcagactttt gtaatttgtg tatgc                                       25

<210> SEQ ID NO 19
<211> LENGTH: 20
<212> TYPE: DNA
<213> ORGANISM: Artificial sequence
<220> FEATURE:
<223> OTHER INFORMATION: Primer

<400> SEQUENCE: 19
atggagcaca tacagggagc                                             20

<210> SEQ ID NO 20
<211> LENGTH: 20
<212> TYPE: DNA
<213> ORGANISM: Artificial sequence
<220> FEATURE:
<223> OTHER INFORMATION: Primer

<400> SEQUENCE: 20
ctagaagaca ggcagcctcg                                                    20

<210> SEQ ID NO 21
<211> LENGTH: 18
<212> TYPE: DNA
<213> ORGANISM: Artificial sequence
<220> FEATURE:
<223> OTHER INFORMATION: Primer

<400> SEQUENCE: 21
atggaggagc cgcagtca                                                      18

<210> SEQ ID NO 22
<211> LENGTH: 20
<212> TYPE: DNA
<213> ORGANISM: Artificial sequence
<220> FEATURE:
<223> OTHER INFORMATION: Primer

<400> SEQUENCE: 22
tcagtctgag tcaggccctt                                                    20

<210> SEQ ID NO 23
<211> LENGTH: 25
<212> TYPE: DNA
<213> ORGANISM: Artificial sequence
<220> FEATURE:
<223> OTHER INFORMATION: Primer

<400> SEQUENCE: 23
atgaatgagg tgtctgtcat caaag                                              25

<210> SEQ ID NO 24
<211> LENGTH: 17
<212> TYPE: DNA
<213> ORGANISM: Artificial sequence
<220> FEATURE:
<223> OTHER INFORMATION: Primer

<400> SEQUENCE: 24
tcactcgcgg atgctgg                                                       17

<210> SEQ ID NO 25
<211> LENGTH: 21
<212> TYPE: DNA
<213> ORGANISM: Artificial sequence
<220> FEATURE:
<223> OTHER INFORMATION: Primer

<400> SEQUENCE: 25
atgagcgatg ttaccattgt g                                                  21

<210> SEQ ID NO 26
<211> LENGTH: 22
<212> TYPE: DNA
<213> ORGANISM: Artificial sequence
<220> FEATURE:
<223> OTHER INFORMATION: Primer

<400> SEQUENCE: 26
ttattctcgt ccacttgcag ag                                                 22

<210> SEQ ID NO 27

```
<211> LENGTH: 18
<212> TYPE: DNA
<213> ORGANISM: Artificial sequence
<220> FEATURE:
<223> OTHER INFORMATION: Primer

<400> SEQUENCE: 27
atgtggagct ggaagtgc                                              18

<210> SEQ ID NO 28
<211> LENGTH: 17
<212> TYPE: DNA
<213> ORGANISM: Artificial sequence
<220> FEATURE:
<223> OTHER INFORMATION: Primer

<400> SEQUENCE: 28
tcagcggcgt ttgagtc                                               17

<210> SEQ ID NO 29
<211> LENGTH: 17
<212> TYPE: DNA
<213> ORGANISM: Artificial sequence
<220> FEATURE:
<223> OTHER INFORMATION: Primer

<400> SEQUENCE: 29
atggtcagct ggggtcg                                               17

<210> SEQ ID NO 30
<211> LENGTH: 25
<212> TYPE: DNA
<213> ORGANISM: Artificial sequence
<220> FEATURE:
<223> OTHER INFORMATION: Primer

<400> SEQUENCE: 30
tcatgtttta acactgccgt ttatg                                      25

<210> SEQ ID NO 31
<211> LENGTH: 27
<212> TYPE: DNA
<213> ORGANISM: Artificial sequence
<220> FEATURE:
<223> OTHER INFORMATION: Primer

<400> SEQUENCE: 31
gcctgctgaa aatgactgaa tataaac                                    27

<210> SEQ ID NO 32
<211> LENGTH: 31
<212> TYPE: DNA
<213> ORGANISM: Artificial sequence
<220> FEATURE:
<223> OTHER INFORMATION: Primer

<400> SEQUENCE: 32
ttacataatt acacactttg tctttgactt c                               31

<210> SEQ ID NO 33
<211> LENGTH: 21
<212> TYPE: DNA
<213> ORGANISM: Artificial sequence
<220> FEATURE:
<223> OTHER INFORMATION: Primer

<400> SEQUENCE: 33
```

```
atgtcgtcca tcttgccatt c                                              21

<210> SEQ ID NO 34
<211> LENGTH: 21
<212> TYPE: DNA
<213> ORGANISM: Artificial sequence
<220> FEATURE:
<223> OTHER INFORMATION: Primer

<400> SEQUENCE: 34
ttatgacatg cttgagcaac g                                              21

<210> SEQ ID NO 35
<211> LENGTH: 16
<212> TYPE: DNA
<213> ORGANISM: Artificial sequence
<220> FEATURE:
<223> OTHER INFORMATION: Primer

<400> SEQUENCE: 35
atggcggcgg cggcgg                                                    16

<210> SEQ ID NO 36
<211> LENGTH: 18
<212> TYPE: DNA
<213> ORGANISM: Artificial sequence
<220> FEATURE:
<223> OTHER INFORMATION: Primer

<400> SEQUENCE: 36
ttaagatctg tatcctgg                                                  18

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
atgaagaccc cggcggacac                                                20

<210> SEQ ID NO 38
<211> LENGTH: 19
<212> TYPE: DNA
<213> ORGANISM: Artificial sequence
<220> FEATURE:
<223> OTHER INFORMATION: Primer

<400> SEQUENCE: 38
tcaggagtct cggtgctcc                                                 19

<210> SEQ ID NO 39
<211> LENGTH: 17
<212> TYPE: DNA
<213> ORGANISM: Artificial sequence
<220> FEATURE:
<223> OTHER INFORMATION: Primer

<400> SEQUENCE: 39
atgagcagaa gcaagcg                                                   17

<210> SEQ ID NO 40
<211> LENGTH: 18
<212> TYPE: DNA
```

```
<213> ORGANISM: Artificial sequence
<220> FEATURE:
<223> OTHER INFORMATION: Primer

<400> SEQUENCE: 40
tcactgctgc acctgtgc                                                    18

<210> SEQ ID NO 41
<211> LENGTH: 20
<212> TYPE: DNA
<213> ORGANISM: Artificial sequence
<220> FEATURE:
<223> OTHER INFORMATION: Primer

<400> SEQUENCE: 41
atggacgaac tgttcccct                                                   20

<210> SEQ ID NO 42
<211> LENGTH: 21
<212> TYPE: DNA
<213> ORGANISM: Artificial sequence
<220> FEATURE:
<223> OTHER INFORMATION: Primer

<400> SEQUENCE: 42
taggagctga tctgactcag c                                                21

<210> SEQ ID NO 43
<211> LENGTH: 14
<212> TYPE: DNA
<213> ORGANISM: Artificial sequence
<220> FEATURE:
<223> OTHER INFORMATION: Primer

<400> SEQUENCE: 43
atgtcgggcc ctcg                                                        14

<210> SEQ ID NO 44
<211> LENGTH: 20
<212> TYPE: DNA
<213> ORGANISM: Artificial sequence
<220> FEATURE:
<223> OTHER INFORMATION: Primer

<400> SEQUENCE: 44
tcactgctca atctccaggc                                                  20

<210> SEQ ID NO 45
<211> LENGTH: 18
<212> TYPE: DNA
<213> ORGANISM: Artificial sequence
<220> FEATURE:
<223> OTHER INFORMATION: Primer

<400> SEQUENCE: 45
atggcccaat ggaatcag                                                    18

<210> SEQ ID NO 46
<211> LENGTH: 18
<212> TYPE: DNA
<213> ORGANISM: Artificial sequence
<220> FEATURE:
<223> OTHER INFORMATION: Primer

<400> SEQUENCE: 46
tcacatgggg gaggtagc                                                    18
```

```
<210> SEQ ID NO 47
<211> LENGTH: 6
<212> TYPE: PRT
<213> ORGANISM: Artificial sequence
<220> FEATURE:
<223> OTHER INFORMATION: Peptide

<400> SEQUENCE: 47

Cys Cys Pro Gly Cys Cys
1               5
```

METHODS FOR DETERMINING DRUG RESPONSE OF PATIENT SPECIFIC MUTATIONS

CROSS REFERENCE TO RELATED APPLICATIONS

The present application is a U.S. National Stage of International Patent Application Serial No. PCT/IL2015/050746, filed Jul. 20, 2015, which claims priority to, and the benefit of U.S. Provisional Patent Application Ser. No. 60/026,715, filed on Jul. 21, 2014, each of which is herein incorporated by reference in its entirety for all purposes.

FIELD OF THE INVENTION

Methods for identifying and determining drug response of patient specific mutations are provided. The methods allow identifying specific (personalized) drug treatment based on the effect of drugs on the identified patient specific mutations.

BACKGROUND OF THE INVENTION

Cancer (malignant tumor or malignant neoplasm), is a group of diseases involving abnormal cell growth with the potential to invade or spread to other parts of the body. Cancer are extremely diverse and various underlying molecular mechanism are involved therewith. Accordingly, clinical therapeutic protocol and prognosis of patients diagnosed with various cancers, may be drastically different depending on accurate diagnosis of underlying molecular mechanism as well as identification of the oncogenic mutations and auto and paracrine effects. In cancer patients, many of the signaling pathways that are involved in control of cell growth and differentiation are regulated in an abnormal fashion, as a result of mutations in key proteins in these pathways.

The complexity and heterogeneity of cancer demands a more sensitive and discerning identification approach that can simulate the tumor signaling pathway and identify patient specific driver mutations. For example, international publication no. WO 2014/111936 to inventors of the current application is directed to methods and systems for identifying patient specific driver mutations. The current state of the art is that only few individual markers can be used to predict treatment efficacy and toxicity. Moreover, the suitability of whole-genome sequencing (next generation sequencing) for selection of targeted therapy is limited due to the large pool of mutations accumulating within the tumor, the limited repertoire of identified driver mutations, and the very limited insight as to the interplay of the various mutations an, in particular, activity thereof.

Thus, there is unmet need in the art for methods and systems that allow identification of specific drug response of patient-specific deriver mutation(s) for determining personalized and optimized drug treatment, which is more efficient, safer and is both cost and time effective, and which has the ability to specifically be adjusted and optimized to the patient specific driver mutations.

SUMMARY OF THE INVENTION

The present invention provides methods and systems for identifying and/or determining an optimized drug treatment, adjusted to accommodate identified patient specific oncogenic mutation. The patient specific oncogenic mutations, are recognized by identifying changes in signaling pathway activity, which is associated with the function of the oncogenic mutation, in a test cell. According to some embodiments, changes in the signaling pathway activity are determined by identifying changes in subcellular localization of a reporter gene, which is associated with the function of the oncogenic mutation. In some embodiments, specific patient derived marker (PDM) genes are obtained (directly or indirectly) from a biological sample, and their effect on the subcellular translocation of a corresponding fluorescent translocation reporter (FTR) gene is tested in viable test cells, to determine whether the tested PDM is mutated. In some embodiments, the specific patient derived marker is obtained and fused to a fluorescent reporter to create a patient derived reporter (PDR), wherein the subcellular translocation of the PDR is tested in viable test cells, to determine whether the tested PDR is mutated. In some embodiments, the identification of the oncogenic mutations allows the testing and determining the response (or susceptibility) of the specific mutation identified, to various drugs and/or combinations of drugs. In some embodiments, the methods disclosed herein allows the identification of an optimized drug treatment which is patient specific and is the most suitable treatment for the conditions associated with the specific patient mutations.

The methods and systems disclosed herein allow the determining or measuring of the ability of drugs to affect (for example, inhibit) the identified aberrant pathways in the presence of the PDM or PDR. The methods disclosed allow the detection/identification of drug response or resistance and determination and/or adjustment of an optimal personalized treatment adapted to the identified patient specific oncogenic mutations.

In some embodiments, the present invention provides methods and systems for identifying patient specific oncogenic mutations involved in cancer and further provides methods for detection or identification of drug response of the identified oncogenic mutations to various drugs or combinations of drugs. In some embodiments, the mutations are oncogenic mutations. In some embodiments, the mutations are driver mutations. In some embodiments, the methods and systems provide a predictive platform to determine the effect of a tested drug or combination of drugs on the patient specific cellular pathways and/or the specific mutation(s). In some embodiments, the methods and systems provide a predictive platform to determine an optimized treatment specifically adjusted to the patient. In some embodiments, the methods disclosed herein enable the identification of auto and paracrine effects on cellular and intercellular signaling pathways. In some embodiments, the methods disclosed herein enable the detection and/or prediction of inherent and acquired drug resistance mechanisms.

According to some embodiments, there is provided a method for identifying/determining drug response/susceptibility to drug treatment of patient specific oncogenic mutations, the method comprising identifying changes in subcellular localization/translocation of a reporter marker gene, whereby the changes in the subcellular localization are affected by the oncogenic mutation, in the presence and/or absence of test drug or combination of drugs. In some embodiments, PDMs are obtained from biological sample of the patient (directly or indirectly, for example, based on sequencing data), and are manipulated (engineered) to be expressed in a viable test cell, in the presence of a reporter chimeric gene (Fluorescence Translocation Reporter (FTR), which includes a chimeric product of a reporter gene portion and a target gene portion). The subcellular localization of the FTR in the test cell is then determined. If the subcellular localization of the FTR in the presence of the tested PDM is different than the subcellular localization of the FTR under normal conditions (i.e. in the presence of a corresponding WT PDM) and/or as compared to other known reference, it is indicative that the tested PDM is mutated. Further, the identified mutation is tested in the presence of a test drug or combination of test drugs to identify a specific drug response (susceptibility to drug treatment) of the tested PDM. Thus, using the methods disclosed herein, the identified oncogenic mutations are further assayed in the presence of a drug to measure the ability of the drug to affect the oncogenic activity thereof. Alternatively or additionally, in some embodiments, a PDM can be tested directly, by creating a PDR (i.e. a PDM linked/attached/fused to a reporter gene), and tracking its subcellular localization, without the use of FTR. Moreover, by determining such oncogenic mutations, the activated signaling pathways operating within the patient tumor can be identified. Further, this enables to precisely and specifically choose the required targeted therapy treatment needed to eradicate the tumor and avoid resistance mechanisms of the specific patient.

According to some embodiments, there is advantageously provided an enhanced and improved diagnostic platform for identifying specific drug response in order to determine optimized, personalized cancer therapy. In some embodiments, the method includes a cell-based assay that is able to identify activating-oncogenic mutations by monitoring their effect on an FTR in live (viable) cells, and effectively identify and determine drug response of the identified mutations to eventually establish a patient specific, personalized, drug treatment. The methods disclosed herein can advantageously indeed predict the resistance and sensitivity of different targeted therapy drugs, with a high degree of significance and can identify drug response and the susceptibility to drug treatment of various patient mutations and further provide drug selection in the case of multiple drugs to the same target. Further, as exemplified herein below, the drug responses identified by the methods disclosed herein are also concordant with the outcome observed in the clinic, providing a mechanistic explanation to the efficiency of these drugs. These results thus exemplify the capabilities of the disclosed methods and systems to identify drug response of various mutations and to provide drug selection in the case of multiple drugs to the same target.

In some embodiments, the methods and systems disclosed herein provide a platform that enables the identification of the profile of the patients tumor activated signaling pathways by monitoring the activation of various signaling proteins (such as, for example, membrane-localized and/or intracellular receptors and signaling proteins), in viable test cells and further determine drug response (susceptibility to drug treatment) to various test drugs or combinations thereof. In some embodiments, the identification of the oncogenic mutations may be performed by detecting intracellular/subcellular translocation events and protein-protein interactions involving FTRs (that is, translocation to/between various subcellular localizations, such as, the plasma membrane, cytosol, endosomes, nucleus, and the like). According to some embodiments, the methods and systems disclosed herein are advantageous as, in addition to identifying multiple mutation events in the same biological sample of the same patient (including not yet identified mutations, and determining the oncogenic activity of such mutations), the also provide ability to determine a drug response of such mutations, that can ultimately allow the determination of personalized treatment regime for the specific patient. Thus, the methods and systems disclosed herein in addition to allowing the identification of cellular events leading to cancer or involved in cancer, can also allow the determination or identification of an effective, optimized, drug treatment specifically suited to the identified cellular events and personally adjusted to the specific patient.

According to some embodiments, upon identification of the patient specific mutations and the signaling pathways involved, targeted therapy drugs/agents (or combinations thereof) known to inhibit/affect the identified pathways/mutations may be incubated with the test cells and the inhibited/reduced/modified oncogenic activity may be tested again, to identify the drugs/agents exhibiting the best effect on the tumor and the patient. In some embodiments, the various drug/agents are not necessarily known to affect the tested mutations. In some embodiments, the various drug/agents treatments and their respective curative ability may be superimposed on the tumor oncogenic map and provide a patient specific underlying molecular tumor mechanism, the treatment options and their respective expected efficacy for treating the specific patient. This may allow a health care provider to decide on optimized treatment options.

According to some embodiments, there is provided a method of detecting drug response or determining susceptibility to drug treatment of one or more patient specific mutations in a biological sample of a cancer patient, comprising the steps of:

a) obtaining a plurality of mRNAs from the biological sample;
b) generating a cDNA library from the plurality of mRNAs;
c) amplifying specific cDNAs of the cDNA library using a set of primers complementary to polynucleotides encoding for known signal transduction proteins;
d) forming individual expression constructs of the amplified cDNAs wherein the cDNAs are operably linked to a promoter;
e) forming an addressable array of a first set of expression constructs harboring the amplified cDNAs from the biological sample, and a second set of expression constructs of the corresponding wild type cDNAs;
f) adding an expression vector encoding for a Fluorescence Translocation Reporter (FTR) gene comprising a target gene portion linked to a specific reporter gene portion for each locus in the array;
g) adding viable assay cells to each locus under conditions enabling transfection of the DNA constructs and vectors into the assay cells;
h) comparing at least one attribute of the expressed FTR in the assay cells expressing the cDNAs from the biological sample with its corresponding wild type expressed cDNAs;
i) repeating step g) in the presence of a drug and comparing at least one attribute of the expressed FTR in the assay cells expressing the cDNAs from the biological sample and/or the corresponding wild type expressed cDNAs in the presence and absence of the drug;
wherein a disparate result between the assay cells expressing the cDNA derived from the biological sample of the cancer patient and the corresponding wild type cDNA, is used for identifying the cDNA from the biological sample as a candidate patient specific driver mutation; and wherein a disparate result between the assay cells expressing the cDNA derived from the biological sample of the cancer patient in the presence and absence of a drug is indicative of a drug response of the candidate patient specific driver mutation.

In some embodiments, the drug is an anti-cancer drug. In some embodiments, the drug is a test drug. In some embodiments, the method comprises adding more than one drug, concomitantly or sequentially. In some embodiments, the method comprises adding a combination of drugs. In some embodiments, the method comprises adding varying concentrations of drug(s), to determine drug response.

In some embodiments, the attribute of the FTR is selected from localization of a fluorescent protein and translocation of a fluorescent protein. In some embodiments, the localization comprises a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton. In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In further embodiments, the reporter gene portion of the FTR encodes for a fluorescent marker. In some embodiments, the fluorescent marker may be selected from: Green Fluorescent Protein (GFP), mCherry, mApple, DsRed, Red Fluorescent Protein (RFP), Blue Fluorescent Protein (BFP), EGFP, CFP, YFP, AmCyan1, ZsGreen1, Zs Yellow 1, DsRed2, AsRed2, and HcRed1.

In some embodiments, the biological sample is selected from tumor cells, tumor biopsy, tumor tissue and bodily fluids.

In some embodiments, the first and/or second sets of expression constructs comprise a double stranded linear DNA. In other embodiments, the promoter of the first and/or second set of expression constructs is an inducible promoter. In some embodiments, the promoter of the first and/or second set of expression constructs is a constitutive promoter.

In some embodiments, the method further comprises inducing expression of the expression construct and/or expression vector in the transfected cells to obtain gene products of the first set of cDNAs from the sample and the FTR for each locus in the array.

In further embodiments the expression constructs of the amplified cDNAs further comprise an IRES and a second reporter gene.

In some embodiments, the method further comprises drying the DNA constructs on a solid support in the presence of a transfection reagent.

In some embodiments, the expression vector of the FTR is a circular expression vector. In further embodiments, the expression vector comprises a constitutive or inducible promoter.

In some embodiments, step g) precedes steps e) and/or f), in which case the assay cells are added to each locus, prior to addition of expression constructs and/or expression vectors.

In some embodiments, the method further comprises drying the DNA constructs on a solid support in the presence of a transfection reagent.

According to some embodiments, there is provided a method of identifying drugs capable of suppressing the effect of one or more patient specific mutations, comprising the steps of:
  a) forming an addressable array of a first set of expression constructs harboring genes comprising one or more patient specific mutations, and a second set of expression constructs of corresponding wild type genes;
  b) adding an expression vector encoding for a Fluorescence Translocation Reporter (FTR) gene comprising a target gene portion linked to a specific reporter gene portion for each locus in the addressable array;
  c) adding viable assay cells to each locus under conditions enabling transfection of the expression constructs and expression vectors into the assay cells; and
  d) comparing at least one attribute of the expressed FTR in the assay cells expressing the genes comprising the one or more patient specific mutations with its corresponding wild type expressed gene in the presence and absence of the drug;

wherein a disparate result between the assay cells expressing the genes comprising the one or more patient specific mutations, and/or the corresponding wild type genes in the absence and presence of a drug is indicative of a drug capable of suppressing the effect of the one or more patient specific mutations.

According to some embodiments, the drug is an anti-cancer drug. In some embodiments, the method includes adding more than one drug, concomitantly or sequentially. In some embodiments, the method includes adding a combination of drugs. In some embodiments, the method includes adding varying concentration of drug(s), to determine the drug response.

In some embodiments, the attribute of the FTR may be selected from localization of a fluorescent protein and translocation of a fluorescent protein. In some embodiments, the localization may include a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In some embodiments, the reporter gene portion of the FTR may encode for a fluorescent marker, such as a fluorescent protein.

In some embodiments, the patient genes may be obtained/derived from a biological sample of the patient. In some embodiments, the biological sample may be selected from tumor cells, tumor biopsy, tumor tissue and bodily fluids, microenvironment extract, extracellular fluid, secreted fluid from tumor. In some embodiments, the patient is cancer patient. In some embodiments, the mutation is an oncogenic mutation.

In some embodiments, the first and/or second set of expression constructs harbors a portion of a gene. In some embodiments, the method the first and/or second sets of expression constructs include a double stranded linear DNA. In some embodiments, the promoter of the first and/or second set of expression constructs may be an inducible or a constitutive promoter. In some embodiments, the method further includes drying the expression constructs on a solid support in the presence of a transfection reagent. In some embodiments, step c) may precede step a) and/or step b), in which case the assay cells are added to the addressable array prior to addition of the expression constructs and/or the expression vectors.

According to some embodiments, there is provided a method of identifying susceptibility to drug treatment of one or more patient specific mutations, comprising the steps of:

a) forming an addressable array of a first set of expression constructs harboring genes comprising the one or more patient specific patient specific mutations, and a second set of expression constructs of corresponding wild type genes; b) adding an expression vector encoding for a Fluorescence Translocation Reporter (FTR) gene comprising a target gene portion linked to a specific reporter gene portion for each locus in the addressable array; c) adding viable assay cells to each locus under conditions enabling transfection of the expression constructs and expression vectors into the assay cells; and d) comparing at least one attribute of the expressed FTR in the assay cells expressing the genes comprising the one or more patient specific mutations with its corresponding wild type expressed gene in the presence and absence of the drug; wherein a disparate result between the assay cells expressing the genes comprising one or more patient specific the mutations, and/or the corresponding wild type genes, in the absence and/or presence of a drug, is indicative of the susceptibility to treatment of the patient specific mutations, with the drug.

According to some embodiments, there is provided a method of detecting drug response of one or more patient specific oncogenic mutations of a cancer patient, comprising the steps of:

a) adding viable assay cells to a substrate in an addressable array, under conditions enabling transfection of expression constructs and expression vectors into the assay cells;

b) adding to the assay cells an expression vector of a Fluorescence Translocation Reporter (FTR) gene comprising a target gene portion linked to a specific reporter gene portion for each locus in the array;

c) adding to the assay cells, at specific locuses of the addressable array, a first set of expression constructs harboring gene(s) comprising patient specific mutation (s), and adding to the assay cells, at specific locuses a second set of expression constructs of corresponding wild type genes, wherein the first set of expression constructs and the second sets of expression constructs are not added to a common locus; and d) comparing at least one attribute of the expressed FTR in the assay cells expressing the mutation(s) with its corresponding wild type expressed gene in the presence and absence of the drug;

wherein a disparate result between the assay cells expressing the gene(s) harboring the mutation(s), and/or the corresponding wild type genes, in the presence and absence of a drug, is indicative of a drug response of the patient specific oncogenic mutation.

According to some embodiments, the drug is an anti-cancer drug. In some embodiments, the method includes adding more than one drug, concomitantly or sequentially. In some embodiments, the method includes adding a combination of drugs. In some embodiments, the method includes adding varying concentration of drug(s), to determine the drug response.

In some embodiments, the attribute of the FTR may be selected from localization of a fluorescent protein and translocation of a fluorescent protein. In some embodiments, the localization may include a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In some embodiments, the reporter gene portion of the FTR may encode for a fluorescent marker, such as a fluorescent protein.

In some embodiments, the patient genes may be obtained/derived from a biological sample of the patient. In some embodiments, the biological sample may be selected from tumor cells, tumor biopsy, tumor tissue and bodily fluids, microenvironment extract, extracellular fluid, secreted fluid from tumor. In some embodiments, the patient is cancer patient. In some embodiments, the mutation is an oncogenic mutation.

In some embodiments, the first and/or second set of expression constructs harbors a portion of a gene. In some embodiments, the method the first and/or second sets of expression constructs include a double stranded linear DNA. In some embodiments, the promoter of the first and/or second set of expression constructs may be an inducible or a constitutive promoter. In some embodiments, the method further includes drying the expression constructs on a solid support in the presence of a transfection reagent. In some embodiments, step b) and/or step c) may precede step a).

According to some embodiments, the expression constructs may be obtained by a process comprising one or more of the following steps: i) generating a cDNA library from a plurality of mRNAs obtained from the biological sample of the patient; ii) amplifying specific cDNAs of the cDNA library using a set of primers complementary to polynucleotides encoding for genes suspected of harboring an oncogenic mutation; and iii) operably linking the amplified cDNAs to a promoter.

In some embodiments, the patients genes or gene portions, suspected of harboring one or more mutations, may be synthesized by methods known in the art and optionally be operably linked to a promoter to obtain the expression constructs. In some embodiments, the patient genes (or portions thereof) and/or the corresponding wild-type genes may be artificially synthesized, based on their sequence and further processed to generate the corresponding PDMs.

According to some embodiments, there is further provided a kit for identifying patient specific mutations and drug response thereof.

DESCRIPTION OF THE TEXT FILE SUBMITTED ELECTRONICALLY

The contents of the text file submitted electronically are incorporated herein by reference in their entirety: A computer readable format copy of the Sequence Listing (filename: NODX-001-01US_PCT_SEQ_LIST_ST25.txt, date recorded: Jan. 16, 2017, file size 9 kilobytes).

BRIEF DESCRIPTION OF THE DRAWINGS

FIG. 3B—A schematic representation of the signaling pathways involved with the identified mutation presented in FIG. 3A, and the site of inhibition of the test drug (Neratinib).

FIG. 4B—A schematic representation of the signaling pathways involved with the identified mutation presented in FIG. 4A, and the site of inhibition of the test drug (Regorafenib).

FIG. 5B—A bar graph showing the results of a cell based assay in which the genes encoding for EGFR in wild type form (EGFR WT) or triple mutant form (EGFR triple mutant, G719A, T790M and L861Q) have been expressed in test cells, along with a reporter protein (FTR, ERK2-GFP). The cells were either untreated or treated with the EGFR inhibitors Afatinib. Cells were fixed (30 hours later) and imaged, and the nuclear to cytoplasmic ratio (N:C) under the various experimental conditions was calculated using automated image analysis.

FIG. 6B—A graph showing the results of a cell based assay in which the genes encoding for BRAF in mutant forms (BRAF V600K, BRAF V600E, BRAF G469V) have been expressed in test cells, along with a reporter protein (FTR ERK2-GFP). The cells were either untreated (UT) or treated with the BRAF inhibitor Vemurafenib. Cells were fixed (24 hours later) and imaged, and the difference in ratio between the intensity of the FTR in the nucleus (N) and cytoplasm (C) was measured (Delta N:C ratio).

FIG. 6C—A graph showing the results of a cell based assay in which the genes encoding for BRAF in mutant forms (BRAF V600K, BRAF V600E, BRAF G469V) have been expressed in test cells, along with a reporter protein (FTR ERK2-GFP). The cells were either untreated (UT) or treated with the BRAF inhibitor Regorafenib. Cells were fixed (24 hours later) and imaged, and the difference in ratio between the intensity of the FTR in the nucleus (N) and cytoplasm (C) was measured (Delta N:C ratio).

FIG. 6D—A graph showing the results of a cell based assay in which the genes encoding for BRAF in mutant forms (BRAF V600K, BRAF V600E, BRAF G469V) have been expressed in test cells, along with a reporter protein (FTR ERK2-GFP). The cells were either untreated (UT) or treated with the MEK1/2 inhibitor Selumetinib. Cells were fixed (24 hours later) and imaged, and the difference in ratio between the intensity of the FTR in the nucleus (N) and cytoplasm (C) was measured (Delta N:C ratio).

FIG. 6E—A bar graph showing the results of a cell based assay in which the genes encoding for BRAF in mutant forms (BRAF V600K, BRAF V600E, BRAF G469V) have been expressed in test cells, along with a reporter protein (FTR ERK2-GFP). The cells were either untreated (UT) or treated with the BRAF inhibitor Vemurafenib, MEK1/2 inhibitor Selumetinib or a combination of both inhibitors. Cells were fixed (24 hours later) and imaged, and the difference in ratio between the intensity of the FTR in the nucleus (N) and cytoplasm (C) was measured (Delta N:C ratio).

FIG. 6F—A bar graph showing the results of a cell based assay in which the genes encoding for BRAF in mutant forms (BRAF V600K, BRAF V600E, BRAF G469V) have been expressed in test cells, along with a reporter protein (FTR ERK2-GFP). The cells were either untreated (UT) or treated with the BRAF inhibitors Vemurafenib or Regorafenib or a combination of both inhibitors. Cells were fixed (24 hours later) and imaged, and the difference in ratio between the intensity of the FTR in the nucleus (N) and cytoplasm (C) was measured (Delta N:C ratio).

FIG. 7B—A graph showing the results of a cell based assay in which the genes encoding for EGFR in mutant forms (EGFR L858R, EGFR L858R/T790M) have been expressed in test cells, along with a reporter protein (FTR ERK2-GFP). The cells were either untreated (UT) or treated with the EGFR inhibitor Afatinib. Cells were fixed (24 hours later) and imaged, and the difference in ratio between the intensity of the FTR in the nucleus (N) and cytoplasm (C) was measured (Delta N:C ratio).

FIG. 7C—A graph showing the results of a cell based assay in which the genes encoding for EGFR in mutant forms (EGFR L858R, EGFR L861Q) have been expressed in test cells, along with a reporter protein (FTR ERK2-GFP). The cells were either untreated (UT) or treated with the MEK1/2 inhibitor Selumetinib. Cells were fixed (24 hours later) and imaged, and the difference in ratio between the intensity of the FTR in the nucleus (N) and cytoplasm (C) was measured (Delta N:C ratio).

FIG. 7D—A graph showing the results of a cell based assay in which the genes encoding for EGFR in mutant forms (EGFR L858R, EGFR L861Q, EGFR T790M) have been expressed in test cells, along with a reporter protein (FTR STAT3-GFP). The cells were either untreated (UT) or treated with the MEK1/2 inhibitor Selumetinib. Cells were fixed (24 hours later) and imaged, and the difference in ratio between the intensity of the FTR in the nucleus (N) and cytoplasm (C) was measured (Delta N:C ratio).

FIG. 7E—A bar graph showing the results of a cell based assay in which the genes encoding for EGFR in mutant forms (EGFR L858R, EGFR G719S/T790M/L861Q) have been expressed in test cells, along with a reporter protein (FTR ERK2-GFP). The cells were either untreated (UT) or treated with the EGFR inhibitor Afatinib, MEK1/2 inhibitor Selumetinib or a combination of both inhibitors. Cells were fixed (24 hours later) and imaged, and the difference in ratio between the intensity of the FTR in the nucleus (N) and cytoplasm (C) was measured (Delta N:C ratio).

FIG. 7F—A bar graph showing the results of a cell based assay in which the genes encoding for EGFR in mutant forms (EGFR T790M, L858R, EGFR G719S/T790M/L861Q) have been expressed in test cells, along with a reporter protein (FTR ERK2-GFP). The cells were either untreated (UT) or treated with the EGFR inhibitor Afatinib, BRAF inhibitor Regorafenib or a combination of both inhibitors. Cells were fixed (24 hours later) and imaged, and the difference in ratio between the intensity of the FTR in the nucleus (N) and cytoplasm (C) was measured (Delta N:C ratio).

FIG. 8B—A graph showing the results of a cell based assay in which the genes encoding for ERBB2 in mutant forms (ERBB2 V777L, ERBB2 S310F) have been expressed in test cells, along with a reporter protein (FTR STAT3-GFP). The cells were either untreated (UT) or treated with the ERBB2 inhibitor Neratinib. Cells were fixed (24 hours later) and imaged, and the difference in ratio between the intensity of the FTR in the nucleus (N) and cytoplasm (C) was measured (Delta N:C ratio).

FIG. 8C—A graph showing the results of a cell based assay in which the genes encoding for ERBB2 in mutant forms (ERBB2 V777L, ERBB2 S310F) have been expressed in test cells, along with a reporter protein (FTR STAT3-GFP). The cells were either untreated (UT) or treated with the ERBB2 inhibitor Lapatinib. Cells were fixed (24 hours later) and imaged, and the difference in ratio between the intensity of the FTR in the nucleus (N) and cytoplasm (C) was measured (Delta N:C ratio).

FIG. 8D—A graph showing the results of a cell based assay in which the genes encoding for ERBB2 in mutant forms (ERBB2 V842I, ERBB2 S310F) have been expressed in test cells, along with a reporter protein (FTR ERK2-GFP). The cells were either untreated (UT) or treated with the MEK1/2 inhibitor Selumetinib. Cells were fixed (2 hours later) and imaged, and the difference in ratio between the intensity of the FTR in the nucleus (N) and cytoplasm (C) was measured (Delta N:C ratio).

FIG. 8E—A bar graph showing the results of a cell based assay in which the genes encoding for ERBB2 in mutant forms (ERBB2 V842I, ERBB2 V777L, ERBB2 S310F) have been expressed in test cells, along with a reporter protein (FTR ERK2-GFP). The cells were either untreated (UT) or treated with the ERBB2 inhibitor Neratinib, MEK1/2 inhibitor Selumetinib or a combination of both inhibitors. Cells were fixed (24 hours later) and imaged, and the difference in ratio between the intensity of the FTR in the nucleus (N) and cytoplasm (C) was measured (Delta N:C ratio).

FIG. 8F—A bar graph showing the results of a cell based assay in which the genes encoding for ERBB2 in mutant forms (ERBB2 V842I, ERBB2 S310F) have been expressed in test cells, along with a reporter protein (FTR STAT3-GFP). The cells were either untreated (UT) or treated with the ERBB2 inhibitor Neratinib, MEK1/2 inhibitor Selumetinib or a combination of both inhibitors. Cells were fixed (24 hours later) and imaged, and the difference in ratio between the intensity of the FTR in the nucleus (N) and cytoplasm (C) was measured (Delta N:C ratio).

FIG. 9B—A graph showing the results of a cell based assay in which the genes encoding for PIK3CA in mutant forms (PIK3CA V344A, PIK3CA Q546L, PIK3CA N345K) have been expressed in test cells, along with a reporter protein (FTR REL-A-GFP). The cells were either untreated (UT) or treated with the PIK3CA inhibitor Idelalisib. Cells were fixed (24 hours later) and imaged, and the difference in ratio between the intensity of the FTR in the nucleus (N) and cytoplasm (C) was measured (Delta N:C ratio).

FIG. 9C—A graph showing the results of a cell based assay in which the genes encoding for PIK3CA in mutant forms (PIK3CA V344A, PIK3CA H1047R, PIK3CA N345K) have been expressed in test cells, along with a reporter protein (FTR P38-GFP). The cells were either untreated (UT) or treated with the PIK3CA inhibitor IdelalisibEverolimus. Cells were fixed (24 hours later) and imaged, and the difference in ratio between the intensity of the FTR in the nucleus (N) and cytoplasm (C) was measured (Delta N:C ratio).

FIG. 9D—A graph showing the results of a cell based assay in which the genes encoding for PIK3CA in mutant forms (PIK3CA N345K, PIK3CA H1047R) have been expressed in test cells, along with a reporter protein (FTR P38-GFP). The cells were either untreated (UT) or treated with the PIK3CA inhibitor Buparilisib. Cells were fixed (24 hours later) and imaged, and the difference in ratio between the intensity of the FTR in the nucleus (N) and cytoplasm (C) was measured (Delta N:C ratio).

FIG. 9E—A bar graph showing the results of a cell based assay in which the genes encoding for PIK3CA in mutant forms (PIK3CA N345K, PIK3CA H1047R) have been expressed in test cells, along with a reporter protein (FTR P38-GFP). The cells were either untreated (UT) or treated with the PIK3CA inhibitor Temsirolimus. Cells were fixed (24 hours later) and imaged, and the difference in ratio between the intensity of the FTR in the nucleus (N) and cytoplasm (C) was measured (Delta N:C ratio).

FIG. 9F—A bar graph showing the results of a cell based assay in which the genes encoding for PIK3CA in mutant forms (PIK3CA N344A, PIK3CA N345K, PIK3CA H1047R) have been expressed in test cells, along with a reporter protein (FTR P38-GFP). The cells were either untreated (UT) or treated with the PIK3CA inhibitors Idelalisib, Everolimus or a combination of both inhibitors. Cells were fixed (24 hours later) and imaged, and the difference in ratio between the intensity of the FTR in the nucleus (N) and cytoplasm (C) was measured (Delta N:C ratio).

FIG. 10B—A graph showing the results of a cell based assay in which the genes encoding for cKIT in mutant form (cKIT W557-K558del) have been expressed in test cells, along with a reporter protein (FTR STAT3-GFP). The cells were either untreated (UT) or treated with the cKIT inhibitor Imatinib. Cells were fixed (24 hours later) and imaged, and the difference in ratio between the intensity of the FTR in the nucleus (N) and cytoplasm (C) was measured (Delta N:C ratio).

FIG. 10C—A graph showing the results of a cell based assay in which the genes encoding for cKIT in mutant form (cKIT W557-K558del) have been expressed in test cells, along with a reporter protein (FTR STAT3-GFP). The cells were either untreated (UT) or treated with the cKIT inhibitor Imatinib, MEK1/2 inhibitor Selumetinib or a combination of both inhibitors. Cells were fixed (24 hours later) and imaged, and the difference in ratio between the intensity of the FTR in the nucleus (N) and cytoplasm (C) was measured (Delta N:C ratio).

FIG. 11B—A bar graph showing the results of a cell based assay in which the genes encoding for ERBB2 in mutant form (ERBB2 V777L, ERBB2 L755S) or BRAF in mutant form (BRAF V600E, BRAF V600K) have been expressed in test cells, along with a reporter protein (FTR ERK2-GFP). The cells were either untreated (UT) or treated with the ERBB2 inhibitor Neratinib, BRAF inhibitor Vemurafenib or a combination of both inhibitors. Cells were fixed (24 hours later) and imaged, and the difference in ratio between the intensity of the FTR in the nucleus (N) and cytoplasm (C) was measured (Delta N:C ratio).

FIG. 12B—A bar graph showing the results of a cell based assay in which the genes encoding for EGFR in mutant form (EGFR L858R, EGFR T790M) or KRAS in mutant form (KRAS G12R) have been expressed in test cells, along with a reporter protein (FTR ERK2-GFP). The cells were either untreated (UT) or treated with the EGFR inhibitor Afatinib, MEK1/2 inhibitor Selumetinib or a combination of both inhibitors. Cells were fixed (24 hours later) and imaged, and the difference in ratio between the intensity of the FTR in the nucleus (N) and cytoplasm (C) was measured (Delta N:C ratio).

DETAILED DESCRIPTION OF THE INVENTION

Figure 1:
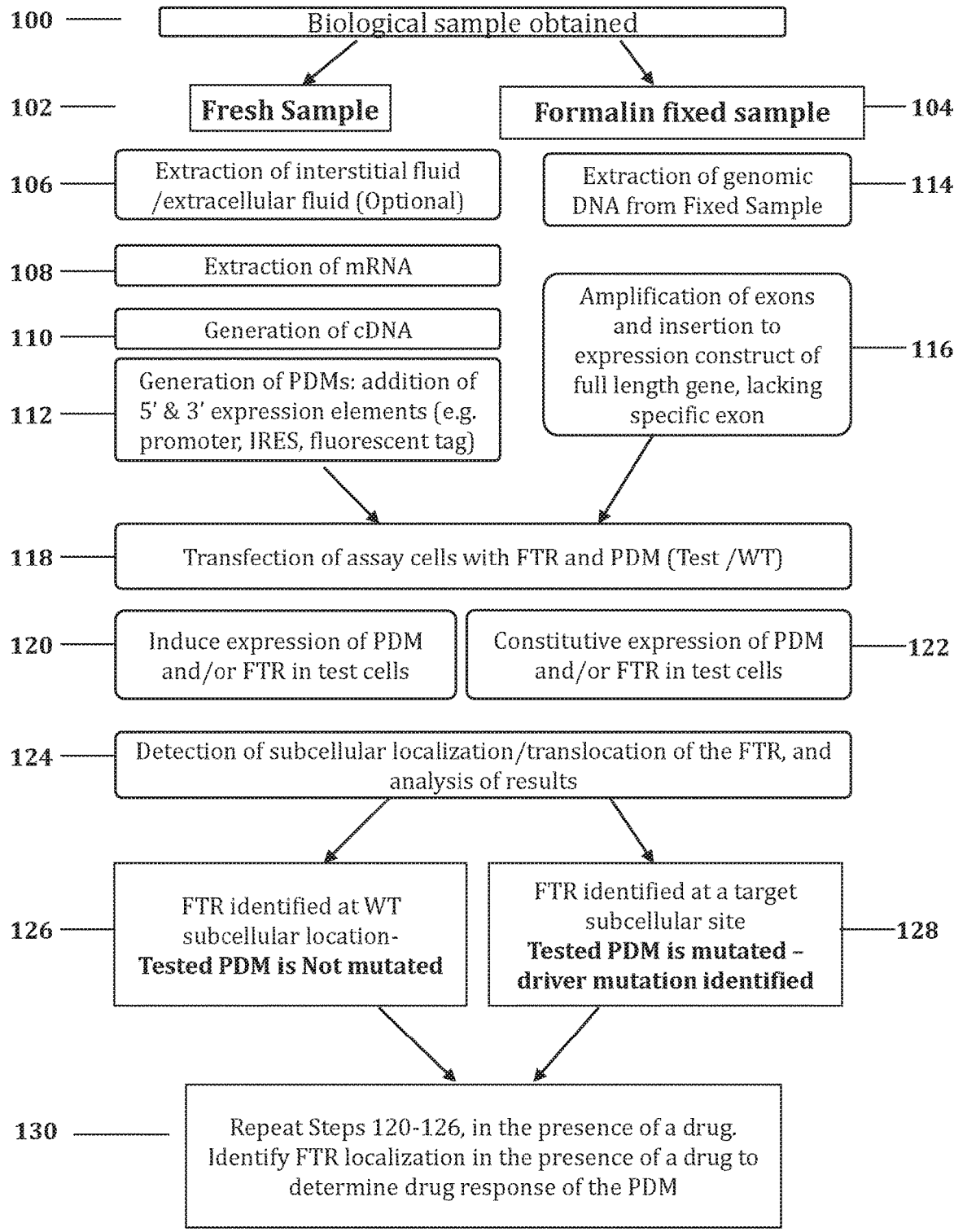
FIG. 1 is a schematic block diagram of steps of a method for identification of patient driver mutations and detection of drug response thereof, according to some embodiments.

According to some embodiments, there is provided a method for identifying or detecting drug response (susceptibility to treatment) of patient specific oncogenic mutations, by identifying changes in signaling pathway activity, which are associated with the function of the driver mutation. In some embodiments, the changes in the signaling pathway activity in the presence and/or absence of a test drug (or combinations of drugs) are determined by identifying changes in subcellular localization of a reporter gene, whereby the changes in the subcellular localization of the reporter gene are affected by the driver mutation. In some embodiments, patient derived markers (PDMs) are obtained from biological sample of the patient, and are manipulated (engineered) to be expressed in a test cell, in the presence of a reporter chimeric gene (FTR). In some embodiments, patient derived markers (PDMs) may be obtained by artificially generating (synthesizing) the corresponding patient genes(s), based on their identified sequence and further manipulating those to be expressed in a test cell. In some embodiments, additionally or alternatively, the patient specific marker is fused to the fluorescent reporter to create a patient derived reporter (PDR). The subcellular localization of the FTR (and/or PDR, if applicable) in the test cell is then determined. If the subcellular localization of the FTR in the presence of the tested PDM (and/or the PDR, if applicable) is different than the subcellular localization of the FTR (and/or PDR, if applicable) under normal conditions (i.e. in the presence of a corresponding WT PDM) or as compared to other predetermined reference, it is indicative that the tested PDM (or PDR) is mutated. Further, the method advantageously allows for precise identification or detection of drug response of the identified PDM (and/or PDR, if applicable), f the subcellular localization of the identified mutated PDM (and/or PDR, if applicable) is different if the assay is performed in the presence of a test drug (or a combination of drugs). Thus, using the methods disclosed herein, patient specific PDMs can be identified/characterized as being oncogenic mutations and further, their precise and accurate drug response (susceptibility) to various test drugs and/or combination of such test drugs can be determined. Moreover, by determining such oncogenic mutations, the activated signaling pathways operating within the patient tumor and the drugs response thereof can be identified. This enables to precisely and specifically choose the required targeted therapy treatment needed to eradicate the tumor and avoid resistance mechanisms of the specific patient.

In some embodiments, the invention is based on the notion that proteins involved in cancer signaling pathways translocate in response to various factors, thereby, by testing the localization of chimeric reporter genes, that are affected by such signaling pathways, in the presence and/or absence of test drug(s) patient specific oncogenic mutations can be identified and their drug response can be identified. According to some embodiments, the methods and systems disclosed herein are advantageous since although there is a vast amount of information regarding oncogenic mutations, the robust methods and systems for identifying multiple mutation events in the same biological sample of the same patient, in addition to yet unidentified mutations, and determination of their drug response are not previously available. For example, in currently used methods of treatment, gastrointestinal stromal tumor patients harboring cKit mutations, are treated with Gleevec. However, common resistance mechanisms occur through secondary mutations within cKit itself or in downstream pathways, rendering such treatment ineffective. Likewise, lung cancer patients that have an EGFR oncogenic mutation are eligible for targeted therapy treatment, but there are several such drugs available. Thus, the methods disclosed herein allow the detection and identification of the response of the identified mutations to various test drug(s), to eventually determine a personalized and optimized drug treatment to the specific patient, while taking into account the specific mutations involved.

In some embodiments, the methods and systems disclosed herein enable the emulation of the patient tumor to identify activated signaling pathways and oncogenic activity and moreover determine tumor susceptibility to anti-cancer therapy. In some embodiments, this is performed by incubating the transfected test cells with one or more test drugs.

As referred to herein, the terms "polynucleotide molecules", "oligonucleotide", "polynucleotide", "nucleic acid" and "nucleotide" sequences may interchangeably be used. The terms are directed to polymers of deoxyribonucleotides (DNA), ribonucleotides (RNA), and modified forms thereof in the form of a separate fragment or as a component of a larger construct, linear or branched, single stranded, double stranded, triple stranded, or hybrids thereof. The term also encompasses RNA/DNA hybrids. The polynucleotides may include sense and antisense oligonucleotide or polynucleotide sequences of DNA or RNA. The DNA or RNA molecules may be, for example, but not limited to: complementary DNA (cDNA), genomic DNA, synthesized DNA, recombinant DNA, or a hybrid thereof or an RNA molecule such as, for example, mRNA, shRNA, siRNA, miRNA, and the like. Accordingly, as used herein, the terms "polynucleotide molecules", "oligonucleotide", "polynucleotide", "nucleic acid" and "nucleotide" sequences are meant to refer to both DNA and RNA molecules. The terms further include oligonucleotides composed of naturally occurring bases, sugars, and covalent inter nucleoside linkages, as well as oligonucleotides having non-naturally occurring portions, which function similarly to respective naturally occurring portions.

The term "construct", as used herein refers to an artificially assembled or isolated nucleic acid molecule which may include one or more nucleic acid sequences, wherein the nucleic acid sequences may include coding sequences (that is, sequence which encodes for an end product), regulatory sequences, non-coding sequences, or any combination thereof. The term construct includes, for example, vectors but should not be seen as being limited thereto.

The term "Expression vector" refers to vectors that have the ability to incorporate and express heterologous nucleic acid fragments (such as DNA) in a target cell. In other words, an expression vector comprises nucleic acid sequences/fragments capable of being transcribed. Many viral, prokaryotic and eukaryotic expression vectors are known and/or commercially available. Selection of appropriate expression vectors is within the knowledge of those having skill in the art.

The terms "Upstream" and "Downstream", as used herein refers to a relative position in a nucleotide sequence, such as, for example, a DNA sequence or an RNA sequence. As well known, a nucleotide sequence has a 5' end and a 3' end, so called for the carbons on the sugar (deoxyribose or ribose) ring of the nucleotide backbone. Hence, relative to the position on the nucleotide sequence, the term downstream relates to the region towards the 3' end of the sequence. The term upstream relates to the region towards the 5' end of the strand.

The terms "promoter element", "promoter" or "promoter sequence" as used herein, refer to a nucleotide sequence that is generally located at the 5' end (that is, precedes, located upstream) of the coding sequence and functions as a switch, activating the expression of a coding sequence. If the coding sequence is activated, it is said to be transcribed. Transcription generally involves the synthesis of an RNA molecule (such as, for example, an mRNA) from a coding sequence. The promoter, therefore, serves as a transcriptional regulatory element and also provides a site for initiation of transcription of the coding sequence into mRNA. Promoters may be derived in their entirety from a native source, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions, or at various expression levels. Promoters which cause a gene to be expressed in most cell types at most times are commonly referred to as "constitutive promoters". Promoters that derive gene expression in a specific tissue are called "tissue specific promoters".

As used herein, the terms "introducing" and "transfection" may interchangeably be used and refer to the transfer or introduction of molecules, such as, for example, nucleic acids, polynucleotide molecules, vectors, and the like into a target cell(s), and more specifically into the interior of a membrane-enclosed space of a target cell(s), such as the cytosol of a cell, the nucleus of a cell, an interior space of a mitochondria, endoplasmic reticulum (ER), and the like. The molecules can be "introduced" into the target cell(s) by any means known to those of skill in the art, for example as taught by Sambrook et al. Molecular Cloning: A Laboratory Manual, Cold Spring Harbor Laboratory Press, New York (2001), the contents of which are incorporated by reference herein. Means of "introducing" molecules into a cell include, for example, but are not limited to: heat shock, calcium phosphate transfection, PEI transfection, electroporation, lipofection, transfection reagent(s), viral-mediated transfer, and the like, or combinations thereof. In some embodiments, the introduced nucleic acid may be, for example, a modified nucleic acid that may be in the form of DNA, RNA. In some embodiments, the nucleic acid is dehydrated prior to being transfected to a cell. In some embodiments, the nucleic acid is incorporated into a vector, such as, for example, an expression vector. Each possibility represents a separate embodiment of the present invention.

The term "expression", as used herein, refers to the production of a desired end-product molecule in a target cell. The end-product molecule may include, for example an RNA molecule; a peptide or a protein; and the like; or combinations thereof.

As referred to herein, the term "patient" is directed to a subject having, suspected of having or diagnosed with a disease. In some embodiments, the term patient is directed to a subject having, suspected of having, or diagnosed with cancer. In some embodiments, a patient is eligible for tumor biopsy.

As referred to herein, the term "biological sample" is directed to include any appropriate body-derived sample. The sample may include fluid samples such as whole blood, peripheral blood monocytes, leukocytes, bone marrow. The samples may include various cells and tissues. The sample may include biopsies. The sample may include fixed and/or embedded tissue sections. The samples may be either freshly extracted or frozen. In another embodiment, the sample is a blood sample. In another embodiment, the sample is a bone marrow sample. In another embodiment, methods for isolating and maintaining a sample comprising blood cells from a subject are known to one of average skill in the art. In some embodiments, a sample comprising polynucleotides, polypeptides, peptides, antibodies fragments and derivatives thereof may comprise a bodily fluid; a soluble fraction of a cell preparation, or media in which cells were grown; a chromosome, an organelle, or membrane isolated or extracted from a cell; genomic DNA, RNA, or cDNA, polypeptides, or peptides in solution or bound to a substrate; a cell; a tissue; a tissue print; a fingerprint, skin or hair; fragments and derivatives thereof. In some embodiments, the biological sample is obtained from a tumor.

As referred to herein, the terms "Patient Derived Marker" ("PDM"), and "subject PDM" are directed to a gene or gene product (or portions thereof) that is isolated or obtained or derived (directly or indirectly) from a biological sample of the subject and its activity in a functional assay is determined. In some embodiments, to the PDM nucleic acid sequence, (which is directly obtained from the biological sample (for example, by generation of a cDNA), or is artificially synthesized (i.e., indirectly obtained)), 5' and/or 3' regulatory elements and/or additional reporter genes are added. In some examples, a PDM as used herein comprises a chimeric nucleic acid sequence molecule comprising a regulatory element (promoter)-the PDM sequence-regulatory element (IRES)-reporter gene not necessarily in this order. Thus, when such a nucleic acid molecule is introduced and expressed in a target cell, the PDM gene product (protein) and the reporter gene product (protein) are expressed in the cell. Additionally or alternatively, an IRES sequence can be omitted and a chimeric protein comprising the PDM gene product and the reporter gene product is expressed in the cell. The thus formed chimeric protein is referred to herein as "Patient Derived Reporter" ("PDR"), or "subject PDR". In some embodiments, the terms "control PDM", "wild type PDM", "corresponding PDM" and "corresponding wild type PDM" are directed to a wild type gene corresponding to the PDM gene (i.e. a non-mutated, fully active), that is used as control. In some embodiments, the wild type PDM is not derived from a biological sample of the patient. The control PDM is used to compare the activity of the subject PDM and the wild type (wt) PDM.

As referred to herein, the term "Fluorescence Translocation Reporter" ("FTR") is directed to a chimeric reporter gene and the corresponding gene product. The chimeric FTR comprising a reporter gene portion (such as a fluorescent marker (protein)) linked to a predetermined target (marker) gene portion (such as, for example, a cell signaling protein, kinase, enzyme, and the like), whereby at least one attribute of the target (marker) gene may be affected (directly or indirectly) by the tested PDM.

As referred to herein, the terms "test cell", "target cell" and "assay cell" may interchangeably be used. The terms are directed to an assay cell which is transfected with a poly nucleic acid molecule such as PDM and/or PDR and/or FTR and/or any of control genes, as described herein. In some embodiments, the test cell is an eukaryotic cell. In some embodiments, the test cell may be a primary cell or a cell line. In another embodiment, an assay cell is a non-cancerous cell. In another embodiment, an assay cell is derived from a cell line. In another embodiment, an assay cell is responsive to at least one cancer-secreted growth factor. In another embodiment, an assay cell is amenable by transfection. In another embodiment, an assay cell is amenable by transient transfection. In another embodiment, an assay cell is a cell, in which the expression of one or more endogenous genes have been reduced or eliminated by any molecular method. In another embodiment, an assay cell is HeLa cell. In another embodiment, an assay cell is HEK 293 cell. In another embodiment, an assay cell is PC12 cell. In another embodiment, an assay cell is U2OS cell. In another embodiment, an assay cell is NCI60 cell lines, such as, A549, EKVX, T47D, HT29. In some embodiments, the assay cell is a cell derived from the patient. In some embodiments, the assay cell is a cell derived from a cancer patient.

As used herein, the terms "subcellular localization", "subcellular region" and "subcellular compartment" refer to any defined part of a cell that may be distinguished by various means (such as, for example, by visual means) from other regions of the cell. In some examples, a subcellular region may be a restricted area within a cell. In some embodiments, a subcellular region may include an organelle. Non limiting examples of subcellular localization include, for example, but not limited to: nucleus, nucleolus, cytosol, mitochondria, endoplasmic reticulum (ER), chloroplasts, membranes, dendritic spines, Golgi apparatus, lysosomes, peroxisomes, endosomal compartments, cytoskeleton, and the like. Each possibility is a separate embodiment. In some embodiments, the term "subcellular translocation" refers to a detected change in the subcellular localization of a reporter gene (such as, FTR or PDR) under various conditions. For example, translocation may be to/from the nucleus from/to the cytosol.

As referred to herein, the terms "drug" and "test drug" may interchangeably be used. The term drug is directed to any compound, substance, molecule, agent and/or reagent that has an effect in treating a condition. In some embodiments, the drug is an anti-cancer drug. In some embodiments, the term drug may encompass more than one drug. In some embodiments, the term drug includes a combination of drugs. In some embodiments the drug is an inhibitor of a cellular protein.

As referred to herein, the terms "drug response" and "susceptibility to drug" may interchangeably be used. The terms refer to a response or effect elicited by a test drug. In some embodiments, the terms relate to the capability of the drug(s) to suppress the effect of a mutation, such as, an oncogenic mutation.

In some embodiments, the terms "Treating a disease" or "treating a condition" are directed to administering of one or more compounds, effective to ameliorate symptoms associated with a disease, to lessen the severity or cure the disease, or to prevent the disease from occurring.

The terms "Detection, "Diagnosis" refer to methods of detection of a disease, symptom, disorder, pathological or normal condition; classifying a disease, symptom, disorder, pathological condition; determining a severity of a disease, symptom, disorder, pathological condition; monitoring disease, symptom, disorder, pathological condition progression; forecasting an outcome and/or prospects of recovery thereof. The term "Diagnostic" means identifying the presence or nature of a pathologic condition.

The term "substrate" is directed to a solid support on which the nucleic acid molecules, constructs, vectors and/or assay cells are placed. The substrate may include any type of suitable substrate, such as, but not limited to: chip, slide, well, container, tube, vial, and the like. In some embodiments, the substrate is a chip. In some embodiments, the substrate is a microscope slide. In some embodiments the substrate is a multi-well plate, such as a 6-well plate, 12-well plate, 24-well plate, 48-well plate, 96 well plate, 384 well plate, and the like. In some embodiments, the substrate is constructed such that it includes a matrix array (locuses), whereby each locus (or point in the array) is designated and identifiable. In some embodiments, the nucleic acid molecules are dehydrated on the substrate. In some embodiments, the nucleic acid molecules are dehydrated on the substrate in the presence or absence of a transfection reagent.

The terms "driver mutation" and "oncogenic mutation" may interchangeably be used. The terms are directed to a mutated gene or gene product, which is directly or indirectly related to a disease. In some embodiments, the terms are directed to a mutated gene or gene product that is related to and/or involved in and/or can lead and/or cause a disease, such as cancer.

The term "polynucleotides encoding for a protein" refers to a polynucleotide sequence or molecule encoding for the corresponding protein or a portion thereof. In some embodiments, the polynucleotide encoding for a protein comprises the nucleotide sequence of the gene or a portion thereof, which encodes for the corresponding protein.

The term "addressable array" is directed to a matrix, which includes spatially separated locuses, the location of which is identifiable and distinguishable. In some exemplary embodiments, an addressable array may include a multi-well plate, wherein each well (locus) is spatially identifiable. In other exemplary embodiments, an addressable array may include any substrate having separable locuses situated/located in a designated array.

Reference is now made to FIG. 1, which schematically illustrates a block diagram of exemplary steps in a method for identifying patient specific oncogenic mutations, in a biological sample of a patient, and for identifying drug response thereof, according to some embodiments. As shown in FIG. 1, at step 100, a biological sample of the patient is obtained. The biological sample may be selected from, but not limited to: blood, serum, biopsy, needle biopsy, bronchoalveolar lavage, pleural effusion, tumor tissue, urine, saliva and tumor tissue. In some embodiments, the biological sample may be fresh (fresh or freshly frozen), i.e. samples which are not fixed (step 102). In some embodiments, the biological sample may be fixed, by methods know in the art for fixation of biological sample (Step 104).

As shown in FIG. 1, from a fresh biological sample (Step 102), various components may be extracted, each by appropriate methods well known in the art. For example, as shown in Step 106, interstitial fluid (IF) (extracellular fluid) may be extracted and saved for future use. Additionally, mRNA may be extracted from the fresh biological sample (Step 108). The extracted/isolated mRNA is then used for the generation of cDNA libraries (Step 110), by methods well known in the art (such as, by using polydT primers). Specific PDM cDNAs are amplified from the cDNA library and created by using appropriate primer pairs, corresponding to desired gene regions (polynucleotides) of predetermined PDMs. The selected PDMs, may be chosen based on the known function/activity/role of a corresponding WT PDM or mutated PDM in various disease states (for example, oncogenes). Next, at step 112, an assay PDM is created, by adding a regulating promoter element to the 5' end of the PDM cDNA, and optionally adding a 3' IRES and a tag, such as a reporter gene, fluorescent tag, and the like. In some embodiments, the promoter element may be a constitutive promoter or an inducible promoter. In some embodiments, the PDM cDNA may further include an additional expression cassette which includes an FTR encoding portion. In some embodiments, the specific PDMs are generated by artificially synthesizing/generating the specific PDMs (based on their identified sequence), without the step of generation of a cDNA library.

As further shown in FIG. 1, at step 114, genomic DNA may be extracted from a fixed biological sample (such as a formalin fixed sample (Step 104)). At step 116, the extracted DNA may undergo amplification of specific, predetermined exons (which are known to be mutated in cancer cases) and consequent ligation/fusion to expression constructs comprising the corresponding full length gene, lacking the specific exons amplified to generate a tested PDM.

Next, in step 118, the nucleic acid molecule of each of the PDMs generated in step 112 and/or step 116 (via generation of cDNA, or artificially synthesized), may be placed/spotted on a support substrate (such as, a slide, well (for example, microplate well), chip, and the like) at a designated locus (location). The PDM is placed in a mixture with a nucleic acid molecule encoding for the chimeric reporter (FTR), wherein the FTR is selected to correspond to the PDM (i.e., the selected FTR may be functionally affected (directly or indirectly) by the PDM). The mixture of the nucleic acid molecules encoding for the PDM and the FTR may further comprise appropriate transfection reagents to allow the transfection of the molecules to a test cell. Optionally, the PDM+FTR mixtures are dehydrated onto the substrate. In another option, the PDM and FTR are constructed to be located on a single nucleic acid molecule, allowing independent expression of both proteins in the cell. In parallel, a control assay is prepared, which comprises a WT PDM and a corresponding FTR. Further in step 118, a sufficient amount of selected test cells are added to the substrate, together with appropriate growth media. The cells may be added prior to or after the addition of the nucleic acid molecules. In some embodiments, a sufficient amount of test cells comprises about 1-10000 cells per well (96 multi-plate well). In some embodiments, a sufficient amount of test cells comprises about 1-50000 cells per well (24 multi-plate well). In some embodiments, a sufficient amount of test cells comprises about 1-100000 cells per well (12 multi-plate well). In some embodiments, a sufficient amount of test cells comprises about 1-1000 cells per well (96 multi-plate well). In some embodiments, a sufficient amount of test cells comprises about 1-1000 cells per well (384 multi-plate well). In some embodiments, the test cell is selected from, but not limited to: HeLa cells, HEK 293 cells, U2OS, PC12, NCI60, A549, EKVX, T47D, HT29, and the like. The cells are then incubated for a designated period of time (such as, in the range of about 6-60 hours) to allow expression of the FTR and optionally of the PDM. Optionally, in some embodiments, in step 118, the cells are added to the solid substrate (with a suitable growth medium) for a period of time (such as 0.5-48 hours) and then the nucleic acid molecules encoding for the PDMs and/or FTR are added to the cells, under conditions allowing transfection of the molecules into the cells.

Next, at step 120, after a predetermined period of time (such as, 4-60 hours), cell growth medium may be replaced with fresh media. In some embodiments, the replacement media is low serum media. Next, after an additional incubation period (such as, in the range of 4-16 hours), induction of the expression of the PDM, controlled by an inducible promoter is initiated. Induction of the inducible promoter may be initiated, for example by addition of tetracycline when using a tetracycline inducible promoter, or ecdysone when using in an ecdysone inducible promoter or any other methods known in the art.

Optionally, at step 122, for PDMs generated from fixed samples (step 116), after a predetermined period of time (such as, 4-60 hours), cell growth medium is replaced with fresh media. In some embodiments, the replacement media is low serum media. Next, after an additional incubation period (such as, in the range of 4-24 hours), the PDMs are expressed under the control of a constitutive promoter.

Next, at step 124, after an additional period of time that allows for the expression of the PDMs in the test cells (such as, for example, in the range of about 4-48 hours), the subcellular localization of the FTR is determined. Determination of the subcellular localization of the FTR may be performed by various means, such as, imaging using a fluorescent microscope, fractionation of subcellular compartments using biochemical methods, and the like. In some exemplary embodiments, the cells are fixed and the fluorescent FTR localization is determined by fluorescent imaging. Analysis and comparison of the subcellular localization of the FTR under various experimental conditions allows the determination as to whether the tested PDM is defective (i.e. mutated), or not. For example, subcellular localization of the FTR is determined in cells, in which it is co-expressed with the tested PDM (test assay). In addition, subcellular localization of the same FTR is determined in cells, in which it was co-expressed with WT PDM (control assay). Differences in subcellular localization of the FTR between the test assay and the control assay indicate as to the functional activity of the tested PDM. Thus, for example, in Step 126, if the FTR is identified in the test assay to be at the same subcellular localization as in the control assay, the tested PDM is not mutated. For example, in Step 128, if the FTR is identified in the test assay to be at a different subcellular localization as in the control assay, the tested PDM is mutated, which indicates that this PDM is an oncogenic mutation. Next, at step 130, in order to determine drug response of the tested PDM(s), steps 120-124 are repeated, in the presence of a test drug (one or more drugs, or a combinations of drugs), that are added to the cells and incubated therewith. The drug may be added to the cells at varying concentration (as determined by properties of the drug) for any period of time, such as, for example, 10 minutes to 24 hours prior to cell fixation at a drug concentration of between 1 nM to 1 mM depending on drug type and effective conditions. A disparate result with respect to the FTR localization in the presence and absence of a drug is indicative of the drug response (susceptibility to the drug treatment) of the tested PDM.

Figure 2:
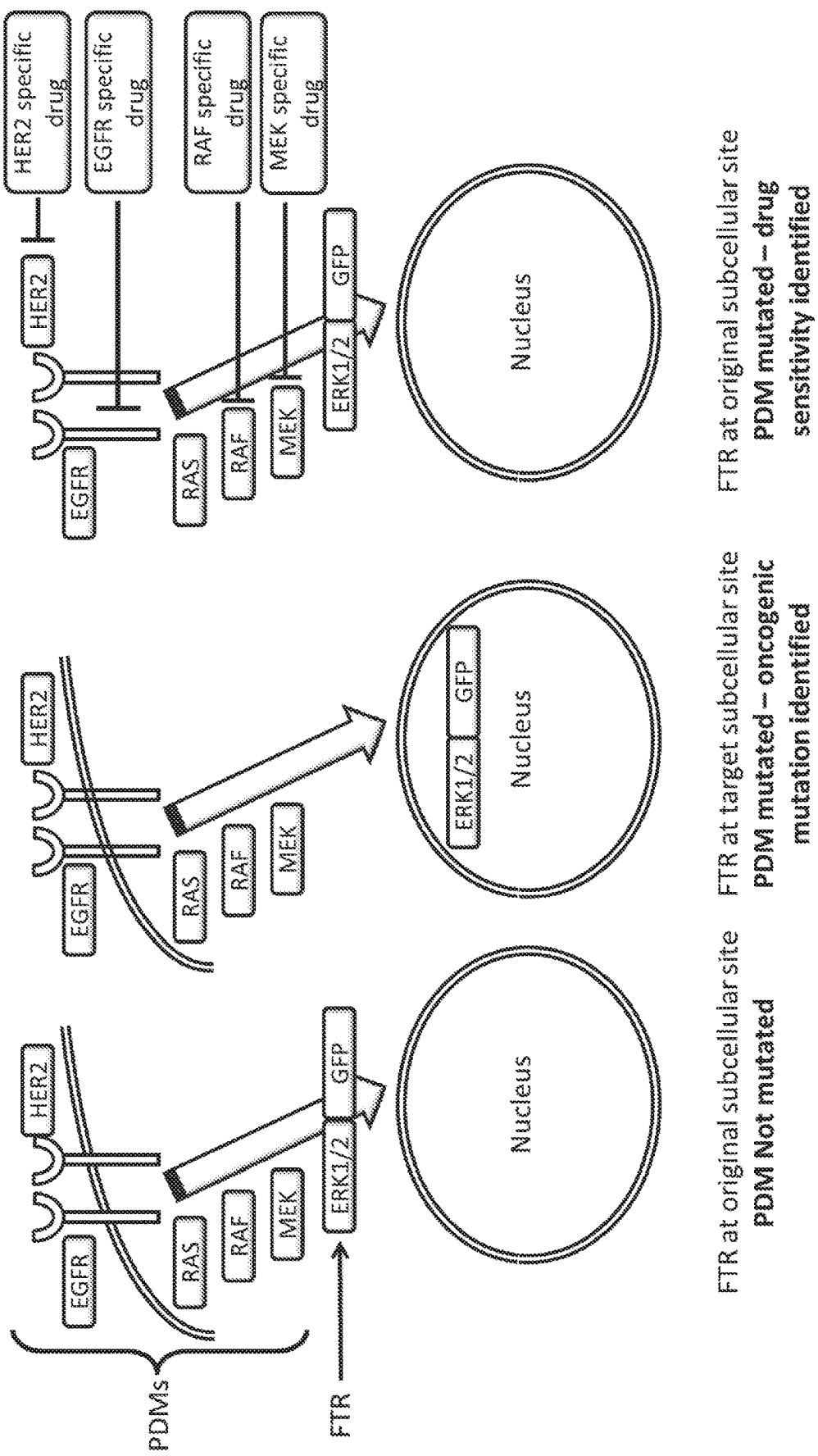
FIG. 2 is a schematic cartoon (not to scale) showing identification of specific patient driver mutations and detection of drug response thereof, according to some embodiments.

Reference is now made to FIG. 2, which is a schematic cartoon (not to scale) of application of the methods of the invention to identify oncogenic mutations in an exemplary cell signaling pathway, and the drug response thereof to a test drug, according to some embodiments. As shown in FIG. 2, various PDMs which are members of the MAP kinase signaling pathway (EGFR, HER2, RAS, RAF, and MEK) are prepared from a biological sample of a patient, as described above. The FTR in this exemplary assay is a chimeric reporter comprising of a MAPK protein (ERK1 or ERK2) as the target (marker) gene portion, fused to a GFP reporter gene (as the reporter gene portion). Each of the PDMs and the FTR are processed as described above herein and the localization of the FTR under the various experimental conditions is determined. As shown in the left hand panel, none of the tested PDMs is mutated, since the detected localization of the FTR is as in the WT condition (i.e. the FTR is localized to the cytoplasm)—therefore, none of the tested PDMs are mutated. As shown in the middle panel, at least one of the tested PDMs is mutated, since the subcellular localization of the FTR is different than in the WT conditions (i.e., in this example, it is in the nucleus). Since each of the tested PDMs is individually tested with the FTR in a separate test cell, identification of the specific mutated PDM is achievable. As shown in the right hand panel, various drugs, affecting various members of the exemplary cell signaling pathway may be used, to determine the specific drug response.

According to some embodiments, there is provided a method for identifying drug response of aberrant signal transduction pathways in biological samples of cancer patient, and/or of one or more patient specific oncogenic mutations, the method comprising one or more of the steps of (in any selected order):
 a) obtaining a sample of plurality of mRNA from a biological sample of a cancer patient, such as from a biopsy of the tumor;
 b) generating a cDNA library from the plurality of tumor mRNAs, by methods known in the art;
 c) amplifying individual cDNA samples of the cDNA library using a set of primers complementary to polynucleotides (genes or gene portions) encoding for known proteins, wherein the proteins are involved in various cell signaling pathways;
 d) forming individual expression constructs of the amplified cDNAs wherein the cDNAs are operably linked to a promoter, to produce test patient derived markers (test PDMs);
 e) forming an addressable array of a first set of expression constructs harboring the amplified cDNAs from the tumor (test PDMs), and in parallel a second set of expression constructs of the corresponding (matching) wild type proteins (WT PDMs);
 f) adding an expression vector for co-transfection of a marker gene linked to a specific reporter gene (FTR) for each locus in the array, wherein the marker gene is affected directly or indirectly by a corresponding PDM;
 g) optionally drying the cDNA constructs on a support solid substrate;
 h) adding viable assay cells to each locus under conditions enabling transfection of the DNA constructs into the assay cells;
 i) allowing expression of the constructs and expression vector in the transfected cells to obtain gene products of the first set of cDNAs from the tumor and the specific reporter gene for each locus in the array;
 j) comparing at least one attribute of the reporter gene in the cells expressing the cDNAs from the tumor with its corresponding wild type expressed cDNAs;
  a) Repeating any one of steps h) to i) in the presence of a drug and comparing at least one attribute of the expressed FTR in the assay cells expressing the cDNAs from the tumor and/or the corresponding wild type expressed cDNAs in the presence and absence of the drug;
 wherein a disparate result between the assay cells expressing the cDNA derived from the biological sample of the cancer patient and the corresponding wild type cDNA, is used for identifying the cDNA from the biological sample as a candidate patient specific oncogenic mutation; and wherein a disparate result between the assay cells expressing the cDNA derived from the biological sample of the cancer patient in the presence and absence of a drug is indicative of a drug response of the candidate patient specific oncogenic mutation.

In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In such embodiments, steps d) and f), above, are combined to one step: (alternative step d)): forming individual expression constructs of the amplified cDNAs wherein the cDNAs are operably linked to a promoter, to produce test patient derived markers (test PDMs); wherein said expression constructs further includes a specific reporter gene (FTR). In some embodiments, the FTR is linked to a promoter (that may be identical or different from the promoter of the PDM). In further embodiments, the FTR comprises a target gene portion linked to a reporter gene portion.

In some embodiments, step g) precedes steps e) and/or f), in which case the assay cells are added to each locus prior to addition of the expression cassettes.

In some embodiments, the method includes, in step e), a third set of expression constructs of corresponding proteins of the PDMs, which comprises one or more known driver mutations in said genes (herein "artificial PDMs"), that may be used as experimental control. The third set of expression constructs is added to the addressable array.

According to some embodiments, there is thus provided a method of identifying drug response of one or more patient specific oncogenic mutations in a biological sample of a cancer patient, the method comprising one or more of the steps of:
 a) obtaining a plurality of mRNAs from the biological sample;
 b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs wherein the cDNAs are operably linked to a promoter;

e) forming an addressable array of a first set of expression constructs harboring the amplified cDNAs from the biological sample, and a second set of expression constructs of the corresponding wild type cDNAs;

thereby providing an addressable array of expression constructs harboring candidate mutations in polynucleotides encoding for the signal transduction proteins, the array is suitable for identifying patient specific oncogenic mutations in a biological sample of the cancer patient.

In some embodiments, the method further comprises a step (f) of adding an expression vector encoding for a Fluorescence Translocation Reporter (FTR) gene comprising a target gene portion linked to a specific reporter gene portion for each locus in the array.

In further embodiments, the method further comprises the steps of: (g) adding viable assay cells to each locus under conditions enabling transfection of the DNA constructs and vectors into the assay cells; and (h) comparing at least one attribute of the expressed FTR in the assay cells expressing the cDNAs from the sample with its corresponding wild type expressed cDNAs; wherein a disparate result between the assay cells expressing the cDNA derived from the biological sample of the cancer patient and the corresponding wild type cDNA, is used for identifying the cDNA from the biological sample as a candidate patient specific oncogenic mutation.

In additional embodiments, the method further comprises step i) which comprises repeating any one of steps g) to h) in the presence of a drug and comparing at least one attribute of the expressed FTR in the assay cells expressing the cDNAs from the sample and/or the corresponding wild type expressed cDNAs in the presence and absence of the drug; wherein a disparate result between the assay cells expressing the cDNA derived from the biological sample of the cancer patient and the corresponding wild type cDNA, is used for identifying the cDNA from the biological sample as a candidate patient specific oncogenic mutation; and wherein a disparate result between the assay cells expressing the cDNA derived from the biological sample of the cancer patient in the presence and absence of a drug is indicative of a drug response of the candidate patient specific oncogenic mutation.

In some embodiments, the method includes, in step e), a third set of expression constructs of corresponding proteins of the PDMs, which comprises one or more known driver mutations in said genes (artificial PDMs), that may be used as experimental control. The third set of expression constructs is added to the addressable array.

According to some embodiments, there is provided a method of identifying or determining drug response of one or more patient specific oncogenic mutations in a biological sample of a cancer patient, comprising the steps of:

a) obtaining a plurality of mRNAs from the biological sample;

b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs wherein the cDNAs are operably linked to a promoter;

e) adding viable assay cells to a substrate, in an addressable array;

f) adding to the assay cells a first set of expression constructs harboring the amplified cDNAs from the biological sample, and a second set of expression constructs of the corresponding wild type cDNAs; wherein each of the expression constructs is added to the assay cells at a disparate, addressable locus, under conditions enabling transfection of the expression constructs into the assay cells;

thereby generating an array of assay cells comprising expression constructs harboring candidate mutations in polynucleotides encoding for signal transduction proteins for identifying patient specific oncogenic mutation in a biological sample of the cancer patient.

In some embodiments, the method further comprises a step of adding to the assay cells an expression vector of a Fluorescence Translocation Reporter (FTR) gene comprising a target gene portion linked to a specific reporter gene portion for each locus in the array.

In some embodiments, the assay cells are stably transfected with a designated FTR, and such assay cells, expressing the corresponding FTR may be used in the methods disclosed herein.

In some embodiments, the method includes, in step f), adding to assay cells at a disparate, addressable locus, under conditions enabling transfection, a third set of expression constructs of corresponding proteins of the PDMs, which comprises one or more known driver mutations in said genes (corresponding artificial PDMs).

In some embodiments, the method further comprises comparing at least one attribute of the FTR in the cells expressing the cDNAs from the biological sample with its corresponding wild type expressed cDNAs and/or corresponding artificial PDM; wherein a disparate result between the assay cells expressing the biological sample derived cDNA and the corresponding wild type cDNA is used for identifying the cDNA from the biological sample as a candidate patient specific oncogenic mutation.

In some embodiments, the method further comprises repeating a step of adding to the assay cells a drug and comparing at least one attribute of the expressed FTR in the assay cells expressing the cDNAs from the biological sample and/or the corresponding wild type expressed cDNAs and/or corresponding artificial PDM, in the presence and absence of the drug; wherein a disparate result between the assay cells expressing the cDNA derived from the biological sample of the cancer patient in the presence and absence of a drug is indicative of a drug response of the candidate patient specific oncogenic mutation.

In some embodiments, the biological sample is selected from tumor cells, tumor biopsy, tumor tissue and bodily fluids.

According to some embodiments, there is provided a method for identifying drug response of aberrant signal transduction pathways in biological samples of cancer patient, and/or of patient specific oncogenic mutation, comprising one or more of the steps of (in any appropriate order):

a) obtaining a sample of a plurality of mRNAs from a biological sample of the cancer patient, such as from a biopsy of the tumor;

b) generating a cDNA library from the plurality of tumor mRNAs, by methods know in the art;

c) amplifying individual cDNA samples of the cDNA library using a set of primers complementary to polynucleotides encoding for known proteins, wherein the proteins are involved in various cell signaling pathways;
d) forming individual expression constructs of the amplified cDNAs wherein the cDNAs are operably linked to a promoter and to a reporter gene, to produce chimeric test patient derived reporters (test PDRs);
e) forming an addressable array of a first set of expression constructs harboring the amplified cDNAs from the tumor (test PDRs), and in parallel a second set of expression constructs of the cDNAs (wt PDRs);
f) optionally drying the cDNA constructs on a support solid substrate;
g) adding viable assay cells to each locus under conditions enabling transfection of the DNA constructs into the assay cells;
h) allowing expression of the constructs and expression vector in the transfected cells to obtain gene products of the first set of cDNAs from the tumor;
i) comparing at least one attribute of the chimeric reporter gene in the cells expressing the cDNAs from the tumor with its corresponding wild type expressed cDNAs;
j) repeating any one of steps g) to h) in the presence of a drug and comparing at least one attribute of the expressed FTR in the assay cells expressing the cDNAs from the tumor and/or the corresponding wild type expressed cDNAs and/or the corresponding artificial PDM, in the presence and absence of the drug;

wherein a disparate result between the cells expressing tumor derived cDNA and the corresponding wild type cDNA is used for identifying the cDNA from the tumor as a candidate aberrant signal transduction protein; and wherein a disparate result between the assay cells expressing the cDNA derived from the biological sample of the cancer patient in the presence and absence of a drug is indicative of a drug response of the candidate patient specific oncogenic mutation.

According to some embodiments, there is provided a method of detecting or identifying a drug response of an aberrant signal transduction pathways in tumor cells, comprising one or more of the steps of (in any appropriate order):
a) obtaining a sample of mRNA from tumor cells, that may be obtained in-vitro or in-vivo, for example, from a tumor biopsy;
b) generating a cDNA library from the plurality of mRNAs obtained;
c) amplifying individual cDNA samples of the cDNA library using a set of primers complementary to polynucleotides encoding known signal transduction proteins;
d) forming individual expression constructs of the amplified cDNAs wherein the cDNAs are operably linked to a promoter;
e) forming an addressable array of a first set of expression constructs harboring the amplified cDNAs from the tumor, and in parallel a second set of expression constructs of the corresponding wild type cDNAs; and optionally, of a third set of expression constructs of corresponding proteins of the PDMs, comprising one or more known driver mutations in said genes (artificial PDMs);
f) adding an expression vector for co-transfection of a Fluorescence Translocation Reporter (FTR) chimeric gene comprising a target gene portion linked to a reporter gene portion, for each locus in the array;
g) adding viable assay cells to each locus under conditions enabling transfection of the DNA constructs into the assay cells;
h) comparing at least one attribute of the expressed FTR in the cells expressing the cDNAs from the tumor with its corresponding wild type expressed cDNA;
i) repeating any one of steps g) to h) in the presence of a drug and comparing at least one attribute of the expressed FTR in the assay cells expressing the cDNAs from the tumor and/or the corresponding wild type expressed cDNAs in the presence and absence of the drug;

wherein a disparate result between the cells expressing tumor derived cDNA and the corresponding wild type cDNA is used for identifying the cDNA from the tumor as a candidate aberrant signal transduction protein; and wherein a disparate result between the assay cells expressing the cDNA derived from the biological sample of the cancer patient in the presence and absence of a drug is indicative of the drug response of the aberrant signal transduction pathways.

In some embodiments, the drug is an anti-cancer drug/agent. In some embodiments, the more than one drug is added to the cells. In some embodiments, a combination (cocktail) of drugs may be added to the cells. In some embodiments, when more than one drug is added to the cells, the drugs may be added concomitantly or sequentially, at any time interval and for any incubation period.

In some embodiments, expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In some embodiments, step g) may precede steps e) and/or f), in which case the assay cells are added to each locus prior to addition of the expression constructs and/or expression vectors.

Accordingly, in accordance with some embodiments, there is provided a method for identifying drug response of aberrant signal transduction pathways in tumor cells, comprising one or more of the steps of (in any appropriate order):
a) obtaining a sample of mRNA from tumor cells, that may be obtained in-vitro or in-vivo, for example, from a tumor biopsy;
b) generating a cDNA library from the plurality of mRNAs obtained;
c) amplifying individual cDNA samples of the cDNA library using a set of primers complementary to polynucleotides encoding for known signal transduction proteins;
d) forming individual expression constructs of the amplified cDNAs wherein the cDNAs are operably linked to a first promoter; said expression constructs further comprise an expression cassette comprising a second promoter and encoding for a Fluorescence Translocation Reporter (FTR) chimeric gene, said FTR comprises a target gene portion linked to a reporter gene portion;
e) forming an addressable array of a first set of expression constructs harboring the amplified cDNAs from the tumor and the FTR cassette, and in parallel a second set of expression constructs of the corresponding wild type cDNAs and the FTR cassette;

f) adding viable assay cells to each locus under conditions enabling transfection of the DNA constructs into the assay cells; and g) comparing at least one attribute of the expressed FTR in the cells expressing the cDNAs from the tumor with its corresponding wild type expressed cDNA;

wherein a disparate result between the cells expressing tumor derived cDNA and the corresponding wild type cDNA is used for identifying the cDNA from the tumor cells as a candidate aberrant signal transduction protein.

In some embodiments, the first and second promoters are identical or different.

According to some embodiments, there is provided a method of detecting drug response of identified aberrant signal transduction pathways in tumor cells, comprising the steps of:

a) obtaining a plurality of mRNAs from the tumor cells;

b) generating a cDNA library from the plurality of mRNAs;

c) amplifying specific cDNAs of the cDNA library using a set of primers complementary to polynucleotides encoding for known signal transduction proteins;

d) forming individual expression constructs of the amplified cDNAs of step (c), wherein the cDNAs are operably linked to a promoter;

e) forming an addressable array of a first set of expression constructs harboring the amplified cDNAs from the tumor, and a second set of expression constructs of the corresponding wild type cDNAs;

thereby providing an addressable array of expression constructs harboring candidate mutations in the polynucleotides encoding for the signal transduction proteins, suitable for identifying aberrant signal transduction pathways in the tumor cells.

In some embodiments, the method further comprises a step (f) of adding an expression vector encoding for a Fluorescence Translocation Reporter (FTR) gene comprising a target gene portion linked to a reporter gene portion, for each locus in the array.

In additional embodiments, the method further comprises the steps of: g) adding viable assay cells to each locus under conditions enabling co-transfection of the DNA constructs into the assay cells; and h) comparing at least one attribute of the expressed FTR in the assay cells expressing the cDNAs from the tumor with its corresponding wild type expressed cDNAs; wherein a disparate result between the assay cells expressing cDNA derived from the tumor cells and the corresponding wild type cDNA is used for identifying the cDNA from the tumor cells as a candidate aberrant signal transduction protein.

According to some embodiments, there is provided a method for identifying drug response of factors capable of affecting tumoriogenity from a biological sample of a cancer patient, comprising one or more of the steps of (in any appropriate order):

a) adding viable assay cells to a substrate, in an addressable array;

b) adding to the assay cells an expression vector of a Fluorescence Translocation Reporter (FTR) gene comprising a target gene portion linked to a specific reporter gene portion for each locus in the array;

c) adding to the assay cells the biological sample of the patient at specific locuses of the array;

d) comparing at least one attribute of the expressed FTR in the cells to which the biological sample of the patient was added, with the corresponding cells to which the biological sample was not added;

e) repeating any one of steps c)-d) in the presence of a drug and comparing at least one attribute of the expressed FTR in the assay cells to which the biological sample of the patient was added, with the corresponding cells to which the biological sample was not added, in the presence and absence of the drug;

wherein a disparate result between the cells to which the biological sample of the patient was added and the corresponding cells to which the biological sample was not added, is used for identifying the biological sample comprising factors capable of affecting tumoriogenity; and wherein a disparate result between the cells to which the biological sample of the patient was added and the corresponding cells to which the biological sample was not added, in the presence and absence of a drug is indicative of the drug response of the factors capable of affecting tumoriogenity.

In some embodiments, the biological sample is selected from patient tumor microenvironment, extracellular fluid, secreted fluid from the tumor, plasma, Bronchoalveolar lavage, and the like, or combinations thereof.

In some embodiments, the factors capable of affecting tumoriogenity are selected from autocrine factors, paracrine factors, or both.

In some embodiments, the assay cells stably express an FTR. In some embodiments, step b) may precede step a), in which case, the cells are added to the expression vector of the FTR, which is added in an addressable array.

According to some embodiments, there is provided a method of identifying drug(s) capable of suppressing the effect of one or more patient specific mutations and/or drug response of one or more patient specific mutations and/or susceptibility to drug(s) of one or more patient specific mutations, comprising one or more of the steps of (in any order):

a) forming an addressable array of a first set of expression constructs harboring genes comprising patient specific mutation(s), and a second set of expression constructs of corresponding wild type genes;

b) adding an expression vector encoding for a Fluorescence Translocation Reporter (FTR) gene comprising a target gene portion linked to a specific reporter gene portion for each locus in the addressable array;

c) adding viable assay cells to each locus under conditions enabling transfection of the expression constructs and expression vectors into the assay cells; and d) comparing at least one attribute of the expressed FTR in the assay cells expressing the genes comprising the one or more patient specific mutation(s) with its corresponding wild type expressed gene in the presence and absence of the drug;

wherein a disparate result between the assay cells expressing the genes comprising the mutation, and/or the corresponding wild type genes in the presence and absence of a drug is indicative of a drug capable of suppressing the effect of the patient specific mutation.

According to some embodiments, the drug is an anti-cancer drug. In some embodiments, the method includes adding more than one drug, concomitantly or sequentially. In some embodiments, the method includes adding a combination of drugs. In some embodiments, the method includes adding varying concentration of drug(s), to determine the drug response.

In some embodiments, the attribute of the FTR may be selected from localization of a fluorescent protein and translocation of a fluorescent protein. In some embodiments, the localization may include a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In some embodiments, the reporter gene portion of the FTR may encode for a fluorescent marker, such as a fluorescent protein.

In some embodiments, the patient genes may be obtained/derived from a biological sample of the patient. In some embodiments, the biological sample may be selected from tumor cells, tumor biopsy, tumor tissue and bodily fluids, microenvironment extract, extracellular fluid, secreted fluid from tumor. In some embodiments, the patient is cancer patient. In some embodiments, the mutation is an oncogenic mutation.

In some embodiments, the first and/or second set of expression constructs harbors a portion of a gene. In some embodiments, the method the first and/or second sets of expression constructs include a double stranded linear DNA. In some embodiments, the promoter of the first and/or second set of expression constructs may be an inducible or a constitutive promoter. In some embodiments, the method further includes drying the expression constructs on a solid support in the presence of a transfection reagent. In some embodiments, the expression cassette of the PDM and the expression cassette of the FTR are located on one expression construct (i.e., on a single molecule). In such embodiments, PDM expression cassette and the FTR expression cassette may have identical, similar or different promoters (i.e., the expression of the PDM and the FTR may be controlled by the same or different promoter). In some embodiments, step c) may precede step a) and/or step b), in which case the assay cells are added to the addressable array prior to addition of the expression constructs and/or the expression vectors.

According to some embodiments, there is provided a method of identifying susceptibility to drug treatment of one or more patient specific mutations, comprising the steps of:
a) forming an addressable array of a first set of expression constructs harboring genes comprising patient specific mutation, and a second set of expression constructs of corresponding wild type genes;
b) adding an expression vector encoding for a Fluorescence Translocation Reporter (FTR) gene comprising a target gene portion linked to a specific reporter gene portion for each locus in the addressable array;
c) adding viable assay cells to each locus under conditions enabling transfection of the expression constructs and expression vectors into the assay cells; and
d) comparing at least one attribute of the expressed FTR in the assay cells expressing the genes comprising the mutation(s) with its corresponding wild type expressed gene in the presence and absence of the drug;
wherein a disparate result between the assay cells expressing the genes harboring the mutation, and/or the corresponding wild type genes, in the presence and absence of a drug, is indicative of the susceptibility to treatment of the patient specific oncogenic mutations, with the drug.

According to some embodiments, there is provided a method of detecting drug response of one or more patient specific oncogenic mutations of a cancer patient, comprising the steps of:
a) adding viable assay cells to a substrate, in an addressable array under conditions enabling transfection of expression constructs and expression vectors into the assay cells;
b) adding to the assay cells an expression vector of a Fluorescence Translocation
Reporter (FTR) gene comprising a target gene portion linked to a specific reporter gene portion for each locus in the array;
c) adding to the assay cells, at specific locuses of the addressable array, a first set of expression constructs harboring genes comprising patient specific mutations, and adding to the assay cells, at specific locuses a second set of expression constructs of corresponding wild type genes, wherein the first set of expression constructs and the second sets of expression constructs are not added to a common locus; and
d) comparing at least one attribute of the expressed FTR in the assay cells expressing the oncogenic mutation(s) with its corresponding wild type expressed gene in the presence and absence of the drug;
wherein a disparate result between the assay cells expressing the genes harboring the mutation, and/or the corresponding wild type genes, in the absence and/or presence of a drug, is indicative of a drug response of the patient specific driver mutation.

According to some embodiments, the drug is an anti-cancer drug. In some embodiments, the method includes adding more than one drug, concomitantly or sequentially. In some embodiments, the method includes adding a combination of drugs. In some embodiments, the method includes adding varying concentration of drug(s), to determine the drug response.

In some embodiments, the attribute of the FTR may be selected from localization of a fluorescent protein and translocation of a fluorescent protein. In some embodiments, the localization may include a subcellular localization selected from: cytosol, nucleus, nucleolus, plasma membrane, endoplasmic reticulum (ER), mitochondria, Golgi apparatus, lysosomes, peroxisomes, endosomal compartments, and cytoskeleton.

In some embodiments, the target gene portion of the FTR encodes for a protein selected from tumor suppressor, cytoskeleton protein, growth factor receptor, G-protein coupled receptor, cell adhesion protein, a protein kinase, transcription factor, adaptor protein and exchange factor. In some embodiments, the reporter gene portion of the FTR may encode for a fluorescent marker, such as a fluorescent protein.

In some embodiments, the patient genes may be obtained/derived from a biological sample of the patient. In some embodiments, the biological sample may be selected from tumor cells, tumor biopsy, tumor tissue and bodily fluids, microenvironment extract, extracellular fluid, secreted fluid from tumor. In some embodiments, the patient is cancer patient. In some embodiments, the mutation is an oncogenic mutation.

In some embodiments, the first and/or second set of expression constructs harbors a portion of a gene. In some embodiments, the method the first and/or second sets of expression constructs include a double stranded linear DNA. In some embodiments, the promoter of the first and/or second set of expression constructs may be an inducible or a constitutive promoter. In some embodiments, the method further includes drying the expression constructs on a solid support in the presence of a transfection reagent. In some embodiments, step b) and/or step c) may precede step a), in which case, the cells may be added to the expression constructs and/or the expression vectors.

According to some embodiments, the expression constructs used in the methods disclosed herein may be obtained by a process comprising one or more of the following steps:
  i) generating a cDNA library from a plurality of mRNAs obtained from the biological sample of the patient;
  ii) amplifying specific cDNAs of the cDNA library using a set of primers complementary to polynucleotides encoding for genes suspected of harboring an oncogenic mutation; and
  iii) operably linking the amplified cDNAs to a promoter.

In some embodiments, the patient's genes or gene portions, suspected of harboring one or more mutations, may be synthesized by methods known in the art and optionally be operably linked to a promoter to obtain the expression constructs. In some embodiments, the patient genes (or portions thereof) and/or the corresponding wild type genes may be artificially synthesized, based on their sequence and further processed to generate the corresponding PDMs, as detailed herein.

According to some embodiments, a patient is a patient afflicted with cancer. In some embodiments, cancers include such cancers as: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, lung cancer, pancreatic cancer, cancer of the thyroid, head and neck cancer, cancer of the central nervous system, cancer of the peripheral nervous system, skin cancer, kidney cancer, as well as metastases of all the above. Particular types of tumors amenable to treatment include: hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocytoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer is selected from prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer.

In some embodiments, the patient has been diagnosed positive for cancer. In some embodiments, the patient is subjected to targeted therapy treatment regimen with known or unknown treatment results. In some embodiments, the patient has an available patient tumor molecular profiling (IHC, FISH, PCR and sequencing). In some embodiments, the patient has available patient history as well as outcome (patient response, resistance, recurrence and survival rates).

In some embodiments, the biological sample is selected from: blood, serum, biopsy, tissue, needle biopsy, bronchoalveolar lavage, pleural effusion, urine, saliva and tumor. In some embodiments, the biological sample may be freshly isolated. In some embodiments, the biological sample may be frozen. In some embodiments, the biological sample may be fixed.

In some embodiments, each protein expressed in an assay cell (such as, tested PDM, FTR, WT PDM, PDR) is differentially identifiable. In another embodiment, each protein, directly or indirectly, may be identified by a different marker or reporter or a different fluorescent protein. In another embodiment, each chimeric protein (such as, FTR, or PDR) comprises a different reporter moiety. In another embodiment, different proteins may share a fluorescent protein or reporter. In another embodiment, each chimera protein of the invention comprises a different reporter moiety.

In another embodiment, a PDM is associated with cancer growth. In another embodiment, a PDM is an oncogene or tumor suppressor. In another embodiment, a PDM is a cytoskeletal regulator. In another embodiment, a PDM has a role in tumor growth and metastasis. In another embodiment, a PDM is a vesicle trafficking protein. In another embodiment, a PDM is a vesicle tethering protein. In another embodiment, a PDM is a cell adhesion protein. In another embodiment, a PDM is a nuclear integrity protein. In another embodiment, a PDM is a growth factor receptor. In another embodiment, a PDM is a cytokine receptor. In another embodiment, a PDM is a cell attachment protein. In another embodiment, a PDM is involved in tumor inflammation. In another embodiment, a PDM is a cell polarity protein. In another embodiment, a PDM is a signaling protein. In another embodiment, a PDM is an adaptor protein. In another embodiment, a PDM is a protein kinase. In another embodiment, a PDM is an exchange factor. In another embodiment, a PDM is a cytoskeletal protein. In some exemplary embodiments, a PDM is selected from the group comprising or consisting of: AKT1, AKT2, AKT3, ALK, BRAF, BRCA1, BRCA2, CBL, CTNNB1, EGFR, ERBB2, ERBB3, FGFR1, FGFR2, GNA11, GNAQ, HRAS, JAK2, KIT, KRAS, MET, NRAS, PDGFRA, PIK3CA, PTEN, RAF1, RET, ROS1, SMO, TP53, SMAD2, SMAD3, SMAD4, STAT1, STAT3, STAT5B, TGFBR2, FBXW7, MYC, LKB1, SMARCA4, TCF7L2, MAP3K1, ESR1, AR, PR, DDR2, MEK1 or any combination thereof. Each possibility is a separate embodiment.

In another embodiment, a PDM is expressed in conjunction to marker (tag) such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1). In some embodiments, the marker comprises a marker motif of Cys-Cys-Pro-Gly-Cys-Cys (SEQ ID NO:47), and prior to imaging, FlAsH-EDT2 or ReAsH-EDT2 may be added to the test assay, to become fluorescent upon binding to recombinant proteins containing the Cys-Cys-Pro-Gly-Cys-Cys motif. In some embodiments, the protein comprising the Cys-Cys-Pro-Gly-Cys-Cys may be the PDM, a fluorescent protein alone, or a fluorescent protein fused to a subcellular marker that can further be used to tag subcellular organelles, such as, for example, plasma membrane or nucleus. In some embodiments, the marker (tag) expressed in conjunction to the PDM is used as a marker to verify transfection and expression of the PDM in an assay cell.

In another embodiment, a PDR is a PDM fused to marker (tag) such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1. In some embodiments, a PDR is a PDM fused to marker (tag), comprising a Cys-Cys-Pro-Gly-Cys-Cys (SEQ ID NO:47) motif.

In some embodiments, the FTR is a fusion (chimeric) protein comprising a reporter portion, such as a fluorescent protein (such as mCherry, mApple, GFP, Cherry, DsRed, RFP, EGFP, BFP, YFP, AmCyan1, ZsGreen1, ZsYellow1, DsRed2, AsRed2, and HcRed1) or a Cys-Cys-Pro-Gly-Cys-Cys motif, and a target protein portion selected from, but not limited to: a protein associated with cancer growth, an oncogene product, a cytoskeletal regulator, vesicle trafficking protein, vesicle tethering protein, cell adhesion protein, nuclear integrity protein, growth factor receptor, cell attachment protein, cell signaling protein, protein involved in tumor inflammation, cell polarity protein, growth factor signaling protein, an adaptor, a cytoskeletal protein, and the like. Each possibility is a separate embodiment.

In some exemplary embodiments, the FTR is a fusion protein comprising a reporter portion, such as a fluorescent protein, and a target (marker) protein portion selected from the group comprising or consisting of, but not limited to: AKT1, AKT2, mTOR, RelA, NFKB1, NFKB2, ERK1, ERK2, ERF, STAT1, STAT3, STAT5, CTNNB1, JNK1alpha, JNK1beta, JNK2alpha, JNK2beta, ERK5, P38alpha, P38beta, AMPK, STK11, SMARCA4, TP53, ESR1, GATA3, CDK2, SMAD1, NOTCH1, MYB, MYC, SMAD2, SMAD3, SMAD4, PRKACA, NLK or any combination thereof. Each possibility is a separate embodiment.

In some exemplary embodiments, the PDM may be KRas and the target portion of the FTR may be selected from: ERK2, ERF, JNK and AKT1. Each possibility is a separate embodiment.

In some exemplary embodiments, the PDM may be AKT2 or AKT3 and the target portion of the FTR may be selected from: AKT1 and RelA. Each possibility is a separate embodiment.

In some exemplary embodiments, the PDM may be FGFR1 and the target portion of the FTR may be selected from: ERK2, JNK (such as JNK1alpha 1), p38b, AKT1 and STAT3. Each possibility is a separate embodiment.

In some exemplary embodiments, the PDM may be BRaf and the target portion of the FTR may be selected from: ERK2 and ERF. Each possibility is a separate embodiment.

In some exemplary embodiments, the PDM may be EGFR and the target portion of the FTR may be selected from: ERK2, RelA, AKT1, p38b, JNK1a1. Each possibility is a separate embodiment.

In another embodiment, the invention includes assay cells, wherein each assay cell expresses a PDM and/or an FTR. In another embodiment, the invention includes assay cells, wherein each assay cell expresses a different PDM and/or an FTR and/or PDR. In another embodiment, the invention includes assay cells, wherein each assay cell is transfected with a different DNA fragment, wherein each DNA fragment encodes a different PDM and/or an FTR. In some embodiments, the assay cells are placed/plated/grown on solid substrate having designated locuses (locations). In some embodiments, the assay cells are identical for each locus. In some embodiments, the assay cells are not identical for each locus. In some embodiments the assay cells are added in medium to each locus. In some embodiments, the cells are added to a solid substrate already having DNA constructs dehydrated thereto. In some embodiments, the cells are first plated on the solid substrate and transfected after a predetermined period of time.

In another embodiment, the invention includes assay cells, wherein each assay cell is transfected with a different DNA fragment, wherein each DNA fragment encodes a different PDM and/or an FTR and/or PDR.

In some embodiments, identification of localization of the FTR is performed using a protein assay, binding assay, an immunoassay, microscopic imaging, or any other suitable assay known to those of skill in the art.

In some embodiments, the invention further includes the step of detecting a morphological change in an assay cell. In some embodiments, the methods of the invention do not require sequencing of any patient DNA.

According to some embodiments, the drug is an anti-cancer drug. In some exemplary embodiments, the drug may be selected from, but not limited to: Afatinib, Brentuximab vedotin, Buparalisib, cabozantinib, carfilzomib, cetuximab, crizotinib, dabrafenib, dasatinib, denosumab, Erlotinib, Everolimus, gefitinib, ibritumomab tiuxetan, Ibrutinib, Idelalisib, imatinib mesylate, ipilimumab, lapatinib, Neratinib, nilotinib hydrochloride monohydrate, obinutuzumab, ofatumumab, panitumumab, pazopanib, pertuzumab, ponatinib, Regorafenib, Rituxan, sorafenib, Selumetinib, sunitinib, temsirolimus, trametinib, trastuzumab, vandetanib, vemurafenib, vismodegib, ziv-aflibercept, and any combinations thereof. Each possibility is a separate embodiments.

According to some embodiments, the drug(s) may be added to the test cells at any desired amount/concentration. For example, the drug may be added at a concentration of: 1 nM to 1 mM and any subranges thereof, such as, for example, but not limited to: 150 nM-750 nM, 12.5 µM-100 µM, 200 nM-25 µM, and the like.

According to some embodiments, the drug(s) may be added and incubated with the test cells for any desired period of time, such as for example, in the range of: 10 minutes to 24 hours.

According to some embodiments, there is provided a kit for diagnosing cancer in a patient. In some embodiments, there is provided a kit for identifying an aberrant cellular signaling pathway in tumor cells. In some embodiments, there is provided a kit for identifying patient specific oncogenic mutations. In some embodiments, there is provided a kit for determining/detecting/identifying drug response of patient specific oncogenic mutations. In some embodiments, there is provided a kit for measuring the response/resistance of patient mutant genes to drug therapies.

In some embodiments, the invention provides a kit for diagnosing cancer or the molecular cancer profile in a subject, by identifying patient specific oncogenic mutations. The kit can be used, according to some embodiments, for predicting treatment success or identifying paracrine or autocrine factors involved in cancer. In another embodiment, the kit comprises at least one means of detecting a reporter gene. In another embodiment, the kit comprises means for detecting a marker. In some embodiments, the kit contains one or more of: a substrate or container for holding nucleic acid molecules and/or test cells, directions for carrying out detection/translocation assay(s), test cells, transfection reagents, or any combination thereof.

Diagnostic compositions of the present invention may, if desired, be presented in an article of manufacture e.g., kit, such as an FDA approved kit, which may contain diagnostic reagents and instructions for use. The kit may also be accommodated by a notice associated with the container in a form prescribed by a governmental agency regulating the manufacture, use or sale of pharmaceuticals, which notice is reflective of approval by the agency of the form of the compositions or human or veterinary use.

In another embodiment, the methods and kits of the invention increase survival of cancer patients. The assays of the present invention are ideally suited for the preparation of kits. Such a kit may comprise a carrier means being compartmentalized to receive in close confinement there with one or more container means such as vials, tubes, plates, slides, and the like, each of the container means comprising the separate elements of the cell assay.

In one embodiment, a kit for diagnosing cancer in a subject comprising a panel of assay cells each includes a different protein of the invention is provided, the kit comprising a substrate having nucleic acid molecules encoding for PDM (derived from a biological sample of the patient) and/or FTR and/or FTR, wherein the substrate is further capable of holding assay cells and a biological sample isolated from a human subject suspected of having cancer and printed instructions for reacting measuring and or detecting translocation events.

In some embodiments, transfected assay cells are cultured under effective conditions, which allow for the expression of recombinant protein or tagged proteins. In one embodiment, a tagged or marker protein of the invention (such as PDM, FTR) is a recombinant protein or a chimera. In some embodiments, effective culture conditions include, but are not limited to, effective media, bioreactor, temperature, $CO_2$, pH and oxygen conditions that permit protein expression. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, the present invention utilizes redistribution technology for monitoring and recording protein translocation event. In another embodiment, protein targets are labeled with the green fluorescent protein or other fluorescent proteins, and stably or transient transfected cell lines are generated. In another embodiment, the assays of the invention are read using a high-throughput, optical microscope-based instrument.

In another embodiment, protein translocation assay of the invention is high-content, high-throughput assay primarily used for profiling of lead series, primary screening of PDMs derived from biological samples as a constituent of cell media. In another embodiment, a protein translocation assay of the invention includes live-cell imaging, using Spinning Disc technology or any other microscopy based technology.

In some embodiments, a toponomic localization technique is used to follow and record protein translocation events. In some embodiments, means of immunofluorescence, of proteins of the invention, are utilized. In some embodiments, proteins of the invention are labeled with fluorescent markers. In some embodiments, confocal microscopic images are assessed and processed. In another embodiment, a standard dataset included 2-40 images of each cell per biological condition. In another embodiment, automated image analysis is performed. In another embodiment, automated image analysis includes cellular compartment or structure identification.

In another embodiment, spatial relations are captured in different dimensionalities. In another embodiment, quantitative assessment of protein-marker concentrations in bounded regions is performed. In another embodiment, the present invention further provides protein co-localization studies, based on measuring and evaluating isotropic distributions of distances between pixels. In another embodiment, the present invention provides a 2-dimensional analysis (regions). In another embodiment, the present invention further provides a 0-dimensional analysis (points). In another embodiment, the present invention provides 1-dimensional modeling.

The terms "comprises", "comprising", "includes", "including", "having" and their conjugates mean "including but not limited to". The terms "comprises" and "comprising" are limited in some embodiments to "consists" and "consisting", respectively. The term "consisting of" means "including and limited to". The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

As used herein the term "about" in reference to a numerical value stated herein is to be understood as the stated value +/−10%.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The following examples are presented in order to more fully illustrate some embodiments of the invention. They should, in no way be construed, however, as limiting the broad scope of the invention.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989);

Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Biological Sample Collection

Both formalin fixed paraffin embedded (FFPE) tumor biopsies as well as frozen fresh tumor parts or biopsies are collected. The FFPE samples are used to extract specific genomic exons that are known to be involved in cancer progression (such as cKit exon 11). The fresh (fresh or fresh frozen) biopsy is used for both mRNA extraction and interstitial fluid extraction.

Thus, both retrospective and prospective samples are collected. Retrospective study based on frozen tumor sections from cases that the treatment efficacy is known.

Prospective study based on fresh or snap frozen sample/biopsy tissue/tumor section collected immediately following surgery/biopsy/bronchoscopy. This enables amplification of all relevant tested proteins (such as oncogenes or indicators). Other body fluids such as plasma samples (using Heparane sulfate gel tubes), blood samples, peritoneal fluid, pleural effusion and lung fluids obtained through bronchoscopy are of great importance as they accumulate much of the tumor secretions and are also collected.

Following tumor resection (surgery, biopsy, Bronchoscopy), the tumor tissue is placed in a sterile bag or tube on ice (not treated with formalin). A pathologist subdivides the tumor (taking into account size and location of viable tumor section) to those required for fixation and those best representing the tumor that are delivered fresh on ice for further analysis. The pathologist identifies a tissue section or area enriched with malignant cells and with reduced amount of stroma or other non-malignant tissue and excises it. If the net weight of the tissue exceeds 1 grams, tissue is further cut to several pieces and placed on a cellulose column and spun at 100 g for 10 min (100±50 microliter of IF are expected from every gram of tissue). Tissue is then transferred to another 15/50 ml tube and frozen in a −80° C. freezer. Spun down liquid known as the Interstitial fluid (IF) are frozen in original tube.

Needle biopsy—Tissue is placed in a 15 conical tube and frozen in a −80 freezer.

Biopsy via Bronchoscopy—Tissue is placed in a 15 conical tube and frozen in a −80 freezer.

Bronchoalveolar lavage—Extracted liquid is split between 2 50 ml falcon tubes and Spun down (3000 RPM, 15 min.). Liquid is transferred into new tubes and both liquid and cells (in original tubes) are frozen at −80° C.

Pleural effusion—Pleural effusion is spun down (3000 RPM, 15 min.), liquid transferred into new tubes and both liquid and cells (in original tubes) frozen at −80° C.

Cryosection—if possible the tumor is frozen in a microtome and sectioned.

Extraction of Genomic DNA from Formalin Fixed Embedded Tumor Biopsies

To identify genes in which known mutations are present in specific exons, such as cKit mutations in exon 11, EGFR exons 19, 20, HER2 exon 20, DNA extracted from FFPE tissue is used. To this aim, standard DNA extraction kits and protocols are used (for example, Qiagen QIAamp DNA FFPE Tissue, cat. #56404).

Amplification of Exons and Insertion to Full Length Gene

To express desired exons, amplification from the genomic DNA is performed and insertion of the exon into the full length gene lacking this exon. To this aim, full length genes lacking the exon in expression ready vectors are produced and then the exon is incorporated into the construct using conventional molecular biology techniques.

Fresh Biopsies: Extraction of the Needed Amount of Tissue from Frozen Biopsy

A fraction of the biopsy is used for RNA purification and interstitial fluid extraction. The rest of biological material is stored for future reference or additional analysis (Immunohistochemistry (IHC), FISH, and the like).

Extraction of Interstitial Fluid (IF)

The interstitial fluid (IF) extracted as detailed below, is stored for later use as an agonist to the tested cells, to detect the presence of agents that are secreted by the tumor cells and may confer resistance to anti-cancer drugs.

IF extraction is performed by centrifuging the tissue sample in a column with glass fiber filter at 4° C. for 7 min at 1500 g. The fluids are then collected from the bottom part of the column into a new tube.

Extraction of mRNA mRNA extracted from the sample is needed for the amplification of the patient derived markers (PDMs), i.e. genes that are known oncogenes and potentially harbor mutations that provide the cell with oncogenic properties (genes with potential of harboring oncogenic mutations). Exemplary genes that are tested include: AKT1, AKT2, AKT3, ALK, BRAF, BRCA1, BRCA2, CBL, CTNNB1, EGFR, ERBB2, ERBB3, FGFR1, FGFR2, GNA11, GNAQ, HRAS, JAK2, KIT, KRAS, MET, NRAS, PDGFRA, PIK3CA, PTEN, RAF1, RET, ROS1, SMO, TP53, SMAD2, SMAD3, SMAD4, STAT1, STAT3, STAT5B, TGFBR2, FBXW7, MYC, LKB1, SMARCA4, TCF7L2, MAP3K1, AR, PR, ESR1, DDR2, MEK1, and MEK2.

RNA extraction is performed by methods known in the art, including the Guanidium-Cesium Chloride Method, Guanidium Acid-Phenol Method and glass fiber filters that bind nucleic acids in the presence of chaotropic salts and/or by use of commercially available kits (such as Qiagen RNeasy kit cat #74106, used in accordance with manufacturer instructions).

Generation of cDNA

To allow amplification of PDMs, cDNA is synthesized based on the mRNA extracted from the tissue. cDNA is synthesized based on the template mRNA using a RNA-dependent DNA polymerase reverse transcriptase enzyme and using oligo-dT primers, random hexameric primers, or specific primers. Exemplary protocol includes using SuperScript™ III First-Strand Synthesis SuperMix protocol (Life technologies, cat #18080-051).

Generation of Test PDMs

The generation of the test PDMs is performed in two steps: amplification of the selected PDMs and attachment of additional elements to allow their proper expression in the assay cells.

In a direct approach, a preliminary PCR reaction containing the oligonucleotides related to the test PDMs that are amplified is performed, to allow over-representation of these selected genes within the cDNA sample. In an indirect approach, the test PDM is artificially synthesized, based on the sequence of the specific test PDM, and this artificial PDM may be used as a template for a PCR reaction, using the appropriate primers.

In some examples, the cDNA sample is aliquoted into separate wells/tubes for each gene that is to be amplified.

Using primers designed for each PDM, a PCR reaction is performed to amplify the selected PDM gene from the cDNA library, or based on an artificially generated template PDM.

The following sets of primers are used for the PCR amplification of the following tested PDMs (Table 1):

TABLE 1

| PDM (name) | Accession number | 5' primer | 3' primer |
|---|---|---|---|
| AKT1 (v-akt murine thymoma viral oncogene homolog 1) | NM_001014431.1 | ATGAGCGACGTGGCT ATTGT (SEQ ID NO: 1) | TCAGGCCGTGCCGCT GGC (SEQ ID NO: 2) |
| AKT2 (v-akt murine thymoma viral oncogene homolog 2) | NM_001626.4 | ATGAATGAGGTGTCT GTCATCAAAG (SEQ ID NO: 23) | TCACTCGCGGATGCT GG (SEQ ID NO: 24) |
| AKT3 (v-akt murine thymoma viral oncogene homolog 3) | NM_005465.4 | ATGAGCGATGTTACC ATTGTG (SEQ ID NO: 25) | TTATTCTCGTCCACT TGCAGAG (SEQ ID NO: 26) |
| BRAF (v-raf murine sarcoma viral oncogene homolog B) | NM_004333.4 | ATGGCGGCGCTGAGC GGTG ((SEQ ID NO: 3) | TCAGTGGACAGGAAA CGCAC (SEQ ID NO: 4) |
| EGFR (Epidermal growth factor) | NM_005228.3 | ATGCGACCCTCCGGG ACG (SEQ ID NO: 5) | TCATGCTCCAATAAA TTCACTGCT (SEQ ID NO: 6) |
| HRAS (Harvey rat sarcoma viral oncogene homolog) | NM_005343.2 | ATGACGGAATATAAG CTGGTGGT (SEQ ID NO: 7) | TCAGGAGAGCACACA CTTGC (SEQ ID NO: 8) |
| MEK1 (mitogen-activated protein kinase kinase 1) | NM_002755.3 | ATGCCCAAGAAGAAG CCGAC (SEQ ID NO: 9) | TTAGACGCCAGCAGC ATGG (SEQ ID NO: 10) |
| NRAS (neuroblastoma RAS viral (v-ras) oncogene homolog) | NM_002524.4 | ATGACTGAGTACAAA CTGGTGGT (SEQ ID NO: 11) | TTACATCACCACACA TGGCA (SEQ ID NO: 12) |
| PDGFRA (platelet-derived growth factor receptor, alpha polypeptide) | NM_006206.4 | ATGGGGACTTCCCAT CCGG (SEQ ID NO: 13) | TTACAGGAAGCTGTC TTCCACC (SEQ ID NO: 14) |

TABLE 1-continued

| PDM (name) | Accession number | 5' primer | 3' primer |
|---|---|---|---|
| PIK3CA (phospha-tidylinositol-4,5-bisphosphate 3-kinase, catalytic subunit alpha) | NM_006218.2 | ATGCCTCCACGACCATCATC (SEQ ID NO: 15) | TCAGTTCAATGCATGCTGTT (SEQ ID NO: 16) |
| PTEN (phosphatase and tensin homolog) | NM_000314 | ATGACAGCCATCATCAAAGAGA (SEQ ID NO: 17) | TCAGACTTTTGTAATTTGTGTATGC (SEQ ID NO: 18) |
| RAF1 (v-raf-1 murine leukemia viral oncogene homolog 1) | NM_002880.3 | ATGGAGCACATACAGGGAGC (SEQ ID NO: 19) | CTAGAAGACAGGCAGCCTCG (SEQ ID NO: 20) |
| TP53 (tumor protein p53) | NM_000546.5 | ATGGAGGAGCCGCAGTCA (SEQ ID NO: 21) | TCAGTCTGAGTCAGGCCCTT (SEQ ID NO: 22) |
| FGFR1 (Fibroblast growth factor 1) | NM_023110.2 | ATGTGGAGCTGGAAGTGC (SEQ ID NO: 27) | TCAGCGGCGTTTGAGTC (SEQ ID NO: 28) |
| FGFR2 (Fibroblast growth factor 2) | NM_000141.4 | ATGGTCAGCTGGGGTCG (SEQ ID NO: 29) | TCATGTTTTAACACTGCCGTTTATG (SEQ ID NO: 30) |
| KRAS (Kirsten rat sarcoma viral oncogene homolog) | NM_004985.3 | GCCTGCTGAAAATGACTGAATATAAAC (SEQ ID NO: 31) | TTACATAATTACACACTTTGTCTTTGACTTC (SEQ ID NO: 32) |
| SMAD2 (SMAD family member 2) | NM_005901.5 | ATGTCGTCCATCTTGCCATTC (SEQ ID NO: 33) | TTATGACATGCTTGAGCAACG (SEQ ID NO: 34) |

Once the PDM gene regions are amplified, a second PCR reaction is performed to add to the 5' end of each PDM gene sequence, a promoter (either constitutive promoter such as CMV or an inducible promoter such as tetracycline promoter) and to the 3' end an IRES followed by a fluorescent reporter gene (such as GFP, RFP, BFP, or any other reporter gene, as designated).

In some examples, the addition of the promoter and IRES+fluorescent reporter elements is performed by molecular biology cloning tools, by fusing the PCR products to the desired elements by PCR approaches, ligation enzymes or recombination approaches (such as T4 DNA ligase or InFusion enzymes (Clontech), respectively).

When the full length nucleic acid molecule is formed (i.e. 5' promoter-PDM-3'IRES+Reporter (or any other order of these elements)), amplification using a PCR reaction is performed, to obtain sufficient amount of the nucleic acid molecule for transfection into cells.

In some cases, amplification of the nucleic acid molecule is achieved by ligating the full length nucleic acid molecule into an appropriate expression vector and transformation into bacteria. Plasmids thus formed are extracted using standard plasmid extraction kits such as Qiagen QIAprep Miniprep kit. In some case, the linear PCR fragments of the various PDMs are used for transfection into test cells.

Generation of FTRs:

The following sets of primers were used for the PCR amplification of the target portions of the following FTRs (Table 2):

TABLE 2

| FTR (name) | Accession number | 5' primer | 3' primer |
|---|---|---|---|
| AKT1 (v-akt murine thymoma viral oncogene homolog 1) | NM_001014431.1 | ATGAGCGACGTGGCTATTGT (SEQ ID NO: 1) | TCAGGCCGTGCCGCTGGC (SEQ ID NO: 2) |
| ERK2 (mitogen-activated protein kinase 1) | NM_002745.4 | ATGGCGGCGGCGGCGG (SEQ ID NO: 35) | TTAAGATCTGTATCCTGG (SEQ ID NO: 36) |

TABLE 2-continued

| FTR (name) | Accession number | 5' primer | 3' primer |
|---|---|---|---|
| ERF (Ets2 repressor factor) | NM_006494.2 | ATGAAGACCCCGGCG GACAC (SEQ ID NO: 37) | TCAGGAGTCTCGGTG CTCC (SEQ ID NO: 38) |
| JNK1a1 (mitogen-activated protein kinase 8 alpha 1) | NM_002750.3 | ATGAGCAGAAGCAAG CG (SEQ ID NO: 39) | TCACTGCTGCACCTG TGC (SEQ ID NO: 40) |
| RelA (v-rel avian reticulo-endotheliosis viral oncogene homolog A) | NM_021975.3 | ATGGACGAACTGTTC CCCCT (SEQ ID NO: 42) | TAGGAGCTGATCTGA CTCAGC (SEQ ID NO: 41) |
| P38b (mitogen-activated protein kinase 11) | NM_002751.5 | ATGTCGGGCCCTCG (SEQ ID NO: 43) | TCACTGCTCAATCTC CAGGC (SEQ ID NO: 44) |
| STAT3 (signal transducer and activator of transcription 3) | NM_139276.2 | ATGGCCCAATGGAAT CAG (SEQ ID NO: 45) | TCACATGGGGGAGGT AGC (SEQ ID NO: 46) |

Transfection of Expression Constructs (FTR and PDM Mixtures)

According to a predesigned matrix, each reporter gene (FTR) that is used in the analysis is mixed with either a control wild type PDM gene or a test PDM gene, prepared as described above, and mixed with appropriate transfection reagents.

In one option, the transfection mixes are placed and optionally dehydrated on an appropriate solid support substrate. In various settings, the substrate includes various solid substrates, such as: microscope slides, chip, cell culture plates, multi-plate wells, 96-well plates, 384-well plates and the like. Each mixture is placed in a designated, traceable locus/spot (i.e. a designated well or a designated location on the slide or chip). To the transfection mixtures on the substrate, a fixed number of cells (in the range of about 100 to 100,000, depending on the substrate type and as described above) is dispensed onto each spot, in normal full growth media. The cells are selected from HeLa cells, HEK 293 cells, NCI60 cell lines such as A549, EKVX, T47D, HT29 or any other suitable cell line, based on the tested PDM and assay. The test cells are placed on the solid substrate and incubated for 12-48 hours, in accordance with the type of cell, growth media and transfection conditions. The incubation time allows the cells to adhere to the substrate, and to introduce and express the FTR and PDM.

In another option, cells are plated on the solid substrate according to a predesigned matrix (in a designated, traceable locus/spot (i.e. a designated well or a designated location on the slide or chip)). After a predetermined period of time, the cells are transfected with the FTR and the appropriate PDM (WT PDM or test PDM), under appropriate transfection conditions. The FTR and the appropriate PDM may be located on two separate molecules, or on a single molecule encoding for both genes.

Assay Implementation: Inducible Promoter

Following adequate expression of the reporter FTR, growth media is replaced with low serum media (to remove any growth factors/ligands present in the media), to reduce to minimum background stimulated signaling.

When signaling level is significantly reduced (within 4 to 16 hours), induction of PDM expression is initiated. This is achieved by addition of tetracyclin when using a tetracyclin inducible promoter and ecdysone when using an ecdysone inducible promoter.

In some examples, interstitial fluid (IF) and/or anti-cancer drugs are added to induce expression of the PDM, to thereby test the effect of the IF or drug on the PDM.

Assay Implementation—Constitutive Promoter

Following adequate expression of FTR and PDM in the cells (both under the control of a constitutive promoter), growth media is replaced with low serum media (to remove of any growth factors/ligands present in the media) to reduce to minimum background stimulated signaling.

In some examples, interstitial fluid and/or anti-cancer drugs are added to induce expression of the PDM, and thereby test the effect of the IF or drug on the PDM.

Image Acquisition and Analysis

Following PDM expression (30 hours after transfection), cells are fixed by washing 3 times with phosphate buffered saline (PBS), incubation for 5 minutes in 4% paraformaldehyde (PFA), and 3 subsequent washes with PBS. The slide is then covered by a cover slip and the localization of each corresponding FTR is imaged.

Image analysis of each FTR, both in control wild-type cells as well as in the PDM transfected cell, is performed and comparison is made. The difference between the localization of the FTR in control cells vs. PDM transfected cells, is quantified, and used to determine whether an oncogenic or a wild type form of the tested PDM was present in the tested sample. The quantification is done using standard image analysis software, such as ImageJ.

An exemplary assay using HeLa cells as the assay cells:

Day 0: slides are precoated with poly-1-lysine 0.01%, for 5 minutes at room temperature (RT) and then washed with sterile water (DDW). The water is aspirated and the slides are dried for 2 hrs. HeLa cells are plated (15000 cells) in 200 µl complete medium for each well (complete medium: DMEM, 10% FBS, 1% pen/strep (P/S)).

Day 1: Transfection reagent (FugeneHD reagent (Promege, Cat. NO. E2311) is warmed to RT and Vortexed. For each well, a transfection mix is prepared in tubes, which includes: 50/100/200 ng expression construct of the PDM in tubes; 50/100 ng of expression construct of the appropriate FTR; Optimem buffer (to a total of 10 µl) and FugeneHD (1 µl for each 3 µg of DNA). The transfection mixture is incubated at RT for 15 minutes. The cell medium is aspirated from the wells, and each well is supplemented with 100 µl transfection medium (DMEM, 10% FCS, no antibiotics). 10 µl of the transfection mixture is added to each well. The cells are then incubated at 37° C. in humidified incubator (5% CO2). Six-eight hours later, the medium is replaced to starvation medium 1 (DMEM with 0.1% FCS, 1% Pen/Strep) and the cells are incubated at 37° C. humidified incubator, 5% CO2. For assays which require a 24 hour incubation of a drug/chemical inhibitor, it is added at the needed concentration. For assays which require incubation with drug: Replace medium with starvation medium 2 supplemented with the drug as needed. The cells are then incubated at 37° C. in humidified incubator (5% CO2). Additionally, if a shorter incubation time of a drug is needed, it may be conducted.

Day 2: 26 hours later (i.e., 4 hours prior to fixation of the cells), the medium is changed to starvation medium 2 (DMEM with 1% P/S). The cells are then incubated at 37° C. in humidified incubator (5% CO2).

For assays which require inducement of signaling: Replace medium with starvation medium 2 supplemented with the inducer as needed. The cells are then incubated at 37° C. in humidified incubator (5% CO2). Additionally, if a shorter incubation time of a drug/chemical inhibitor is needed, it may be conducted.

30 hours after transfection, the cells are fixed (all steps at room temp) by the following process: the cells are washed 3 times with PBS. Fixed with fixation solution (5% Glucose/4% paraformaldehyde (PFA) in PBS) for 10 minutes, Washed 3 times with PBS. The cells are optionally stained with DAPI solution, after which they are washed three times with PBS.

Example 1: Patient BRAF Mutation Confers Resistance to the ERBB2 Inhibitor Neratinib A 66 year old male was diagnosed with metastatic lung adenocarcinoma. The patient was treated with Herceptin and subsequently with Neratinib which did not provide progression free survival (PFS) and progressive disease maintained. Patient passed away after 2 months of therapy. In addition to an ERBB2/HER2 oncogenic mutation (A771_Y772insYVMA, G776C) and AKT1 amplification, a BRAF I554T mutation was identified, and was shown to be highly oncogenic using the methods disclosed herein. A needle biopsy from a liver metastatic site was used as a biological sample.

Figure 3A:
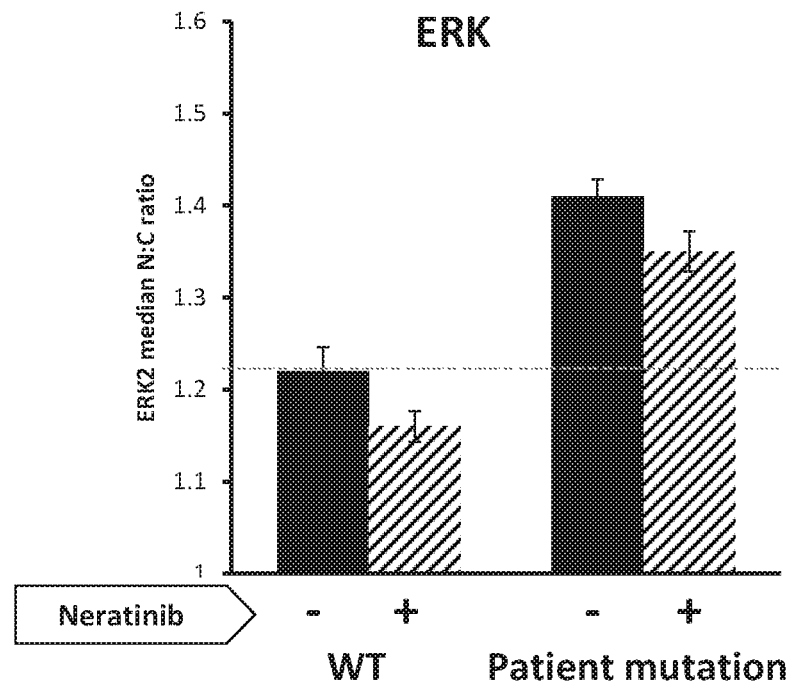
FIG. 3A—A bar graph showing results of a cell based assay in which genes encoding BRAF in wild type (BRAF-WT) or the patient mutant BRAF (BRAF mutant, (I554T)) have been expressed in test cells, along with a reporter protein (FTR, ERK2-GFP). The cells were either untreated or treated with the ERBB2 inhibitor Neratinib. Cells were fixed (30 hours later) and imaged, and the nuclear to cytoplasmic ratio (N:C) under the various experimental conditions was calculated using automated image analysis.
Figure 3B:
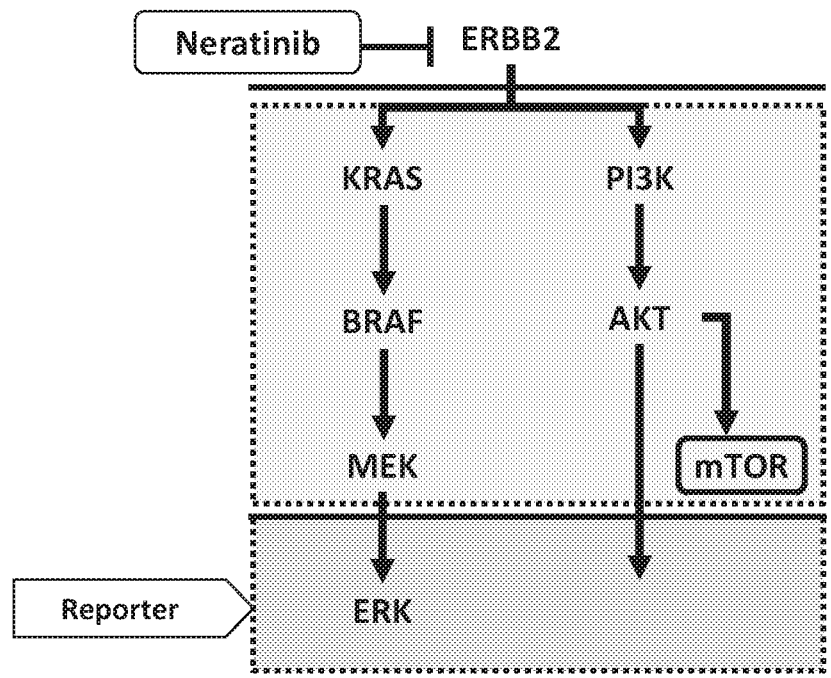

Hela assay cells were transfected with a WT BRAF or a patient mutated BRAF, along with the corresponding FTR, ERK2 GFP. Cells were left untreated or treated with the ERBB2 inhibitor Neratinib at a concentration of 600 nM, for 6 hours. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 3A-B, which show that higher N:C of ERK is observed when the mutated patient gene is transfected into the cells, as compared to the WT gene. As further shown in FIG. 3A, Neratinib treatment of cells expressing either WT BRAF or the patient mutant BRAF resulted in a minor decrease in ERK translocation to the nucleus indicating lack of inhibitory activity of the teste drug, as the activity remained significantly higher than that observed when the WT form was expressed in the cells.

Figure 4A:
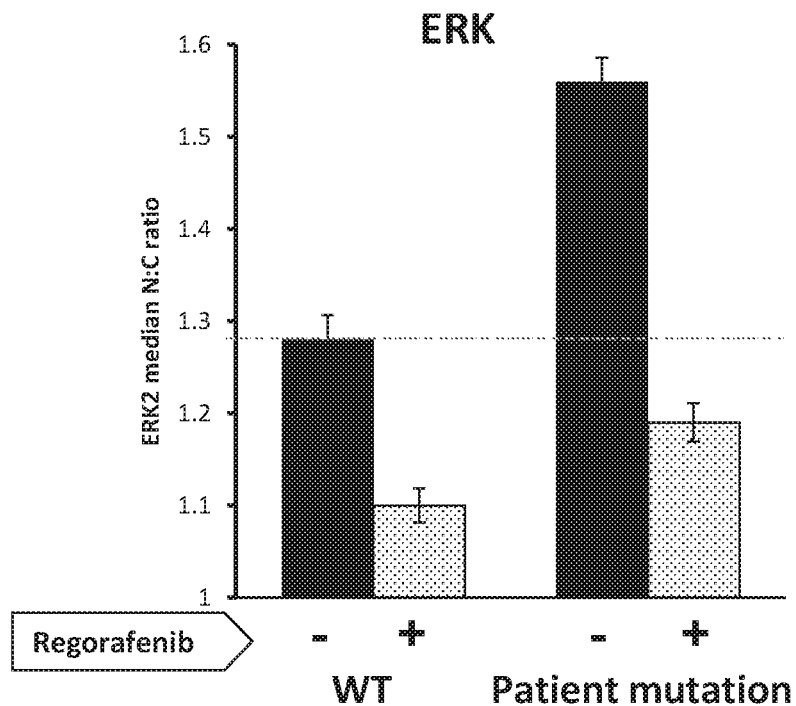
FIG. 4A—A bar graph showing results of a cell based assay in which genes encoding BRAF in wild type (BRAF-WT) or the patient mutant BRAF (BRAF mutant, (I554T)) have been expressed in test cells, along with a reporter protein (FTR, ERK2-GFP). The cells were either untreated or treated with the BRAF inhibitor Regorafenib. Cells were fixed (30 hours later) and imaged, and the nuclear to cytoplasmic ratio (N:C) under the various experimental conditions was calculated using automated image analysis.
Figure 4B:
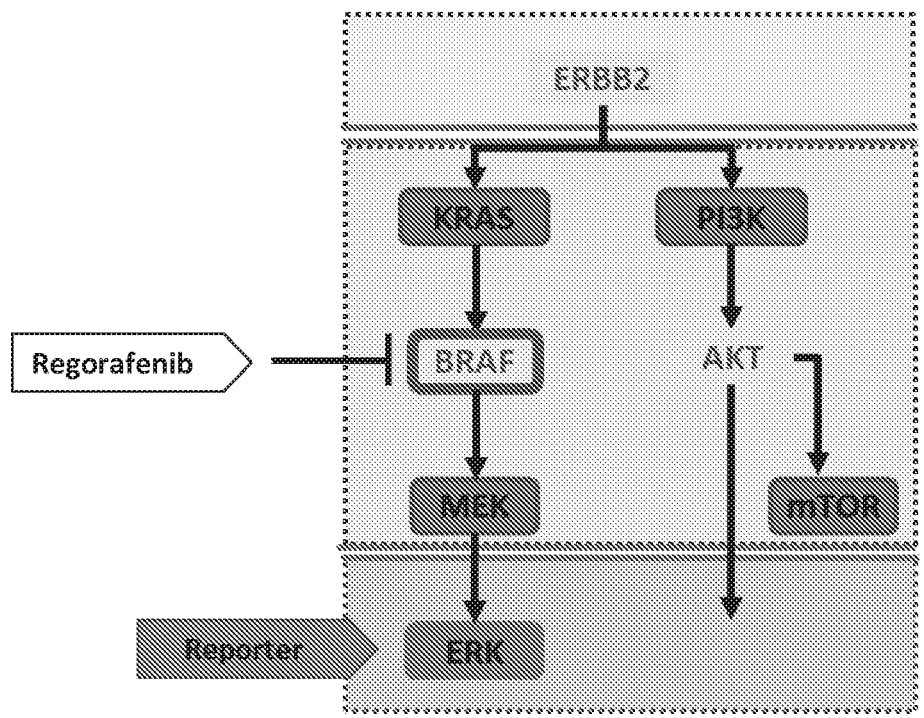

Example 2: Patient BRAF Mutation Confers Resistance to the ERBB2 Inhibitor Neratinib As in Example 1, Hela assay cells were transfected with a WT BRAF or a patient mutated BRAF (I554T), along with the corresponding FTR, ERK2 GFP. Cells were left untreated or treated with the BRAF inhibitor Regorafenib at a concentration of 1 µM, for 24 hours. 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 4A-B, which show that higher N:C of ERK is observed when the mutated patient gene is transfected into the cells, as compared to the WT gene. As further shown in FIG. 4A, when measuring the response of the patient mutant to a direct inhibitor, Regorafenib, the oncogenic activity of the mutant was abolished and reverted back to levels lower than those observed when the WT form expressed. The Regorafenib also significantly inhibited WT signaling effect.

Example 3: Patient EGFR Mutation is Resistant to Erlotinib but Sensitive to Afatinib A 34 year old female was diagnosed with stage IV lung adenocarcinoma. The patient was treated with Erlotinib together with chemotherapy and responded well. After 12 months developed resistance to treatment. This was followed by Afatinib treatment, with good response. This response was short (4 months), and after progression there was no response for either Cetuximab to Afatinib. Once resistance appeared, the following mutations were identified by sequencing (NGS) in several genes: MUTYH (p.V376L; .V390L; p.V362L; .V363L; p.V387L); EGFR (p.G719A); EGFR (p.T790M); EGFR (p.L861Q); TRIM24 (p.C595S; p.C629S); BRD3 (p.G677W); NOTCH1 (p.C222fs); BIVM-ERCC5; ERCC5 (p.M254V; p.M708V).

Previous experiments using the methods disclosed herein, identified the patient's EGFR mutation as highly oncogenic, affecting multiple pathways. The triple mutation in EGFR consists of 2 known oncogenic mutations—G719A and L861Q, as well as a 3rd oncogenic mutation (T790M) conferring resistance to several EGFR inhibitors. This mutation has been shown as a secondary mutation in EGFR, abolishing the effect of Erlotinib and Gefitinib, as it interferes with their binding site.

Figure 5A:
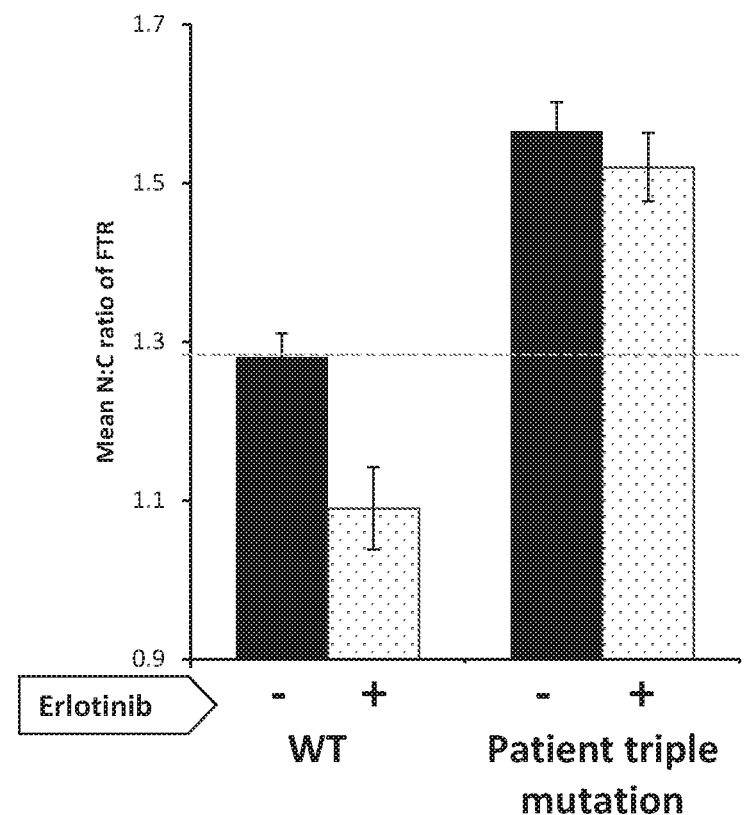
FIG. 5A-A bar graph showing the results of a cell based assay in which the genes encoding for EGFR in wild type form (EGFR WT) or triple mutant form (EGFR triple mutant, G719A, T790M and L861Q) have been expressed in test cells, along with a reporter protein (FTR, ERK2-GFP). The cells were either untreated or treated with the EGFR inhibitors Erlotinib. Cells were fixed (30 hours later) and imaged, and the nuclear to cytoplasmic ratio (N:C) under the various experimental conditions was calculated using automated image analysis.
Figure 5B:
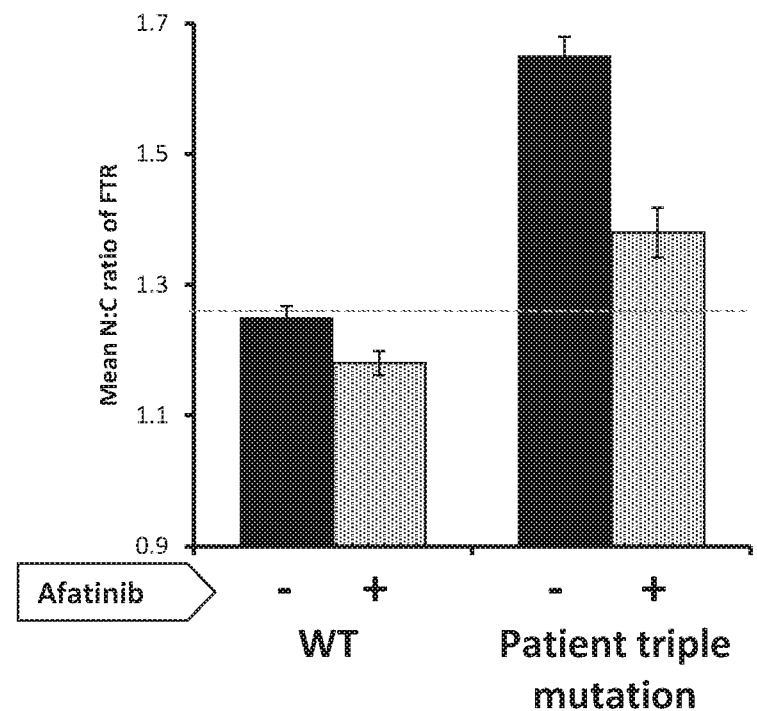

Hela assay cells were transfected with a WT EGFR or the patient mutated EGFR (EGFR G719A/T790M/L861Q), along with the corresponding FTR, ERK2-GFP. Cells were left untreated or treated with Erlotinib (the EGFR inhibitor that the patient developed resistance to), at a concentration of 300 nM, for 24 hours or with Afatinib (a second generation EGFR inhibitor, which showed some response in the patient). 30 hours after transfection, cells were fixed and imaged utilizing a fluorescence microscope. The amount of the FTR in the cytoplasm and in the nucleus was quantified. The ratio between the intensity of the FTR in the nucleus (N) and cytoplasm (C) was measured (N:C ratio). The results are presented in FIGS. 5A-B: Mutations present in the patient EGFR were of known function, therefore it was tested whether the response to specific targeted therapies will similar to the results that were seen in the clinic (i.e., resistance to Erlotinib and sensitivity to Afatinib). As shown in FIG. 5A, Erlotinib treatment potently inhibited the activity level of WT EGFR but had no effect on the patient triple mutant EGFR. This resulted from the T790M mutation known to confer resistance to this inhibitor. This is in line with the resistance reported in the patient after treatment with this drug. In contrast, as shown in FIG. 5B, the EGFR inhibitor, Afatinib, to which the patient showed a good response, was able to potently inhibit the oncogenic activity of the triple mutant EGFR in the assay system. Although the activity level was not reversed back to WT levels, the reduction in activity was significant.

Altogether, the results presented herein show that the methods disclosed herein can indeed predict the resistance and sensitivity of the two different targeted therapy drugs tested, with a high degree of significance. Further, the results presented in FIGS. 5A-B are also concordant with the outcome observed in the clinic, providing a mechanistic explanation to the efficiency of these drugs. These results thus exemplify the capabilities of the disclosed methods and systems to identify drug response of various mutations and to allow drug selection in the case of multiple drugs to the same target.

Figure 6A:
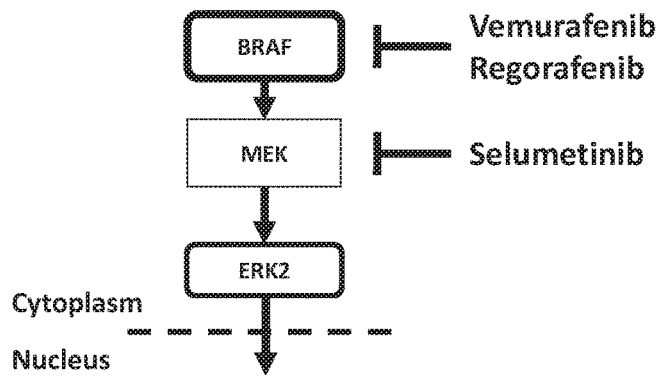
FIG. 6A—A schematic representation of the signaling pathway affected by PDM (BRAF) and the corresponding FTR (ERK2) as well as the sites of inhibition of the tested drugs (Vemurafenib, Regorafenib and Selumetinib).
Figure 6B:
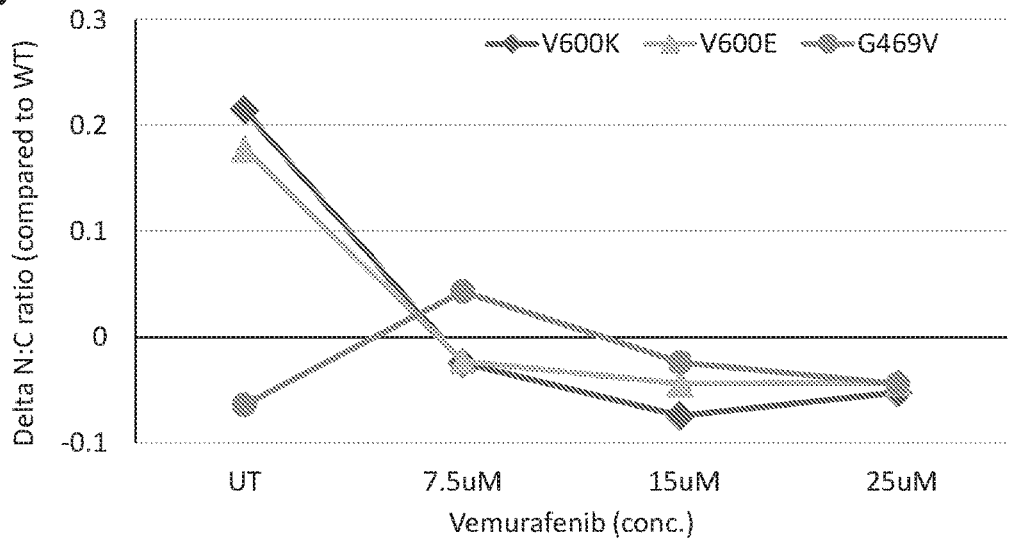
Figure 6C:
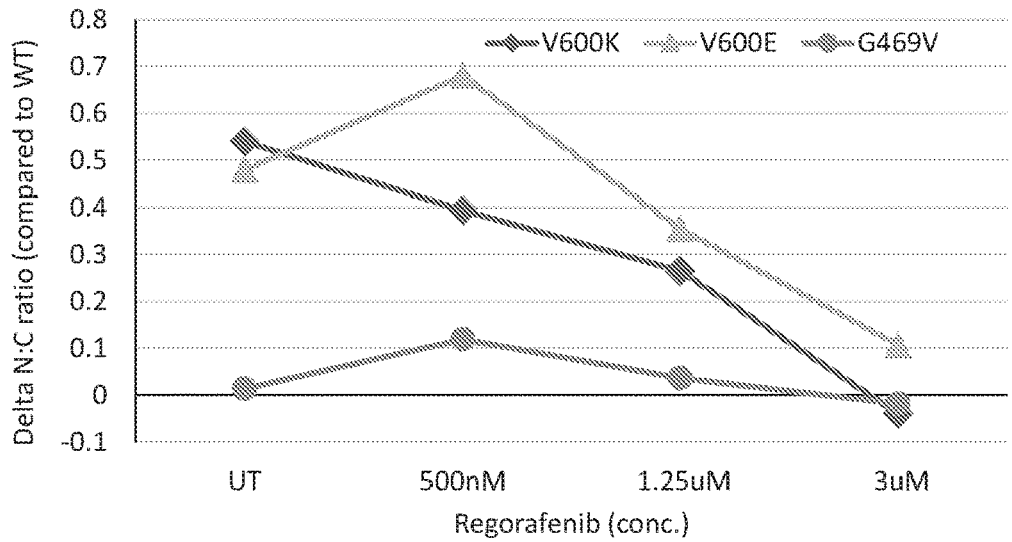
Figure 6D:
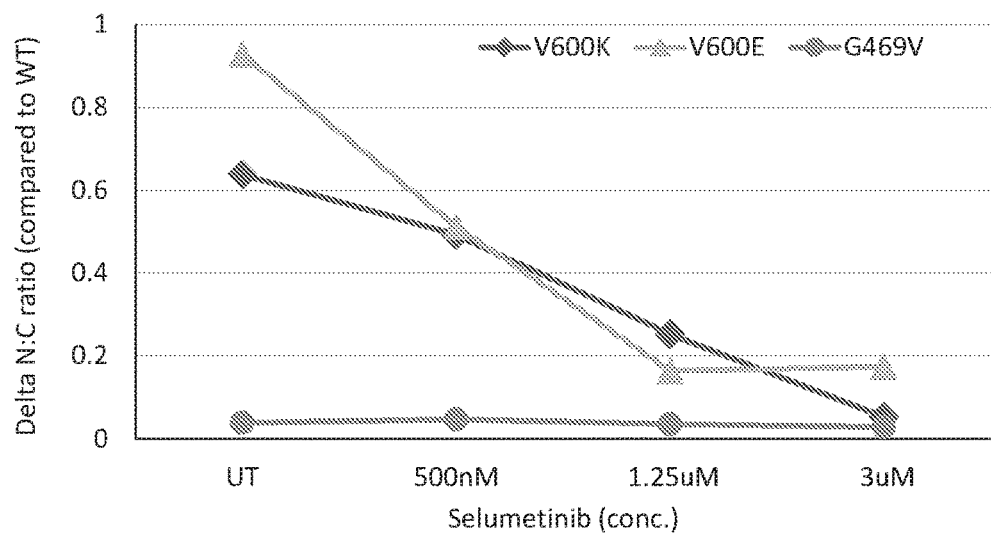
Figure 6E:
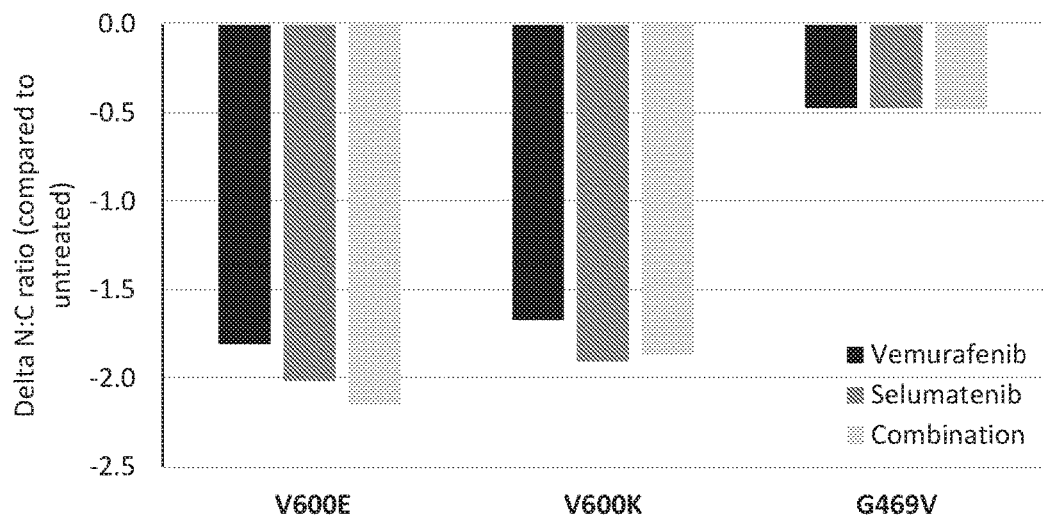
Figure 6F:
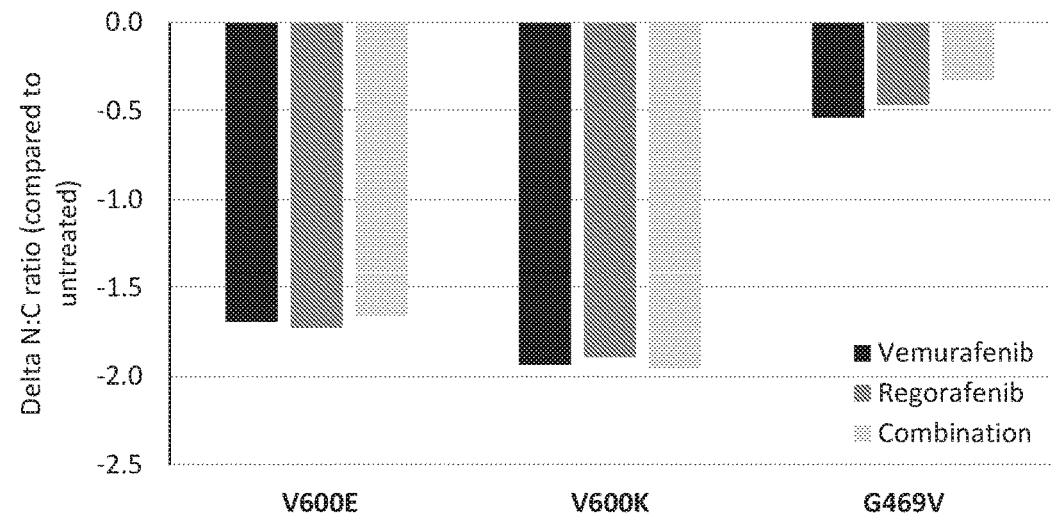

Example 4: Subcellular Translocation Assay of the ERK1/2 Pathway can Discriminate Between BRAF Response to Different Single and Multiple Targeted Therapies and Identify BRAF Resistant/Sensitive Mutations Hela assay cells were transfected with a WT BRAF or mutated BRAF, along with the corresponding FTR, ERK2-GFP. Cells were untreated or treated with the BRAF inhibitor Vemurafenib at increasing concentrations (7.5 uM-25 uM, FIG. 6B), Regorafenib (500 nM-3 uM, FIG. 6C) or the MEK1/2 inhibitor Selumetinib (300 nM-3 uM, FIG. 6D), for 18 hours. 24 hours after transfection, cells were fixed and imaged utilizing a fluorescence microscope. The amount of the FTR in the cytoplasm and in the nucleus was quantified. The difference between the WT form of BRAF and the different mutants in the ratio between the intensity of the FTR in the nucleus (N) and cytoplasm (C) was measured (Delta N:C ratio). The results presented in FIGS. 6B-D, show that increased doses of the drugs reduce the difference in ERK translocation in the mutated form as compared to the WT gene. This effect is shown to be mutation specific as Non-V600 mutants are not sensitive to the different drugs compared to the V600 mutations. As further shown in FIGS. 6E and 6F, combining two different drugs (Vemurafenib and Selumetinib or Vemurafenib and Regorafenib), does not confer an added benefit in pathway inhibition as compared to each drugs separately.

Figure 7A:
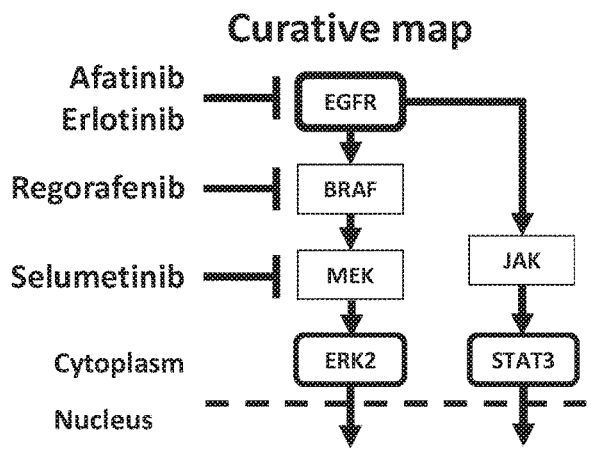
FIG. 7A—A schematic representation of the signaling pathway affected by PDM (EGFR) and the corresponding FTRs (ERK2, STAT3) as well as the inhibition sites of the test drugs (Afatinib, Selumetinib, Erlotinib, Regorafenib).
Figure 7B:
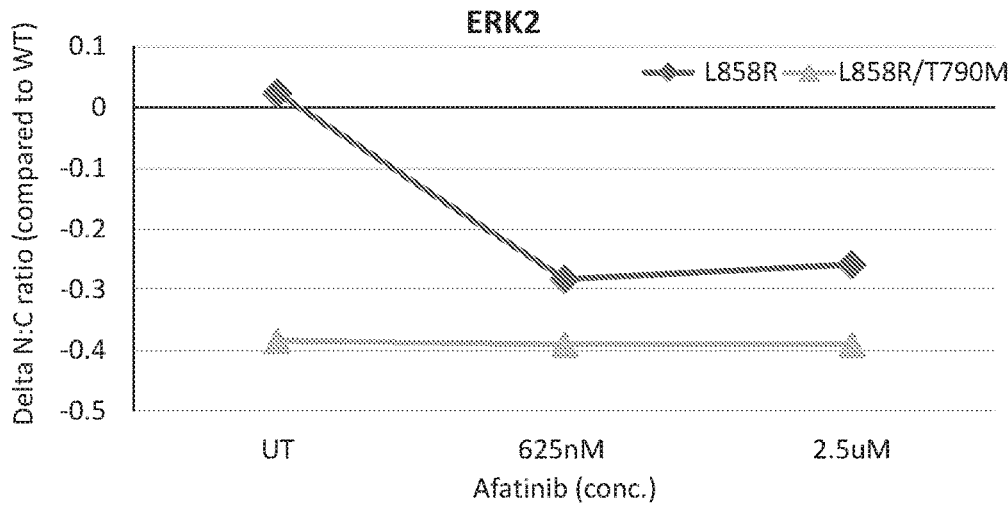
Figure 7C:
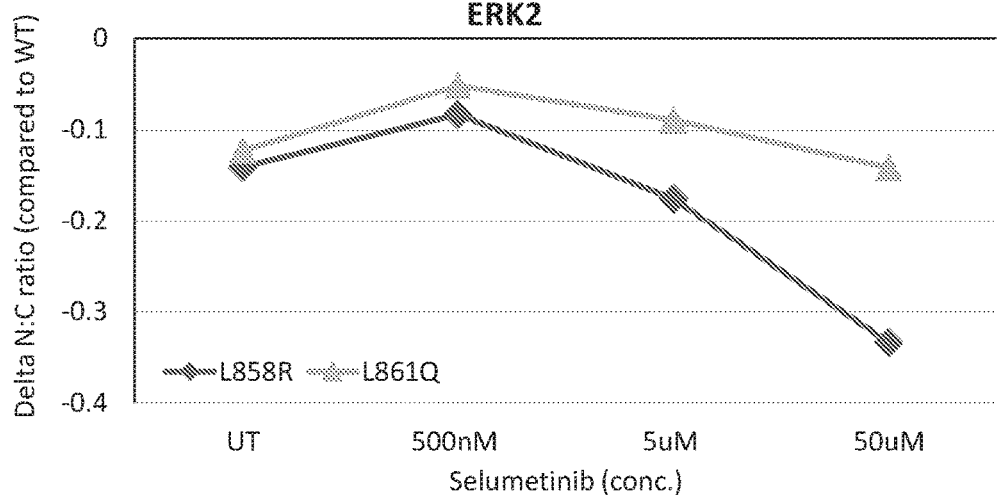
Figure 7D:
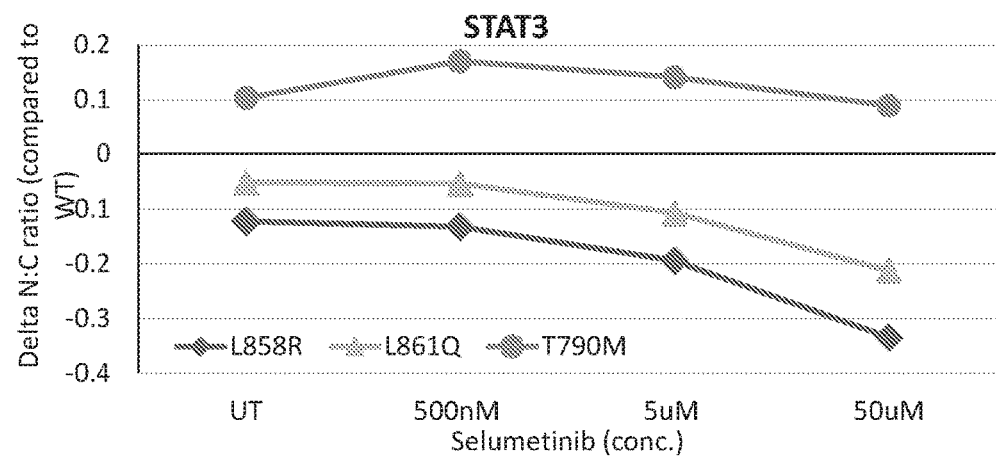
Figure 7E:
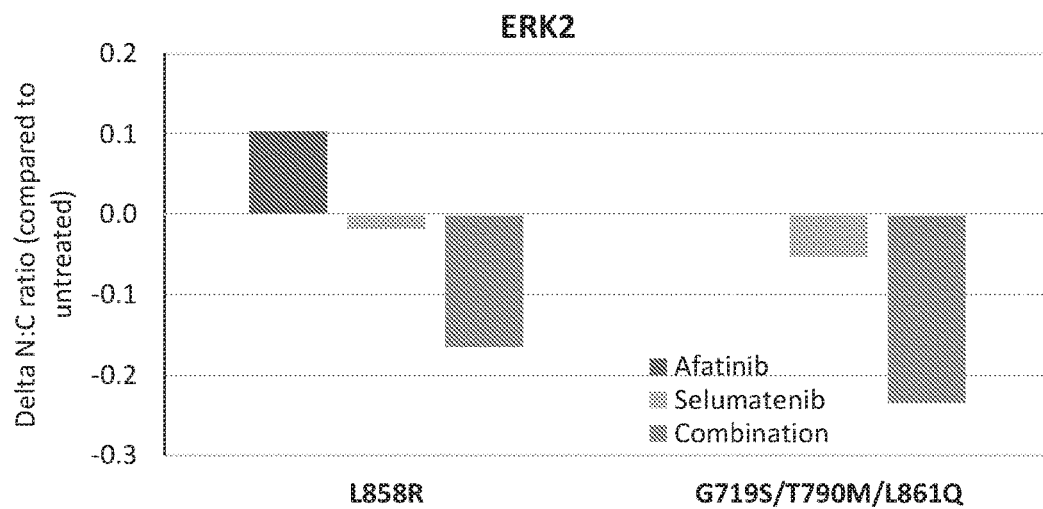
Figure 7F:
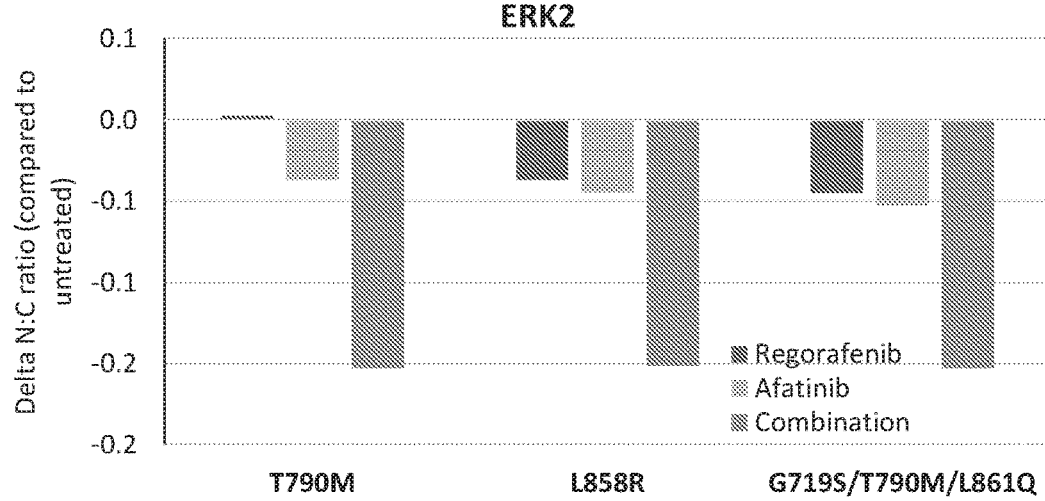

Example 5: Subcellular Translocation Assay of the ERK1/2 and STAT Pathway can Discriminate Between EGFR Response to Different Single and Multiple Targeted Therapies and Identify EGFR Resistant/Sensitive Mutations Hela assay cells were transfected with a WT-BRAF or mutated BRAF, along with the corresponding FTRs, ERK2-GFP or STAT3-GFP. Cells were left untreated or treated with the EGFR inhibitor Afatinib at increasing concentrations (625 nM-2.5 uM, FIG. 7B) or increasing concentrations of the MEK1/2 inhibitor, Selumetinib (300 nM-30 uM, FIG. 7C), for 18 hours. 24 hours after transfection, cells were fixed and imaged utilizing a fluorescence microscope. The amount of the FTR in the cytoplasm and in the nucleus was quantified. The difference between the WT form of EGFR and the different mutants in the ratio between the intensity of the FTR in the nucleus (N) and cytoplasm (C) was measured (Delta N:C ratio). The results presented in FIG. 7B, show that increased doses of the drugs reduce the difference in ERK translocation in the some of the mutated forms as compared to the WT gene. This effect is shown to be mutation specific as the L858R mutant is sensitive to the drug compared to the L858R/T790M mutation, probably due to the resistance conferred by the T790M mutation. As further shown in FIG. 7C and FIG. 7D, testing the effect of the same drug, Selumetinib, in two different signaling pathway (ERK1/2 and STAT) again shows that non-T790M containing mutants (L858R and L861Q) are sensitive to the MEK inhibitor, while the T790M mutation is non-responsive. Importantly, FIG. 7E and FIG. 7F show that combining two different drugs (Afatinib and Selumetinib or Afatinib and Regorafenib), causes an added benefit in pathway inhibition as compared to each drugs separately. The results show that combination of drugs targeting multiple targetpoints along the EGFR-ERK1/2 pathway is more effective than each drug separately, even in T790M containing mutations.

Figure 8A:
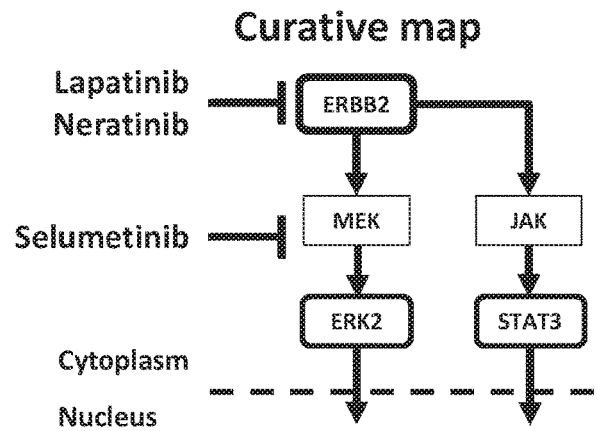
FIG. 8A—A schematic representation of the signaling pathway affected by PDM (ERBB2) and the corresponding FTRs (ERK2, STAT3) as well as the inhibition sites of the test drugs (Lapatinib, Neratinib, Selumetinib).
Figure 8B:
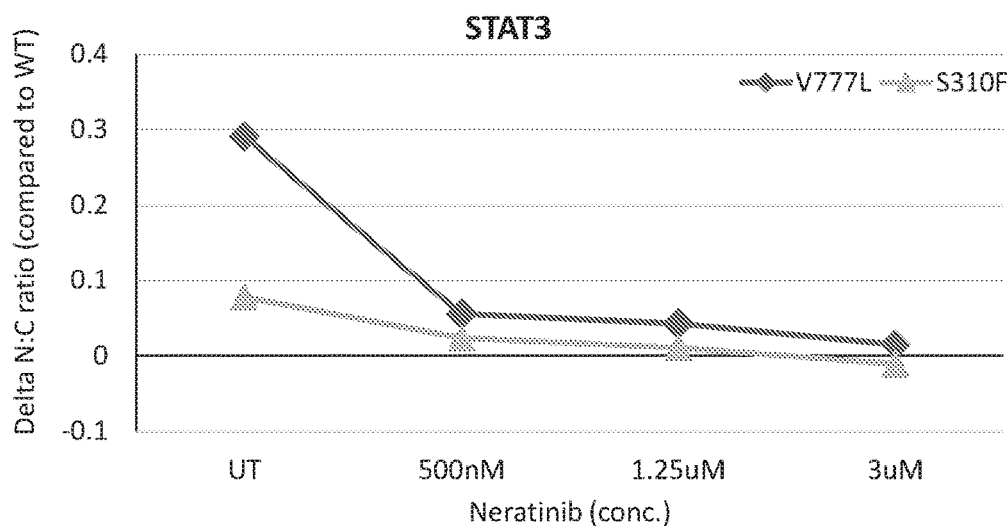
Figure 8C:
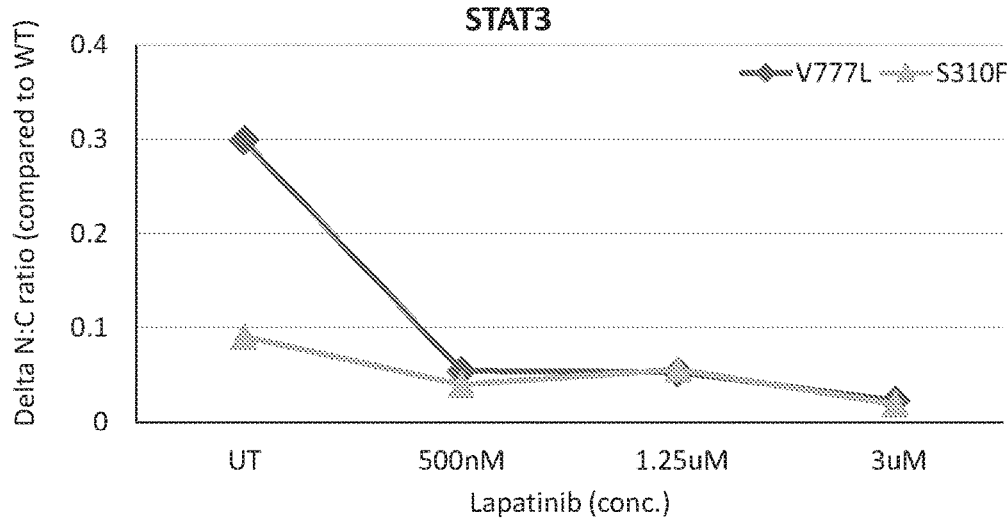
Figure 8D:
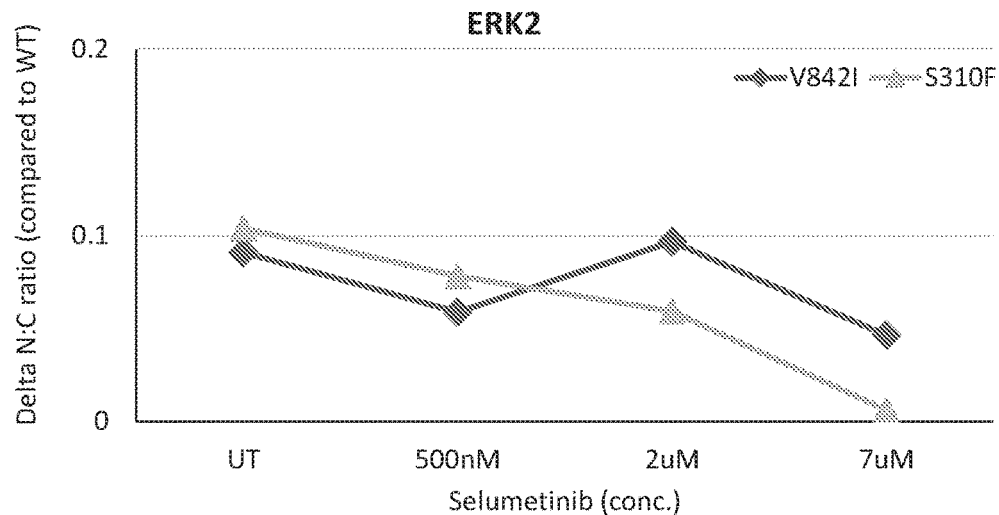
Figure 8E:
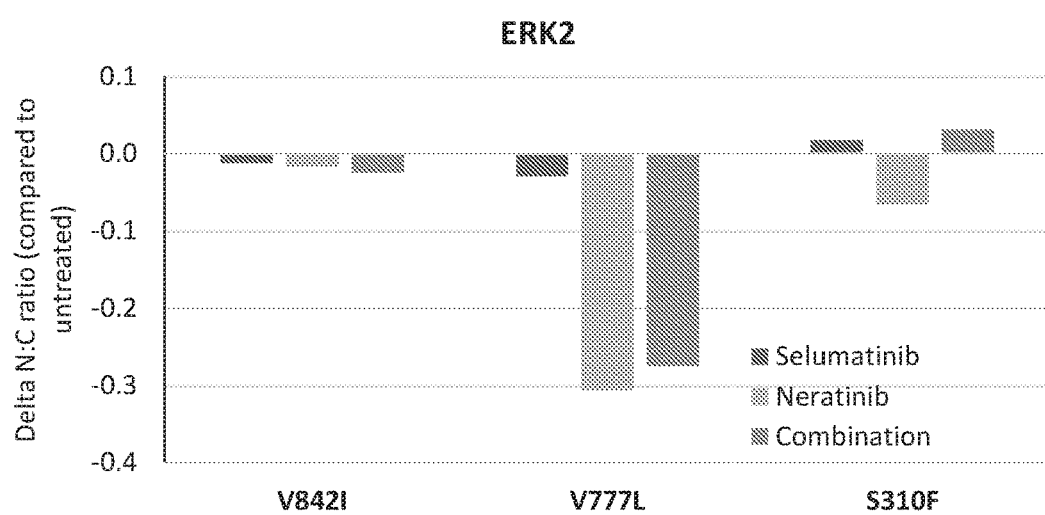
Figure 8F:
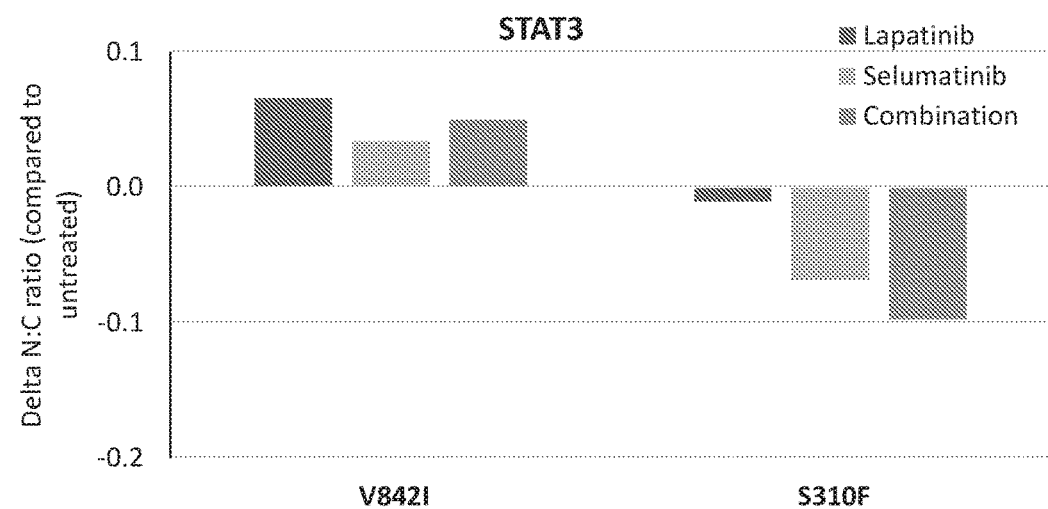

Example 6: Subcellular Translocation Assay of the ERK1/2 and STAT Pathway can Discriminate Between ERBB2 Response to Different Single and Multiple Targeted Therapies and Identify ERBB2 Resistant/Sensitive Mutations Hela assay cells were transfected with a WT ERBB2 or mutated ERBB2, along with the corresponding FTR, ERK-GFP or STAT3-GFP. Cells were left untreated or treated with increasing concentrations of ERBB2 inhibitor, Neratinib (500 nM-3 uM, FIG. 8B), or Lapatinib (500 nM-3 uM, FIG. 8C), or the MEK1/2 inhibitor, Selumetinib (500 nM-7 uM, FIG. 8D), for 18 hours. 24 hours after transfection, cells were fixed and imaged utilizing a fluorescence microscope. The amount of the FTR in the cytoplasm and in the nucleus was quantified. The difference between the WT form of ERBB2 and the different mutants in the ratio between the intensity of the FTR in the nucleus (N) and cytoplasm (C) was measured (Delta N:C ratio). The results presented in FIG. 8B and FIG. 8C, show that increased doses of the ERBB2 inhibitors reduce the difference in STAT3 translocation in the V777L mutant but not the S310F mutation. As further shown in FIG. 8D, testing the effect of the MEK inhibitor, Selumetinib, in the ERK1/2 pathway shows that the S310F mutation is sensitive to this drug, while another mutation, V842I, is unaffected. Finally, FIG. 8E and FIG. 8F show that combining two different drugs (Neratinib and Selumetinib or Lapatinib and Selumetinib), does not cause an added benefit in pathway inhibition as compared to each drugs separately, with the exception of S310F (FIG. 8F). This shows that combination of drugs targeting multiple points along the ERBB2-ERK1/2 and ERBB2-STAT3 pathways is not more effective than each drug separately.

Figure 9A:
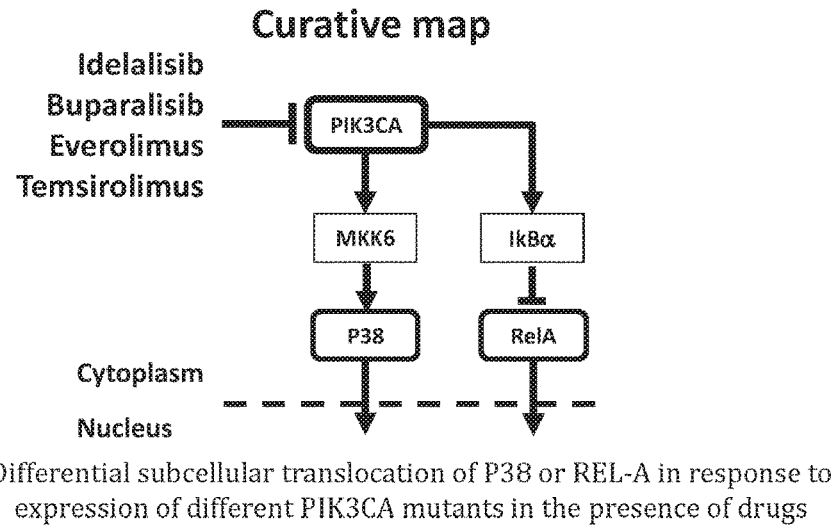
FIG. 9A—A schematic representation of the signaling pathway affected by PDM (PIK3CA) and the corresponding FTRs (P38, REL-A), as well as the inhibition sites of the test drugs (Idelalisib, Buparalisib, Everolimus, Temsirolimus).
Figure 9B:
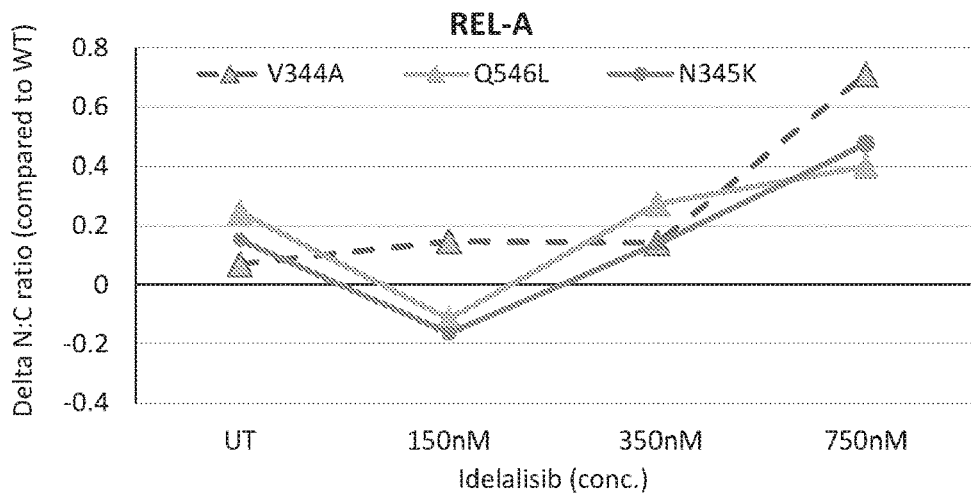
Figure 9C:
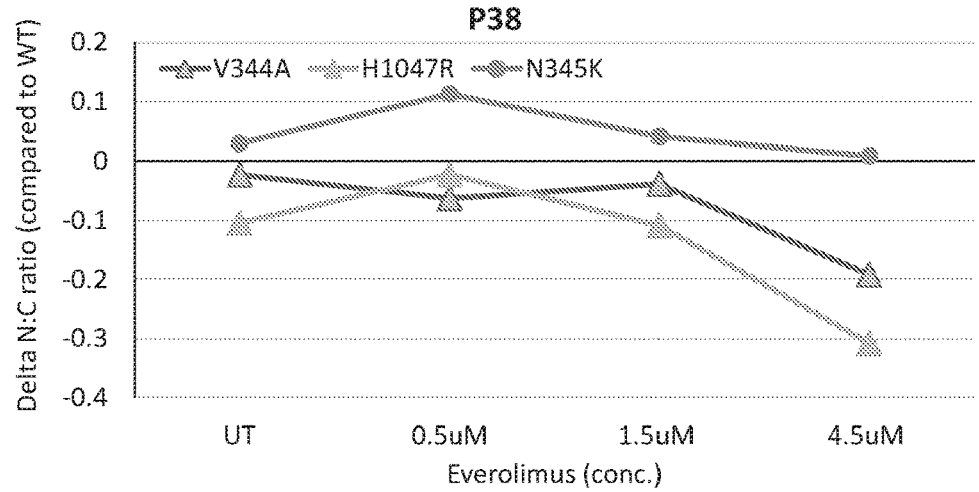
Figure 9D:
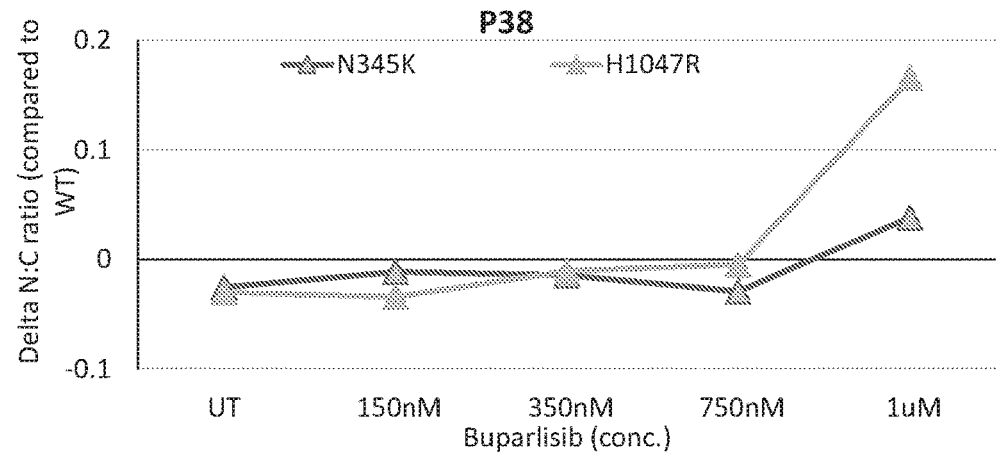
Figure 9E:
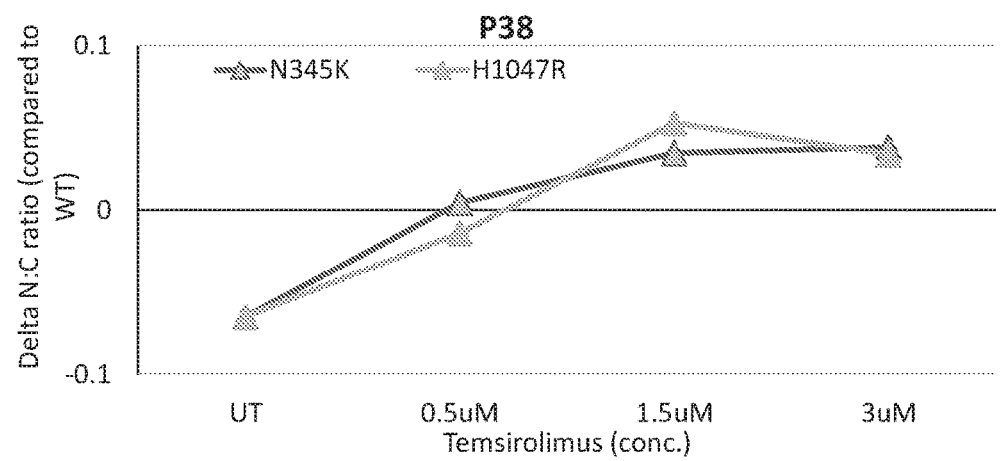
Figure 9F:
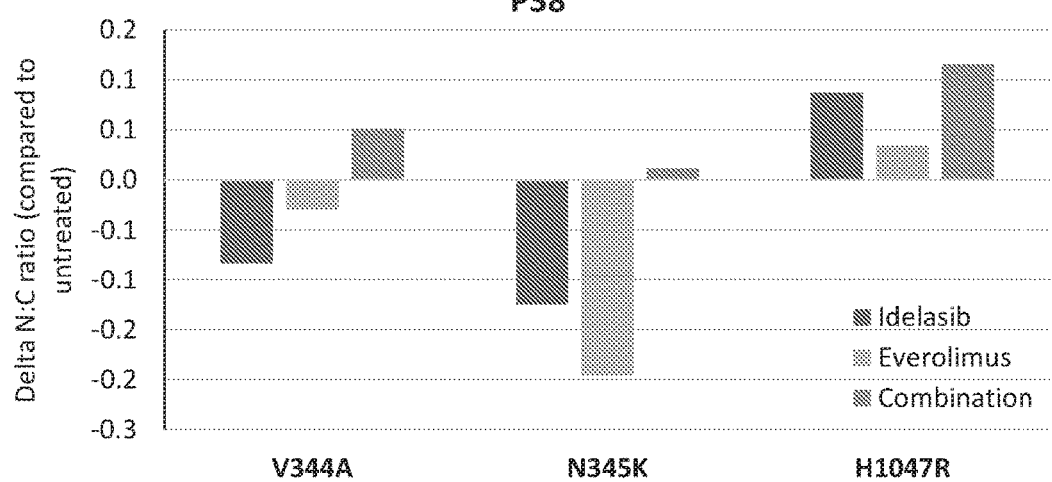

Example 7: Subcellular Translocation Assay of the P38 and NFkB Pathway can Discriminate Between PIK3CA Response to Different Single and Multiple Targeted Therapies and Identify PIK3CA Resistant/Sensitive Mutations Hela assay cells were transfected with a WT PIK3CA or mutated PIK3CA, along with the corresponding FTR, P38 or REL-A GFP. Cells were left untreated or treated with increasing concentrations of PIK3CA inhibitor, Idelalisib (150 nM-750 nM, FIG. 9B), Everolimus (0.5 uM-4.5 uM, FIG. 9C), Buparilisib (150 nM-1 uM, FIG. 9D) or Temsirolimus (0.5 uM-3 uM, FIG. 9E), for 18 hours. 24 hours after transfection, cells were fixed and imaged utilizing a fluorescence microscope. The amount of the FTR in the cytoplasm and in the nucleus was quantified. The difference between the WT form of PIK3CA and the different mutants in the ratio between the intensity of the FTR in the nucleus (N) and cytoplasm (C) was measured (Delta N:C ratio). The results presented in FIG. 9B show that increased doses of the PIK3CA inhibitor increase the magnitude of REL-A translocation in the V344A, Q546L and N345K mutants. Similarly, FIG. 9C, shows that increased doses of the PIK3CA inhibitor decreases the magnitude of P38 translocation in the V344A and H1047R mutants, but does not affect the N345K mutant. As further shown in FIG. 9D and FIG. 9E, testing the effect of additional PIK3CA inhibitors, Buparlisib and Temsirolimus, in the P38 pathway, show that the N345K and H1047R mutations are sensitive to the first drug (FIG. 9D) but not the latter (FIG. 9E). Finally, FIG. 9F shows that combining two different drugs (Idelalisib and Everolimus), does not cause an added benefit in pathway inhibition as compared to each drugs separately, with the exception of H1047R. This shows that combination of drugs targeting multiple points along the PIK3CA-P38 pathways is generally not more effective than each drug separately, but is dependent on specific mutations.

Figure 10A:
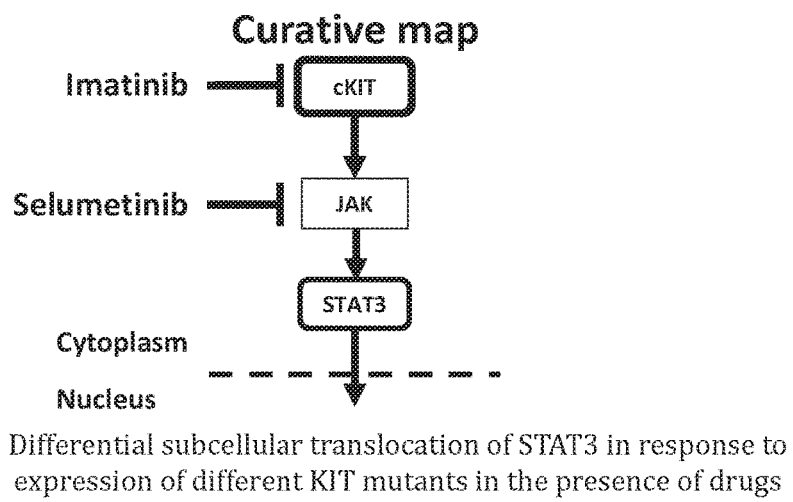
FIG. 10A—A schematic representation of the signaling pathway affected by PDM (cKIT) and the corresponding FTR (STAT3), as well as the inhibition sites of the test drugs (Imatinib and Selumetinib).
Figure 10B:
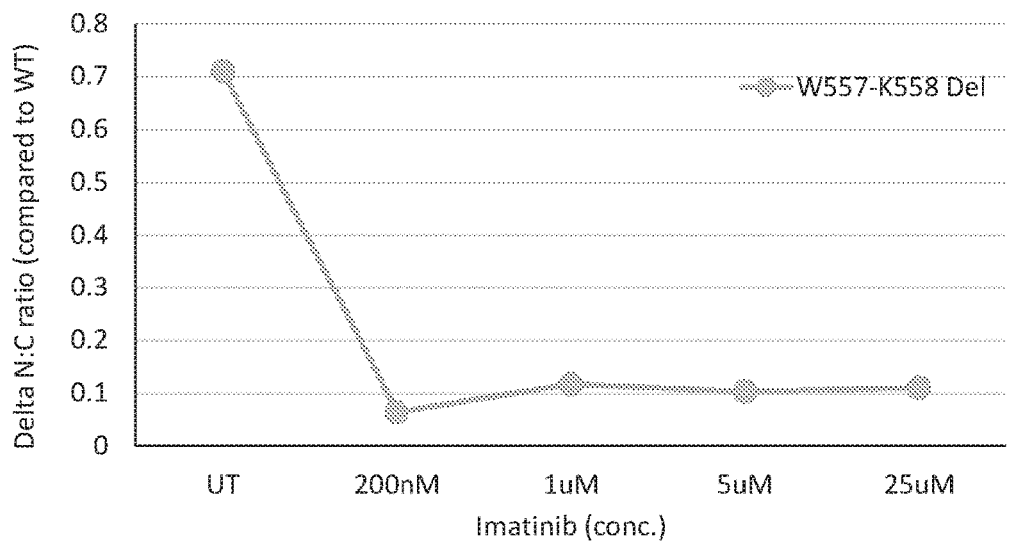
Figure 10C:
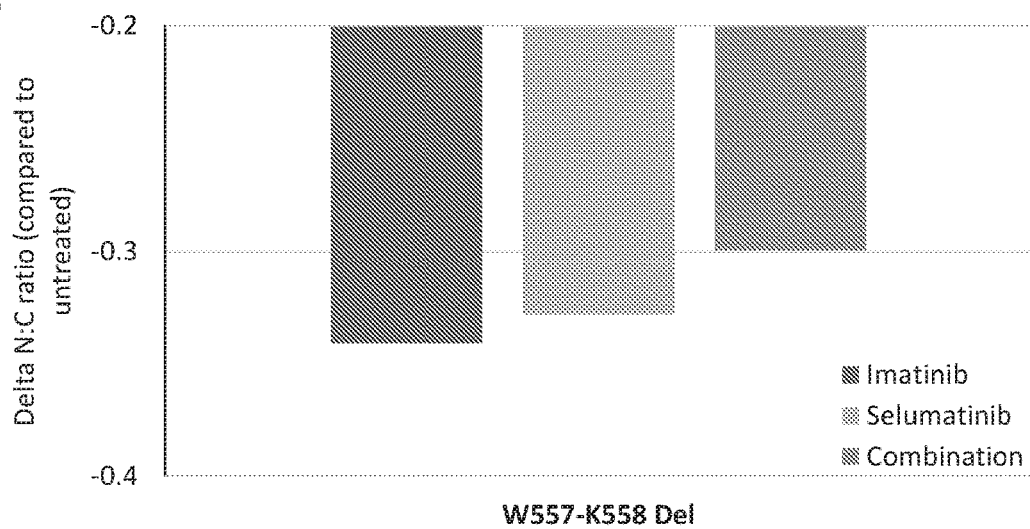

Example 8: Subcellular Translocation Assay of the STAT3 Pathway can Discriminate Between cKIT Response to Different Single and Multiple Targeted Therapies and Identify cKIT Sensitive Mutations Hela assay cells were transfected with a WT cKIT or mutated cKIT, along with the corresponding FTR, STAT3 GFP. Cells were left untreated or treated with the cKIT inhibitor Imatinib at increasing concentrations (200 nM-25 uM, FIG. 10B) for 18 hours. 24 hours after transfection, cells were fixed and imaged utilizing a fluorescence microscope. The amount of the FTR in the cytoplasm and in the nucleus was quantified. The difference between the WT form of cKIT and the different mutants in the ratio between the intensity of the FTR in the nucleus (N) and cytoplasm (C) was measured (Delta N:C ratio). The results presented in FIG. 10B show that increased doses of the cKIT inhibitor decreases the magnitude of STAT3 translocation in the W557-K558del mutant, apparently reaching maximal effect at 200 nM. Moreover, FIG. 10C shows that combining two different drugs (Imatinib and Selumetinib), does not cause an added benefit in pathway inhibition as compared to each drugs separately.

Figure 11A:
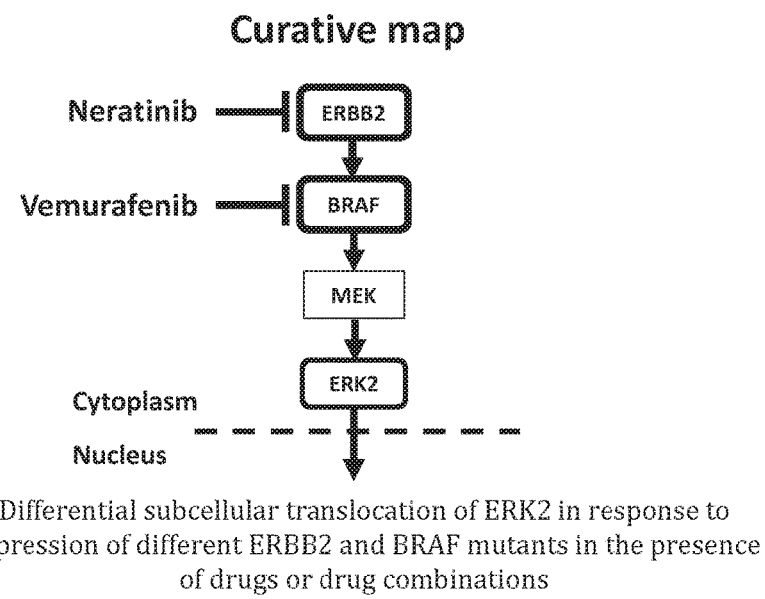
FIG. 11A—A schematic representation of the signaling pathway affected by PDMs (ERBB2 and BRAF) and the corresponding FTR (ERK2) as, well as the inhibition sites of the tested drugs (Neratinib, Vemurafenib).
Figure 11B:
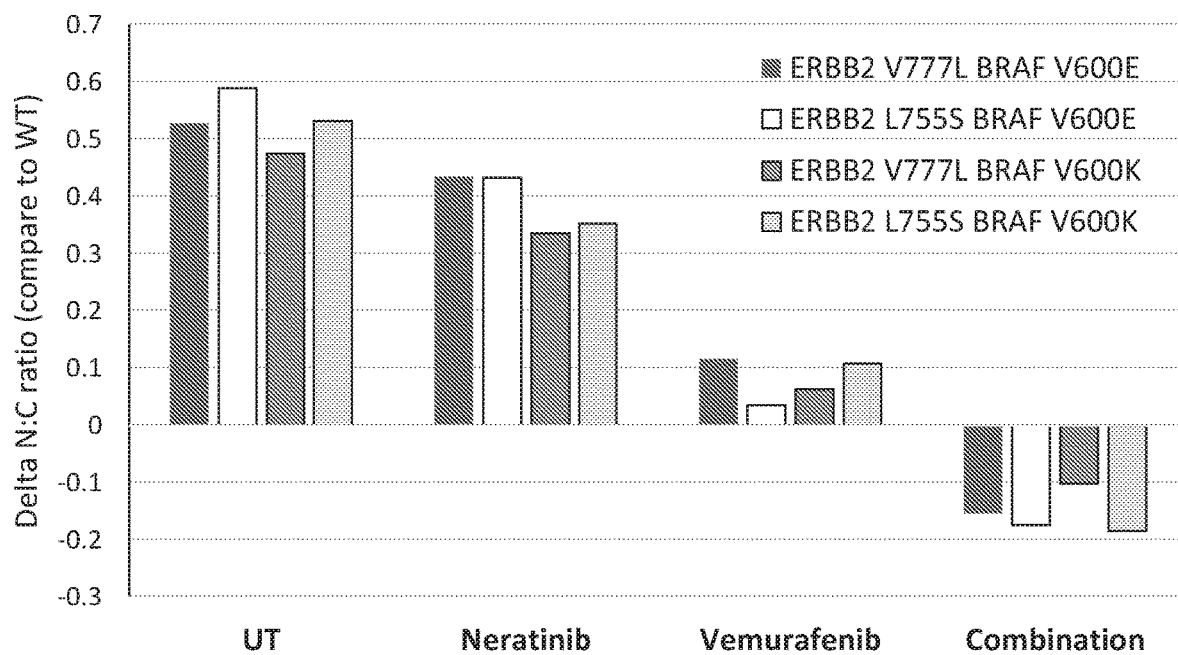

Example 9: Subcellular Translocation Assay of the ERK1/2 Pathway can Discriminate Between ERBB2 and BRAF Response to Different Single and Multiple Targeted Therapies Separately and in Combination Hela assay cells were transfected with a WT ERBB2 or BRAF or a mutated ERBB2, mutated BRAF or a combination of both, along with the corresponding FTR, ERK2-GFP. Cells were left untreated or treated with the ERBB2 inhibitor Neratinib, the BRAF inhibitor Vemurafenib or a combination of both drugs (FIG. 11B) for 18 hours. 24 hours after transfection, cells were fixed and imaged utilizing a fluorescence microscope. The amount of the FTR in the cytoplasm and in the nucleus was quantified. The difference between the WT form of both genes and the different mutants in the ratio between the intensity of the FTR in the nucleus (N) and cytoplasm (C) was measured (Delta N:C ratio). The results presented in FIG. 11B show that while each drug separately has the capacity to inhibit the ERK1/2 pathway to some extent, combining the two different drugs (Neratinib and Vemurafenib), results in a synergistic inhibition, as an added benefit in pathway inhibition is observed as compared to the effect of each drug when provided separately.

Figure 12A:
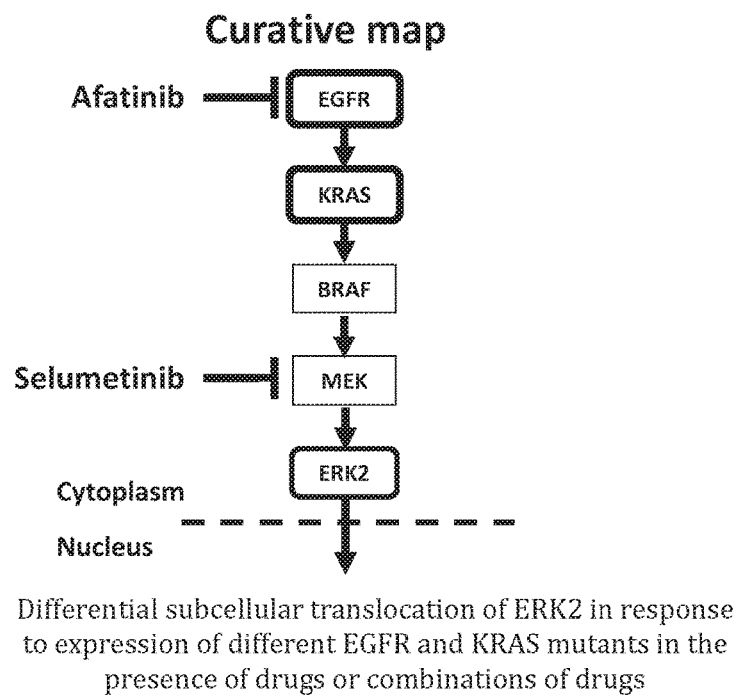
FIG. 12A—A schematic representation of the signaling pathway affected by PDMs (EGFR and KRAS) and the corresponding FTR (ERK2) as well as the inhibition sites of the test drugs (Afatinib, Selumetinib).
Figure 12B:
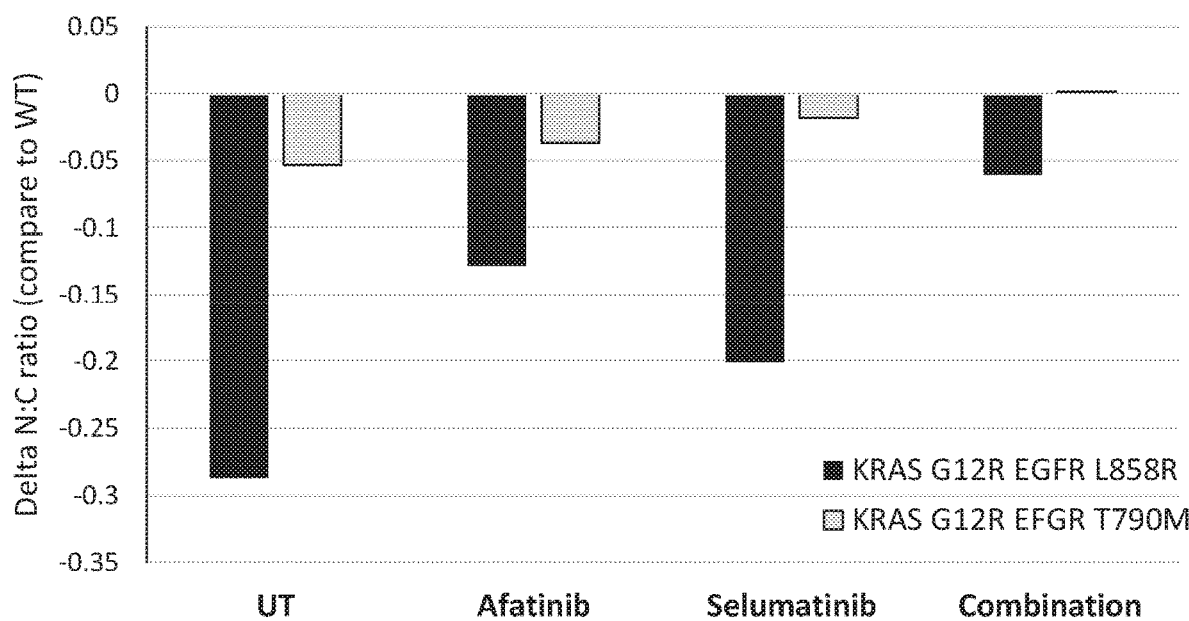

Example 10: Subcellular Translocation Assay of the ERK1/2 Pathway can Discriminate Between EGFR and KRAS Response to Different Single and Multiple Targeted Therapies Separately and in Combination Hela assay cells were transfected with a WT EGFR or KRAS or a mutated EGFR, mutated KRAS or a combination of both, along with the corresponding FTR, ERK2-GFP. Cells were left untreated or treated with the EGFR inhibitor Afatinib, the MEK1/2 inhibitor Selumetinib or a combination of both drugs (FIG. 12B) for 18 hours. 24 hours after transfection, cells were fixed and imaged utilizing a fluorescence microscope. The amount of the FTR in the cytoplasm and in the nucleus was quantified. The difference between the WT form of both genes and the different mutants in the ratio between the intensity of the FTR in the nucleus (N) and cytoplasm (C) was measured (Delta N:C ratio). The results presented in FIG. 12B show that while each drug separately has the capacity to inhibit the ERK1/2 pathway to some extent, only combining the two different drugs (Afatinib and Selumetinib), causes an added benefit in pathway inhibition as compared to effect of each drug, when provided separately.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of identifying drugs capable of suppressing the effect of patient specific mutations, comprising the steps of:
   a) forming an addressable array of a first set of expression constructs encoding one or more mutant protein comprising one or more mutation identified in a patient, and a second set of expression constructs encoding corresponding wild type proteins;
   b) adding to each locus in the array an expression vector encoding a specific Fluorescence Translocation Reporter (FTR) comprising a signaling protein linked to a fluorescent reporter protein, the signaling protein is downstream in a signaling pathway involving the protein to be expressed in the locus and changes its subcellular localization when the pathway is activated;
   c) adding viable assay cells to each locus under conditions enabling transfection of the expression constructs and expression vectors into the assay cells;
   d) incubating the assay cells under conditions allowing expression of the expression constructs and expression vectors in the assay cells, wherein each cell co-expresses a mutant protein comprising one or more mutation identified in the patient or its corresponding wild type protein, and an FTR;
   e) adding a drug to designated loci in the array; and
   f) comparing at least one of localization of the FTR and translocation of the FTR in assay cells expressing the mutant protein with assay cells expressing the corresponding wild type protein in the presence and absence of the drug,
   wherein a disparate result between the assay cells expressing the mutant protein and the assay cells expressing the corresponding wild type protein indicates signaling pathway activation by the mutant protein and thus an oncogenic effect of the one or more mutation identified in the patient,
   and wherein a disparate result between the assay cells expressing the mutant protein in the presence of the drug and assay cells expressing the mutant protein in the absence of the drug is indicative that the drug is capable of suppressing the oncogenic effect of the one or more mutation identified in the patient.

2. The method of claim 1, wherein the drug is an anticancer drug.

3. The method of claim 1, wherein step (e) comprises adding a combination of drugs to designated loci in the array and step (0 comprises comparing at least one of localization of the FTR and translocation of the FTR in assay cells expressing the mutant protein with assay cells expressing the corresponding wild type protein in the presence and absence of the combination of drugs, wherein a disparate result between the assay cells expressing the mutant protein in the presence of the combination of drugs and assay cells expressing the mutant protein in the absence of the combination of drugs is indicative that the combination of drugs is capable of suppressing the oncogenic effect of the one or more mutation identified in the patient.

4. The method of claim 1, wherein step (e) comprises adding varying concentrations of the drug to designated loci in the array and step (0 comprises determining a dose response by comparing at least one of localization of the FTR and translocation of the FTR in assay cells expressing the mutant protein in the presence of the varying concentrations of the drug with assay cells expressing the mutate protein in the absence of the drug and with assay cells expressing the corresponding wild type protein, wherein a disparate result between assay cells expressing the mutant protein in the presence of a certain concentration of the drug and assay cells expressing the mutant protein in the absence of the drug is indicative that this concentration of the drug is capable of suppressing the oncogenic effect of the one or more mutation identified in the patient.

5. The method of claim 1, wherein the localization of the FTR comprises a subcellular localization selected from: cytosol, nucleus, nucleolus, plasma membrane, endoplasmic reticulum (ER), mitochondria, Golgi apparatus, lysosomes, peroxisomes, endosomal compartments and cytoskeleton.

6. The method of claim 1, wherein the signaling protein is selected from a tumor suppressor protein, a cytoskeleton protein, a growth factor receptor, a G-protein coupled receptor, a cell adhesion protein, a protein kinase, a transcription factor, an adaptor protein and an exchange factor.

7. The method of claim 1, wherein the first set expression constructs and the second set of expression constructs comprise a promoter operably linked to the nucleic acid encoding the one or more mutant proteins or corresponding wild type proteins, wherein the promoter of the first set of expression constructs and the second set of expression constructs is selected from an inducible promoter and a constitutive promoter.

8. The method of claim 1, wherein the first set and/or second set of expression constructs comprises a double stranded linear DNA.

9. The method of claim 1, further comprising drying the expression constructs on a solid support in the presence of a transfection reagent, prior to adding the assay cells.

10. The method of claim 1, wherein step c) precedes step a) or step b).

11. A method of identifying susceptibility to drug treatment of patient specific mutations, comprising the steps of:
    a) forming an addressable array of a first set of expression constructs encoding one or more mutant protein comprising one or more mutation identified in a patient, and a second set of expression constructs encoding corresponding wild type proteins;

b) adding to each locus in the array an expression vector encoding a specific Fluorescence Translocation Reporter (FTR) comprising a signaling protein linked to a fluorescent reporter protein, the signaling protein is downstream in a signaling pathway involving the protein to be expressed in the locus and changes its subcellular localization when the pathway is activated;

c) adding viable assay cells to each locus under conditions enabling transfection of the expression constructs and expression vectors into the assay cells;

d) incubating the assay cells under conditions allowing expression of the expression constructs and expression vectors in the assay cells, wherein each cell co-expresses a mutant protein comprising one or more mutation identified in the patient or its corresponding wild type protein, and an FTR;

e) adding a drug to designated loci in the array; and f) comparing at least one of localization of the FTR and translocation of the FTR in assay cells expressing the mutant protein with assay cells expressing the corresponding wild type protein in the presence and absence of the drug, wherein a disparate result between the assay cells expressing the mutant protein and the assay cells expressing the corresponding wild type protein indicates signaling pathway activation by the mutant protein and thus an oncogenic effect of the one or more mutation identified in the patient, and wherein a disparate result between the assay cells expressing the mutant protein in the presence of the drug and assay cells expressing the mutant protein in the absence of the drug is indicative that the one or more mutation with the oncogenic effect are susceptible to treatment with the drug.

12. The method of claim 11, wherein the drug is an anti-cancer drug.

13. The method of claim 11, wherein step (e) comprises adding a combination of drugs to designated loci in the array and step (0 comprises comparing at least one of localization of the FTR and translocation of the FTR in assay cells expressing the mutant protein with assay cells expressing the corresponding wild type protein in the presence and absence of the combination of drugs, wherein a disparate result between the assay cells expressing the mutant protein in the presence of the combination of drugs and assay cells expressing the mutant protein in the absence of the combination of drugs is indicative that the one or more mutation are susceptible to treatment with the combination of drugs.

14. The method of claim 11, wherein step (e) comprises adding varying concentrations of the drug to designated loci in the array and step (0 comprises determining a dose response by comparing at least one of localization of the FTR and translocation of the FTR in assay cells expressing the mutant protein in the presence of the varying concentrations of the drug with assay cells expressing the mutate protein in the absence of the drug and with assay cells expressing the corresponding wild type protein, wherein a disparate result between assay cells expressing the mutant protein in the presence of a certain concentration of the drug and assay cells expressing the mutant protein in the absence of the drug is indicative that the one or more mutation are susceptible to treatment with this concentration of the drug.

15. The method of claim 11, wherein the localization of the FTR comprises a subcellular localization selected from: cytosol, nucleus, nucleolus, plasma membrane, endoplasmic reticulum (ER), mitochondria, Golgi apparatus, lysosomes, peroxisomes, endosomal compartments and cytoskeleton.

16. The method of claim 11, wherein the first set expression constructs and the second set of expression constructs comprise a promoter operably linked to the nucleic acid encoding the one or more mutant proteins or corresponding wild type proteins, wherein the promoter of the first set of expression constructs and the second set of expression constructs is selected from an inducible promoter and a constitutive promoter.

17. The method of claim 11, wherein the first set and/or second set of expression constructs comprises a double stranded linear DNA.

18. The method of claim 11, further comprising drying the expression constructs on a solid support in the presence of a transfection reagent, prior to adding the assay cells.

19. The method of claim 11, wherein step c) precedes step a) or step b).

20. A method of identifying drugs capable of suppressing the effect of patient specific mutations, comprising the steps of:

a) providing an addressable array of viable assay cells, wherein each locus in the addressable array comprises assay cells that co-express: (i) a mutant protein comprising one or more mutation identified in a patient or its corresponding wild type protein, and (ii) a specific Fluorescence Translocation Reporter (FTR) comprising a signaling protein linked to a fluorescent reporter protein, the signaling protein is downstream in a signaling pathway involving the protein expressed in the locus and changes its subcellular localization when the pathway is activated;

b) adding a drug to designated loci in the array; and c) comparing at least one of localization of the FTR and translocation of the FTR in assay cells expressing the mutant protein with assay cells expressing the corresponding wild type protein in the presence and absence of the drug, wherein a disparate result between the assay cells expressing the mutant protein and the assay cells expressing the corresponding wild type protein indicates signaling pathway activation by the mutant protein and thus an oncogenic effect of the one or more mutation identified in the patient, and wherein a disparate result between the assay cells expressing the mutant protein in the presence of the drug and assay cells expressing the mutant protein in the absence of the drug is indicative that the drug is capable of suppressing the oncogenic effect of the one or more mutation identified in the patient.

* * * * *